(12) United States Patent
Carr et al.

(10) Patent No.: US 10,888,427 B2
(45) Date of Patent: Jan. 12, 2021

(54) DISTAL REAMER FOR USE DURING AN ORTHOPAEDIC SURGICAL PROCEDURE TO IMPLANT A REVISION HIP PROSTHESIS

(71) Applicant: DEPUY SYNTHES PRODUCTS, INC., Raynham, MA (US)

(72) Inventors: Jonathan E. Carr, Warsaw, IN (US); Megan A. Hood, Warsaw, IN (US); Larry G. McCleary, Warsaw, IN (US); Michael J. Fortin, Acushnet, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 167 days.

(21) Appl. No.: 16/039,768

(22) Filed: Jul. 19, 2018

(65) Prior Publication Data

US 2018/0318089 A1    Nov. 8, 2018

Related U.S. Application Data

(62) Division of application No. 13/440,406, filed on Apr. 5, 2012, now Pat. No. 10,064,725.

(Continued)

(51) Int. Cl.
*A61B 17/16* (2006.01)
*A61F 2/30* (2006.01)
(Continued)

(52) U.S. Cl.
CPC ........ *A61F 2/30734* (2013.01); *A61B 17/164* (2013.01); *A61B 17/1637* (2013.01); *A61B 17/1659* (2013.01); *A61F 2/36* (2013.01); *A61F 2/3662* (2013.01); *A61F 2/4607* (2013.01); *A61F 2/4637* (2013.01); *A61F 2/4657* (2013.01); *A61F 2/4684* (2013.01); *A61B 17/1668* (2013.01); *A61B 2017/00464* (2013.01); *A61B 2090/062* (2016.02); *A61F 2002/3054* (2013.01);
(Continued)

(58) Field of Classification Search
CPC ............... A61F 2/30734; A61B 17/164; A61B 17/1659; A61B 17/1668
USPC ..................................... 606/80–85
See application file for complete search history.

(56) References Cited

U.S. PATENT DOCUMENTS

| 506,121 A | 10/1893 | Koch |
| 742,521 A | 10/1903 | Terry |

(Continued)

FOREIGN PATENT DOCUMENTS

| CN | 2495265 Y | 6/2002 |
| CN | 1988859 A | 6/2007 |

(Continued)

OTHER PUBLICATIONS

Engage Modular Revision Hip System: Surgical Technique, 2007, DePuy Orthopaedics, Inc, 19 pages.

(Continued)

*Primary Examiner* — Si Ming Ku
(74) *Attorney, Agent, or Firm* — Barnes & Thornburg LLP

(57) ABSTRACT

A modular femoral prosthesis for use during performance of a hip revision procedure includes a proximal body component, a distal stem component, and a locking bolt. Surgical instruments and methods for use in implanting such a modular femoral prosthesis are disclosed.

19 Claims, 28 Drawing Sheets

Related U.S. Application Data

(60) Provisional application No. 61/472,500, filed on Apr. 6, 2011.

(51) Int. Cl.

| | | |
|---|---|---|
| *A61F 2/46* | (2006.01) | |
| *A61F 2/36* | (2006.01) | |
| *A61B 17/00* | (2006.01) | |
| *A61B 90/00* | (2016.01) | |

(52) U.S. Cl.
CPC .............. *A61F 2002/30235* (2013.01); *A61F 2002/30332* (2013.01); *A61F 2002/30507* (2013.01); *A61F 2002/30515* (2013.01); *A61F 2002/30616* (2013.01); *A61F 2002/30617* (2013.01); *A61F 2002/30738* (2013.01); *A61F 2002/3625* (2013.01); *A61F 2002/3652* (2013.01); *A61F 2002/3674* (2013.01); *A61F 2002/4622* (2013.01); *A61F 2002/4627* (2013.01); *A61F 2002/4629* (2013.01); *A61F 2002/4662* (2013.01); *A61F 2002/4668* (2013.01); *A61F 2002/4681* (2013.01)

(56) References Cited

U.S. PATENT DOCUMENTS

| | | |
|---|---|---|
| 1,029,402 A | 6/1912 | Ritter |
| 1,241,846 A | 10/1917 | Grons |
| 1,383,304 A | 7/1921 | Hughes et al. |
| 1,423,649 A | 7/1922 | Daniel |
| 1,534,692 A | 4/1925 | Davis |
| 1,661,682 A | 3/1928 | Scherner |
| 2,234,824 A | 3/1941 | Kingston |
| 2,248,054 A | 7/1941 | Becker |
| 2,487,331 A | 11/1949 | Greene |
| 2,631,584 A | 3/1953 | Purificato |
| 2,661,033 A | 12/1953 | Daniel |
| 2,711,196 A | 6/1955 | Daniel |
| 2,834,099 A | 5/1958 | Gasper |
| 2,834,382 A | 5/1958 | Daniel |
| 2,856,637 A | 10/1958 | Daniel |
| 2,864,282 A | 12/1958 | Daniel |
| 2,877,936 A | 3/1959 | David |
| 2,895,154 A | 7/1959 | Belcher |
| 2,902,596 A | 9/1959 | Rockwell et al. |
| 2,914,224 A | 11/1959 | Michel |
| 2,944,373 A | 7/1960 | Mentley et al. |
| 2,955,905 A | 10/1960 | Davies et al. |
| 2,957,610 A | 10/1960 | Michel |
| 2,974,699 A | 3/1961 | Boles et al. |
| 2,975,944 A | 3/1961 | Daniel |
| 2,977,726 A | 4/1961 | Daniel |
| 2,981,035 A | 4/1961 | Mentley et al. |
| 2,994,461 A | 8/1961 | Daniel |
| 2,994,988 A | 8/1961 | Mentley et al. |
| 3,048,307 A | 8/1962 | Daniel |
| 3,059,278 A | 10/1962 | Daniel |
| 3,071,862 A | 1/1963 | Daniel et al. |
| 3,077,877 A | 2/1963 | Daniel et al. |
| 3,092,934 A | 6/1963 | Daniel |
| 3,092,935 A | 6/1963 | Daniel |
| 3,101,875 A | 8/1963 | Daniel |
| 3,135,136 A | 6/1964 | Mentley et al. |
| 3,177,507 A | 4/1965 | Becker et al. |
| 3,180,532 A | 4/1965 | Daniel |
| 3,200,484 A | 8/1965 | Garman |
| 3,220,311 A | 11/1965 | Anthony et al. |
| 3,250,745 A | 5/1966 | Daniel et al. |
| 3,293,987 A | 12/1966 | Daniel |
| 3,300,833 A | 1/1967 | Daniel |
| 3,301,134 A | 1/1967 | Daniel |
| 3,319,526 A | 5/1967 | Daniel et al. |
| 3,331,115 A | 7/1967 | Daniel |
| 3,335,639 A | 8/1967 | Daniel |
| 3,424,783 A | 1/1969 | Harper et al. |
| 3,443,478 A | 5/1969 | Daniel |
| 3,451,111 A | 6/1969 | Daniel |
| 3,479,387 A | 11/1969 | Daniels et al. |
| 3,479,388 A | 11/1969 | Daniels |
| 3,483,175 A | 12/1969 | Daniels et al. |
| 3,494,752 A | 2/1970 | Daniel |
| 3,499,920 A | 3/1970 | Daniels |
| 3,541,868 A | 11/1970 | Hall |
| 3,580,027 A | 5/1971 | Daniel et al. |
| 3,580,029 A | 5/1971 | Daniel et al. |
| 3,604,235 A | 9/1971 | Motz et al. |
| 3,629,981 A | 12/1971 | McCaffery |
| 3,631,703 A | 1/1972 | Bregi et al. |
| 3,633,583 A | 1/1972 | Fishbein |
| 3,668,139 A | 6/1972 | Daniels et al. |
| 3,673,887 A | 7/1972 | Daniel et al. |
| 3,679,728 A | 7/1972 | Morgan et al. |
| 3,679,729 A | 7/1972 | Daniels |
| 3,691,718 A | 9/1972 | Woodruff |
| 3,700,957 A | 10/1972 | Daniels |
| 3,705,513 A | 12/1972 | Daniel |
| 3,749,365 A | 7/1973 | Van Gompel |
| 3,754,586 A | 8/1973 | Daniels |
| 3,810,312 A | 5/1974 | Carson |
| 3,849,322 A | 11/1974 | Wendler et al. |
| 3,862,483 A | 1/1975 | Kloster |
| 3,869,394 A | 3/1975 | Daniels et al. |
| 3,889,558 A | 6/1975 | Duncan |
| 3,912,727 A | 10/1975 | Daniels |
| 3,987,499 A | 10/1976 | Scharbach et al. |
| 4,004,581 A | 1/1977 | Heimke et al. |
| 4,009,712 A | 3/1977 | Burstein et al. |
| 4,035,988 A | 7/1977 | Daniels |
| 4,051,559 A | 10/1977 | Pifferi |
| D246,507 S | 11/1977 | Danielson |
| 4,115,875 A | 9/1978 | Rambert et al. |
| 4,116,200 A | 9/1978 | Braun et al. |
| 4,150,909 A | 4/1979 | Daniel et al. |
| D257,533 S | 11/1980 | Bevilacqua et al. |
| 4,242,758 A | 1/1981 | Amis et al. |
| D258,957 S | 4/1981 | Bevilacqua et al. |
| 4,305,394 A | 12/1981 | Bertuch |
| D266,768 S | 11/1982 | Bevilacqua et al. |
| D267,151 S | 12/1982 | Bruce et al. |
| 4,398,074 A | 8/1983 | Danielson et al. |
| 4,420,864 A | 12/1983 | Hoyt |
| 4,457,306 A | 7/1984 | Borzone |
| 4,458,420 A | 7/1984 | Davis |
| D275,006 S | 8/1984 | Danielson et al. |
| 4,473,070 A | 9/1984 | Matthews et al. |
| 4,538,886 A | 9/1985 | Townsend et al. |
| D282,246 S | 1/1986 | Thomas et al. |
| D282,350 S | 1/1986 | Thomas et al. |
| 4,601,289 A | 7/1986 | Chiarizzio et al. |
| D285,073 S | 8/1986 | Danielson et al. |
| D285,198 S | 8/1986 | Danielson et al. |
| 4,608,055 A | 8/1986 | Morrey et al. |
| D286,198 S | 10/1986 | Bancroft |
| D286,285 S | 10/1986 | Danielson et al. |
| D287,494 S | 12/1986 | Danielson et al. |
| D289,155 S | 4/1987 | Brooks et al. |
| 4,658,808 A | 4/1987 | Link |
| D290,399 S | 6/1987 | Kitchens |
| 4,670,015 A | 6/1987 | Freeman |
| 4,686,971 A | 8/1987 | Harris et al. |
| 4,686,978 A | 8/1987 | Wadsworth |
| 4,693,724 A | 9/1987 | Rhenter et al. |
| 4,710,946 A | 12/1987 | Hinch et al. |
| 4,716,894 A | 1/1988 | Lazzeri et al. |
| 4,738,256 A | 4/1988 | Freeman et al. |
| 4,777,942 A | 10/1988 | Frey et al. |
| 4,787,907 A | 11/1988 | Carignan |
| 4,830,147 A | 5/1989 | Kawada |
| D303,114 S | 8/1989 | Danielson et al. |
| D304,587 S | 11/1989 | Danielson et al. |
| 4,891,545 A | 1/1990 | Capek et al. |
| 4,917,530 A | 4/1990 | Engelhardt et al. |
| 4,923,422 A | 5/1990 | Capek et al. |

(56) References Cited

U.S. PATENT DOCUMENTS

| | | |
|---|---|---|
| 4,938,773 A | 7/1990 | Strand |
| 4,959,066 A | 9/1990 | Dunn et al. |
| 4,963,155 A | 10/1990 | Lazzeri et al. |
| 4,969,911 A | 11/1990 | Greene |
| D313,233 S | 12/1990 | Andrews, Sr. et al. |
| D315,343 S | 3/1991 | Andrews et al. |
| 4,997,621 A | 3/1991 | Johansson et al. |
| 5,002,578 A | 3/1991 | Luman |
| 5,002,581 A | 3/1991 | Paxson et al. |
| 5,015,255 A | 5/1991 | Kuslich |
| 5,016,858 A | 5/1991 | Mitchell |
| 5,020,519 A | 6/1991 | Hayes et al. |
| D318,051 S | 7/1991 | Danielson et al. |
| 5,033,180 A | 7/1991 | Colson |
| D319,439 S | 8/1991 | Danielson et al. |
| 5,047,033 A | 9/1991 | Fallin |
| 5,049,150 A | 9/1991 | Cozad |
| D320,985 S | 10/1991 | Danielson et al. |
| 5,053,037 A | 10/1991 | Lackey |
| 5,057,112 A | 10/1991 | Sherman et al. |
| 5,060,505 A | 10/1991 | Tury et al. |
| 5,061,271 A | 10/1991 | Van Zile |
| 5,080,685 A | 1/1992 | Bolesky et al. |
| D323,657 S | 2/1992 | Danielson et al. |
| 5,099,714 A | 3/1992 | Hutchison et al. |
| 5,100,407 A | 3/1992 | Conrad et al. |
| 5,108,452 A | 4/1992 | Demane et al. |
| 5,133,588 A | 7/1992 | Hutchinson et al. |
| 5,135,529 A | 8/1992 | Paxson et al. |
| 5,162,626 A | 11/1992 | Hutchison et al. |
| 5,171,055 A | 12/1992 | Hutchison et al. |
| 5,171,244 A | 12/1992 | Caspari et al. |
| 5,181,928 A | 1/1993 | Bolesky et al. |
| 5,184,017 A | 2/1993 | Tury et al. |
| 5,190,548 A | 3/1993 | Davis |
| 5,190,550 A | 3/1993 | Miller et al. |
| 5,192,283 A | 3/1993 | Ling et al. |
| 5,197,989 A | 3/1993 | Hinckfuss et al. |
| 5,201,882 A | 4/1993 | Paxson |
| 5,207,680 A | 5/1993 | Dietz et al. |
| 5,218,814 A | 6/1993 | Teal et al. |
| D337,639 S | 7/1993 | Beckman |
| 5,228,459 A | 7/1993 | Caspari et al. |
| D338,473 S | 8/1993 | Patterson et al. |
| 5,238,267 A | 8/1993 | Hutchison et al. |
| 5,247,171 A | 9/1993 | Wlodarczyk et al. |
| D340,461 S | 10/1993 | Patterson et al. |
| 5,263,498 A | 11/1993 | Caspari et al. |
| 5,290,313 A | 3/1994 | Heldreth |
| 5,304,181 A | 4/1994 | Caspari et al. |
| D346,979 S | 5/1994 | Stalcup et al. |
| 5,331,124 A | 7/1994 | Danielson |
| 5,336,226 A | 8/1994 | McDaniel et al. |
| 5,342,363 A | 8/1994 | Richelsoph |
| 5,342,366 A | 8/1994 | Whiteside et al. |
| 5,344,423 A | 9/1994 | Dietz et al. |
| 5,345,483 A | 9/1994 | Johansson et al. |
| 5,352,231 A | 10/1994 | Brumfield et al. |
| D352,521 S | 11/1994 | Sculler et al. |
| D353,394 S | 12/1994 | Stefanski et al. |
| 5,370,706 A | 12/1994 | Bolesky et al. |
| 5,372,209 A | 12/1994 | Raihert et al. |
| D355,186 S | 2/1995 | Danielson et al. |
| D355,187 S | 2/1995 | Danielson et al. |
| 5,387,218 A | 2/1995 | Meswania |
| 5,395,376 A | 3/1995 | Caspari et al. |
| D357,315 S | 4/1995 | Dietz |
| 5,403,320 A | 4/1995 | Luman et al. |
| 5,405,404 A | 4/1995 | Gardner et al. |
| 5,409,492 A | 4/1995 | Jones et al. |
| 5,415,659 A | 5/1995 | Lee et al. |
| 5,420,910 A | 5/1995 | Rudokas et al. |
| D359,064 S | 6/1995 | Sculler et al. |
| 5,422,478 A | 6/1995 | Wlodarczyk et al. |
| 5,457,100 A | 10/1995 | Daniel |
| 5,459,294 A | 10/1995 | Danielson |
| D364,621 S | 11/1995 | Clarke et al. |
| 5,468,243 A | 11/1995 | Halpern |
| 5,470,336 A | 11/1995 | Ling et al. |
| 5,474,559 A | 12/1995 | Bertin et al. |
| 5,476,466 A | 12/1995 | Barrette et al. |
| D365,824 S | 1/1996 | Danielson et al. |
| 5,486,180 A | 1/1996 | Dietz et al. |
| 5,496,324 A | 3/1996 | Barnes |
| 5,507,815 A | 4/1996 | Wagner et al. |
| 5,507,824 A | 4/1996 | Lennox |
| 5,507,830 A | 4/1996 | Demane et al. |
| 5,507,833 A | 4/1996 | Bohn |
| 5,519,929 A | 5/1996 | Bleckman |
| 5,527,316 A | 6/1996 | Stone et al. |
| 5,528,640 A | 6/1996 | Johansson et al. |
| 5,534,005 A | 7/1996 | Tokish et al. |
| 5,540,687 A | 7/1996 | Fairley et al. |
| 5,540,694 A | 7/1996 | Decarlo, Jr. et al. |
| 5,555,551 A | 9/1996 | Rudokas et al. |
| 5,569,255 A | 10/1996 | Burke |
| D376,527 S | 12/1996 | Apolinski et al. |
| 5,591,233 A | 1/1997 | Kelman et al. |
| 5,593,411 A | 1/1997 | Stalcup et al. |
| 5,593,452 A | 1/1997 | Higham et al. |
| 5,600,892 A | 2/1997 | Peugh et al. |
| 5,601,563 A | 2/1997 | Burke et al. |
| 5,601,567 A | 2/1997 | Swajger et al. |
| 5,607,269 A | 3/1997 | Dowd et al. |
| 5,607,431 A | 3/1997 | Dudasik et al. |
| D379,578 S | 6/1997 | Daniels |
| 5,643,271 A | 7/1997 | Sederholm et al. |
| 5,645,607 A | 7/1997 | Hickey |
| 5,653,714 A | 8/1997 | Dietz et al. |
| 5,653,764 A | 8/1997 | Murphy |
| 5,653,765 A | 8/1997 | McTighe et al. |
| 5,658,349 A | 8/1997 | Brooks et al. |
| 5,663,993 A | 9/1997 | Danielson et al. |
| 5,669,812 A | 9/1997 | Schockemoehl et al. |
| 5,683,395 A | 11/1997 | Mikhail |
| D387,962 S | 12/1997 | Apolinski et al. |
| D387,963 S | 12/1997 | Clark |
| 5,697,932 A | 12/1997 | Smith et al. |
| 5,702,480 A | 12/1997 | Kropf et al. |
| 5,702,487 A | 12/1997 | Averill et al. |
| 5,711,243 A | 1/1998 | Dunham |
| 5,715,672 A | 2/1998 | Schockemoehl et al. |
| D392,534 S | 3/1998 | Degen et al. |
| D392,866 S | 3/1998 | Degen et al. |
| 5,725,592 A | 3/1998 | White et al. |
| 5,728,128 A | 3/1998 | Crickenberger et al. |
| 5,735,857 A | 4/1998 | Lane |
| 5,743,915 A | 4/1998 | Bertin et al. |
| 5,752,972 A | 5/1998 | Hoogeboom |
| 5,755,803 A | 5/1998 | Haines et al. |
| 5,766,261 A | 6/1998 | Neal et al. |
| 5,769,855 A | 6/1998 | Bertin et al. |
| 5,776,200 A | 7/1998 | Johnson et al. |
| 5,782,921 A | 7/1998 | Colleran et al. |
| 5,792,143 A | 8/1998 | Samuelson et al. |
| 5,800,553 A | 9/1998 | Albrektsson et al. |
| 5,804,886 A | 9/1998 | Danielson et al. |
| 5,810,827 A | 9/1998 | Haines et al. |
| 5,810,829 A | 9/1998 | Elliott et al. |
| 5,810,830 A | 9/1998 | Noble et al. |
| 5,824,097 A | 10/1998 | Gabriel et al. |
| 5,849,015 A | 12/1998 | Haywood et al. |
| 5,850,162 A | 12/1998 | Danielsons |
| 5,853,415 A | 12/1998 | Bertin et al. |
| 5,858,020 A | 1/1999 | Johnson et al. |
| 5,858,828 A | 1/1999 | Seliskar et al. |
| 5,860,969 A | 1/1999 | White et al. |
| 5,860,981 A | 1/1999 | Bertin et al. |
| 5,876,459 A | 3/1999 | Powell |
| 5,879,354 A | 3/1999 | Haines et al. |
| 5,879,391 A | 3/1999 | Slamin |
| 5,890,966 A | 4/1999 | Costain et al. |
| 5,902,340 A | 5/1999 | White et al. |
| 5,906,644 A | 5/1999 | Powell |

(56) References Cited

U.S. PATENT DOCUMENTS

| | | |
|---|---|---|
| 5,908,423 A | 6/1999 | Kashuba et al. |
| 5,919,195 A | 7/1999 | Wilson et al. |
| 5,923,422 A | 7/1999 | Keens et al. |
| 5,935,172 A | 8/1999 | Ochoa et al. |
| 5,938,701 A | 8/1999 | Hiernard et al. |
| 5,941,706 A | 8/1999 | Ura |
| 5,950,121 A | 9/1999 | Kaminsky et al. |
| 5,951,606 A | 9/1999 | Burke |
| 5,954,460 A | 9/1999 | Degen et al. |
| 5,957,768 A | 9/1999 | Schockemoehl et al. |
| 5,957,925 A | 9/1999 | Cook et al. |
| 5,966,599 A | 10/1999 | Walker et al. |
| 5,968,049 A | 10/1999 | Da Rold |
| 5,973,064 A | 10/1999 | Zhao et al. |
| 5,976,145 A | 11/1999 | Kennefick |
| 5,976,147 A | 11/1999 | LaSalle et al. |
| 5,976,188 A | 11/1999 | Dextradeur et al. |
| 5,993,455 A | 11/1999 | Noble |
| 5,996,812 A | 12/1999 | Sokol |
| 5,997,419 A | 12/1999 | Daniels et al. |
| 6,013,082 A | 1/2000 | Hiernard et al. |
| 6,045,556 A | 4/2000 | Cohen |
| 6,048,365 A | 4/2000 | Burrows et al. |
| 6,054,895 A | 4/2000 | Danielsons et al. |
| 6,056,084 A | 5/2000 | Schockemoehl et al. |
| 6,056,754 A | 5/2000 | Haines et al. |
| 6,058,301 A | 5/2000 | Daniels |
| 6,059,528 A | 5/2000 | Danielson et al. |
| 6,063,123 A | 5/2000 | Burrows et al. |
| 6,069,048 A | 5/2000 | Daniel |
| 6,071,311 A | 6/2000 | O'Neil et al. |
| 6,077,783 A | 6/2000 | Allman et al. |
| 6,080,162 A | 6/2000 | Dye et al. |
| 6,090,146 A | 7/2000 | Rozow et al. |
| 6,096,625 A | 8/2000 | Daniel et al. |
| 6,110,179 A | 8/2000 | Flivik et al. |
| 6,117,138 A | 9/2000 | Burrows et al. |
| 6,120,507 A | 9/2000 | Allard et al. |
| 6,121,147 A | 9/2000 | Daniel et al. |
| 6,126,694 A | 10/2000 | Gray |
| 6,136,035 A | 10/2000 | Lob et al. |
| 6,139,581 A | 10/2000 | Engh et al. |
| 6,149,687 A | 11/2000 | Gray et al. |
| 6,159,214 A | 12/2000 | Michelson |
| 6,162,226 A | 12/2000 | DeCarlo, Jr. et al. |
| 6,165,177 A | 12/2000 | Wilson et al. |
| 6,179,116 B1 | 1/2001 | Noniewicz et al. |
| 6,179,877 B1 | 1/2001 | Burke |
| 6,181,925 B1 | 1/2001 | Kaminsky et al. |
| 6,185,416 B1 | 2/2001 | Rudokas et al. |
| 6,187,012 B1 | 2/2001 | Masini |
| 6,193,759 B1 | 2/2001 | Ro et al. |
| 6,197,064 B1 | 3/2001 | Haines et al. |
| 6,197,065 B1 | 3/2001 | Martin et al. |
| 6,201,253 B1 | 3/2001 | Allman et al. |
| 6,206,884 B1 | 3/2001 | Masini |
| 6,219,538 B1 | 4/2001 | Kaminsky et al. |
| 6,224,605 B1 | 5/2001 | Anderson et al. |
| 6,232,721 B1 | 5/2001 | Danielsons |
| 6,235,590 B1 | 5/2001 | Daniel et al. |
| 6,238,435 B1 | 5/2001 | Meulink et al. |
| 6,238,436 B1 | 5/2001 | Lob et al. |
| D443,882 S | 6/2001 | Daniels et al. |
| 6,241,847 B1 | 6/2001 | Allman et al. |
| 6,242,978 B1 | 6/2001 | Danielsons |
| 6,258,093 B1 | 7/2001 | Edwards et al. |
| 6,258,095 B1 | 7/2001 | Lombardo et al. |
| 6,258,097 B1 | 7/2001 | Cook et al. |
| 6,260,279 B1 | 7/2001 | Apolinski et al. |
| 6,263,998 B1 | 7/2001 | Schockemoehl et al. |
| 6,264,699 B1 | 7/2001 | Noiles et al. |
| 6,270,502 B1 | 8/2001 | Stulberg |
| 6,281,935 B1 | 8/2001 | Twitchell et al. |
| 6,285,871 B1 | 9/2001 | Daniels |
| 6,287,342 B1 | 9/2001 | Copf et al. |
| 6,310,410 B1 | 10/2001 | Lin et al. |
| D450,304 S | 11/2001 | Daniels et al. |
| 6,316,817 B1 | 11/2001 | Seliskar et al. |
| 6,318,651 B1 | 11/2001 | Spiering |
| 6,319,286 B1 | 11/2001 | Fernandez et al. |
| 6,330,845 B1 | 12/2001 | Meulink |
| 6,332,886 B1 | 12/2001 | Green et al. |
| 6,335,766 B1 | 1/2002 | Twitchell et al. |
| 6,354,908 B2 | 3/2002 | Allman et al. |
| 6,355,068 B1 | 3/2002 | Doubler et al. |
| 6,355,532 B1 | 3/2002 | Seliskar et al. |
| 6,361,563 B2 | 3/2002 | Terrill-Grisoni et al. |
| 6,366,422 B1 | 4/2002 | Daniel et al. |
| 6,372,520 B1 | 4/2002 | Hsia et al. |
| D457,176 S | 5/2002 | Daniels et al. |
| 6,382,276 B1 | 5/2002 | Daniels et al. |
| 6,395,004 B1 | 5/2002 | Dye et al. |
| D458,947 S | 6/2002 | Svetlik et al. |
| 6,400,415 B1 | 6/2002 | Danielsons |
| 6,406,217 B1 | 6/2002 | Daniel et al. |
| 6,419,147 B1 | 7/2002 | Daniel |
| 6,422,562 B1 | 7/2002 | Daniel |
| 6,422,816 B1 | 7/2002 | Danielson |
| 6,428,578 B2 | 8/2002 | White |
| 6,432,110 B1 | 8/2002 | Richelsoph |
| 6,432,141 B1 | 8/2002 | Stocks et al. |
| 6,440,139 B2 | 8/2002 | Michelson |
| D467,485 S | 12/2002 | Daniels et al. |
| 6,488,713 B1 | 12/2002 | Hershberger |
| 6,491,696 B1 | 12/2002 | Kunkel |
| D468,180 S | 1/2003 | Bruno et al. |
| 6,505,684 B2 | 1/2003 | Rayssiguier et al. |
| 6,508,841 B2 | 1/2003 | Martin et al. |
| D469,671 S | 2/2003 | Prell et al. |
| 6,517,581 B2 | 2/2003 | Blarney |
| RE38,058 E | 4/2003 | Fallin |
| 6,565,029 B2 | 5/2003 | Zweighaft et al. |
| 6,568,618 B1 | 5/2003 | Vanderheyden et al. |
| 6,589,284 B1 | 7/2003 | Silberer |
| 6,589,285 B2 | 7/2003 | Penenberg |
| 6,600,516 B1 | 7/2003 | Danielsons et al. |
| 6,609,900 B2 | 8/2003 | Lucke et al. |
| 6,613,091 B1 | 9/2003 | Zdeblick et al. |
| 6,663,616 B1 | 12/2003 | Roth et al. |
| 6,676,706 B1 | 1/2004 | Mears et al. |
| 6,679,917 B2 | 1/2004 | Ek |
| 6,682,568 B2 | 1/2004 | Despres et al. |
| 6,692,530 B2 | 2/2004 | Doubler et al. |
| 6,700,359 B2 | 3/2004 | Daniels et al. |
| 6,702,854 B1 | 3/2004 | Cheal et al. |
| 6,706,072 B2 | 3/2004 | Dwyer et al. |
| 6,706,621 B2 | 3/2004 | Cox et al. |
| 6,712,825 B2 | 3/2004 | Aebi et al. |
| 6,723,129 B2 | 4/2004 | Dwyer et al. |
| 6,740,090 B1 | 5/2004 | Cragg et al. |
| 6,743,235 B2 | 6/2004 | Subba Rao |
| 6,744,243 B2 | 6/2004 | Daniels et al. |
| 6,751,266 B2 | 6/2004 | Danielsons |
| 6,755,841 B2 | 6/2004 | Fraser et al. |
| 6,770,100 B2 | 8/2004 | Draenert |
| 6,793,208 B1 | 9/2004 | Riddle et al. |
| D497,499 S | 10/2004 | Daniel et al. |
| 6,811,376 B2 | 11/2004 | Arel et al. |
| 6,812,792 B2 | 11/2004 | Mattsson et al. |
| 6,824,552 B2 | 11/2004 | Robison et al. |
| 6,840,944 B2 | 1/2005 | Suddaby |
| 6,846,314 B2 | 1/2005 | Shapira |
| 6,856,029 B1 | 2/2005 | Daniel et al. |
| 6,870,160 B1 | 3/2005 | Daniel |
| 6,875,218 B2 | 4/2005 | Dye et al. |
| 6,883,217 B2 | 4/2005 | Barrette et al. |
| D505,611 S | 5/2005 | Daniel et al. |
| 6,905,515 B1 | 6/2005 | Gilbertson |
| 6,911,048 B2 | 6/2005 | Fernandez et al. |
| 6,949,101 B2 | 9/2005 | McCleary et al. |
| 6,990,691 B2 | 1/2006 | Klotz et al. |
| 6,997,930 B1 | 2/2006 | Jggi et al. |
| 7,001,392 B2 | 2/2006 | McGovern |
| 7,008,420 B2 | 3/2006 | Okada |

(56) References Cited

U.S. PATENT DOCUMENTS

| | | |
|---|---|---|
| 7,022,141 B2 | 4/2006 | Dwyer et al. |
| 7,066,042 B2 | 6/2006 | Andrews et al. |
| 7,074,224 B2 | 7/2006 | Daniels et al. |
| 7,188,556 B1 | 3/2007 | Rinner |
| 7,189,242 B2 | 3/2007 | Boyd et al. |
| 7,204,851 B2 | 4/2007 | Trieu et al. |
| 7,297,166 B2 | 11/2007 | Dwyer et al. |
| 7,363,838 B2 | 4/2008 | Abdelgany |
| 7,373,709 B2 | 5/2008 | Fernando et al. |
| 7,387,635 B2 | 6/2008 | Keller |
| 7,425,214 B1 | 9/2008 | McCarthy et al. |
| 7,431,723 B2 | 10/2008 | Hazebrouck |
| 7,582,092 B2 | 9/2009 | Jones et al. |
| 7,585,329 B2 | 9/2009 | McCleary et al. |
| 7,601,155 B2 | 10/2009 | Petersen |
| 7,641,658 B2 | 1/2010 | Shaolian et al. |
| 7,833,228 B1 | 11/2010 | Hershberger |
| 8,273,093 B2 | 9/2012 | Klotz et al. |
| 8,696,758 B2 | 4/2014 | Hood et al. |
| 8,702,807 B2 | 4/2014 | Hood et al. |
| 8,900,246 B2 | 12/2014 | Lashure et al. |
| 2001/0001121 A1 | 5/2001 | Lombardo et al. |
| 2001/0007957 A1 | 7/2001 | Martin et al. |
| 2001/0016779 A1 | 8/2001 | Lubinus |
| 2001/0021622 A1 | 9/2001 | Allman et al. |
| 2001/0034526 A1 | 10/2001 | Kuslich et al. |
| 2002/0004684 A1 | 1/2002 | Thomas et al. |
| 2002/0043296 A1 | 4/2002 | Daniels et al. |
| 2002/0052661 A1 | 5/2002 | Spotorno et al. |
| 2002/0058999 A1 | 5/2002 | Dwyer et al. |
| 2002/0059000 A1 | 5/2002 | Dwyer et al. |
| 2002/0127115 A1 | 9/2002 | Lucke et al. |
| 2002/0133233 A1 | 9/2002 | Blarney |
| 2002/0195512 A1 | 12/2002 | Zweighft et al. |
| 2003/0001551 A1 | 1/2003 | Daniels et al. |
| 2003/0048003 A1 | 3/2003 | Daniels et al. |
| 2003/0050645 A1 | 3/2003 | Parker et al. |
| 2003/0071329 A1 | 4/2003 | Cox et al. |
| 2003/0074080 A1 | 4/2003 | Murray |
| 2003/0095368 A1 | 5/2003 | Daniels et al. |
| 2003/0109882 A1 | 6/2003 | Shirado et al. |
| 2003/0114933 A1 | 6/2003 | Bouttens et al. |
| 2003/0130740 A1 | 7/2003 | Stocks et al. |
| 2003/0149487 A1 | 8/2003 | Doubler et al. |
| 2003/0171756 A1 | 9/2003 | Fallin et al. |
| 2003/0171816 A1 | 9/2003 | Scifert et al. |
| 2003/0180146 A1 | 9/2003 | Arel et al. |
| 2003/0187449 A1 | 10/2003 | McCleary et al. |
| 2003/0204269 A1 | 10/2003 | Gerbec et al. |
| 2003/0220698 A1 | 11/2003 | Mears et al. |
| 2003/0225417 A1 | 12/2003 | Fischell et al. |
| 2003/0228033 A1 | 12/2003 | Daniel et al. |
| 2003/0236523 A1 | 12/2003 | Johnson et al. |
| 2004/0010262 A1 | 1/2004 | Parkinson et al. |
| 2004/0010319 A1 | 1/2004 | McTighe et al. |
| 2004/0015239 A1 | 1/2004 | Beguec |
| 2004/0017085 A1 | 1/2004 | Daniels |
| 2004/0054373 A1 | 3/2004 | Serra et al. |
| 2004/0054419 A1 | 3/2004 | Serra et al. |
| 2004/0058997 A1 | 3/2004 | Daniel |
| 2004/0064186 A1 | 4/2004 | McCleary et al. |
| 2004/0066217 A1 | 4/2004 | Daniels et al. |
| 2004/0073315 A1 | 4/2004 | Justin et al. |
| 2004/0092951 A1 | 5/2004 | Serra et al. |
| 2004/0111861 A1 | 6/2004 | Barrette et al. |
| 2004/0122437 A1 | 6/2004 | Dwyer et al. |
| 2004/0122439 A1 | 6/2004 | Dwyer et al. |
| 2004/0122440 A1 | 6/2004 | Daniels et al. |
| 2004/0122525 A1 | 6/2004 | Daniels et al. |
| 2004/0130394 A1 | 7/2004 | Mattsson et al. |
| 2004/0135233 A1 | 7/2004 | Cox et al. |
| 2004/0167527 A1 | 8/2004 | Simon et al. |
| 2004/0172138 A1 | 9/2004 | May et al. |
| 2004/0172139 A1 | 9/2004 | Dwyer et al. |
| 2004/0210471 A1 | 10/2004 | Luby et al. |
| 2004/0211046 A1 | 10/2004 | Tally et al. |
| 2004/0236342 A1 | 11/2004 | Ferree et al. |
| 2004/0260297 A1 | 12/2004 | Padget et al. |
| 2004/0267266 A1 | 12/2004 | Daniels et al. |
| 2004/0267267 A1* | 12/2004 | Daniels ............. A61F 2/3662 606/80 |
| 2004/0267372 A1 | 12/2004 | Vanasse et al. |
| 2004/0267373 A1 | 12/2004 | Dwyer et al. |
| 2005/0004679 A1 | 1/2005 | Sederholm et al. |
| 2005/0010992 A1 | 1/2005 | Klotz et al. |
| 2005/0015049 A1 | 1/2005 | Rioux et al. |
| 2005/0033444 A1 | 2/2005 | Jones et al. |
| 2005/0047239 A1 | 3/2005 | Takahashi et al. |
| 2005/0078289 A1 | 4/2005 | Daniel et al. |
| 2005/0081910 A1 | 4/2005 | Danielson et al. |
| 2005/0085820 A1 | 4/2005 | Collins et al. |
| 2005/0115391 A1 | 6/2005 | Baker et al. |
| 2005/0154331 A1 | 7/2005 | Christie et al. |
| 2005/0188878 A1 | 9/2005 | Baker et al. |
| 2005/0209597 A1 | 9/2005 | Long et al. |
| 2005/0222572 A1 | 10/2005 | Chana |
| 2005/0234461 A1 | 10/2005 | Burdulis et al. |
| 2005/0234462 A1 | 10/2005 | Hershberger |
| 2005/0234463 A1 | 10/2005 | Hershberger et al. |
| 2005/0234559 A1 | 10/2005 | Fernandez et al. |
| 2005/0240193 A1 | 10/2005 | Layne et al. |
| 2005/0261702 A1 | 11/2005 | Oribe et al. |
| 2005/0267937 A1 | 12/2005 | Daniels et al. |
| 2005/0288676 A1 | 12/2005 | Schnieders et al. |
| 2006/0015110 A1 | 1/2006 | Pepper |
| 2006/0015112 A1 | 1/2006 | McGovern |
| 2006/0024656 A1 | 2/2006 | Morris et al. |
| 2006/0027027 A1 | 2/2006 | Serra et al. |
| 2006/0058810 A1 | 3/2006 | Wozencroft et al. |
| 2006/0106393 A1 | 5/2006 | Huebner et al. |
| 2006/0217737 A1 | 9/2006 | Iversen |
| 2006/0260440 A1 | 11/2006 | Abdelgany |
| 2006/0281048 A1 | 12/2006 | Bailey et al. |
| 2007/0005144 A1 | 1/2007 | Leisinger et al. |
| 2007/0043376 A1 | 2/2007 | Leatherbury et al. |
| 2007/0100464 A1 | 5/2007 | Meulink |
| 2007/0123908 A1 | 5/2007 | Jones et al. |
| 2007/0162033 A1 | 7/2007 | Daniels et al. |
| 2007/0179502 A1 | 8/2007 | Raynor et al. |
| 2007/0233132 A1 | 10/2007 | Valla |
| 2007/0244566 A1 | 10/2007 | Daniels et al. |
| 2007/0260315 A1 | 11/2007 | Foley et al. |
| 2007/0299534 A1 | 12/2007 | Lewis et al. |
| 2008/0065081 A1 | 3/2008 | Lechot et al. |
| 2008/0077156 A1 | 3/2008 | Emstad |
| 2008/0091212 A1 | 4/2008 | Dwyer et al. |
| 2008/0114367 A1 | 5/2008 | Meyer |
| 2008/0125867 A1 | 5/2008 | McCleary et al. |
| 2008/0133024 A1 | 6/2008 | Meswania |
| 2008/0140211 A1 | 6/2008 | Doubler et al. |
| 2008/0161811 A1* | 7/2008 | Daniels ............. A61F 2/36 606/80 |
| 2008/0188878 A1 | 8/2008 | Young |
| 2008/0275457 A1 | 11/2008 | Meek et al. |
| 2009/0112216 A1 | 4/2009 | Leisinger |
| 2009/0112218 A1 | 4/2009 | McCleary et al. |
| 2009/0187251 A1 | 7/2009 | Justin et al. |
| 2009/0228012 A1 | 9/2009 | Gangji et al. |
| 2009/0307887 A1 | 12/2009 | Jones et al. |
| 2010/0069909 A1 | 3/2010 | Taylor |
| 2010/0107829 A1 | 5/2010 | Zimmerman et al. |
| 2010/0145345 A1 | 6/2010 | Ammann et al. |
| 2010/0168752 A1 | 7/2010 | Edwards |
| 2010/0249943 A1 | 9/2010 | Bergin et al. |
| 2011/0054550 A1 | 3/2011 | Metzinger et al. |
| 2011/0054628 A1 | 3/2011 | Banks et al. |
| 2011/0071527 A1 | 3/2011 | Nelson et al. |
| 2011/0118743 A1 | 5/2011 | Cannell et al. |
| 2011/0302760 A1 | 12/2011 | Leisinger et al. |
| 2012/0053698 A1 | 3/2012 | Huff et al. |
| 2012/0259338 A1 | 10/2012 | Carr et al. |
| 2012/0259339 A1 | 10/2012 | Hood et al. |
| 2012/0259341 A1 | 10/2012 | McCleary et al. |

(56) References Cited

U.S. PATENT DOCUMENTS

| | | | |
|---|---|---|---|
| 2012/0259421 A1 | 10/2012 | Satterthwaite et al. | |
| 2014/0214172 A1 | 7/2014 | Hood et al. | |
| 2015/0105831 A1* | 4/2015 | Yim | A61B 17/7091 606/86 A |

FOREIGN PATENT DOCUMENTS

| | | |
|---|---|---|
| CN | 2930657 Y | 8/2007 |
| CN | 200948178 Y | 9/2007 |
| CN | 101478933 A | 7/2009 |
| CN | 101664342 A | 3/2010 |
| CN | 201510379 U | 6/2010 |
| DE | 1001440 B | 1/1957 |
| DE | 2823406 A1 | 12/1978 |
| DE | 3023942 A1 | 1/1982 |
| DE | 3538654 A1 | 4/1987 |
| DE | 20114835 U1 | 1/2002 |
| DE | 202006000845 U1 | 5/2006 |
| DE | 202012102017 U1 | 10/2013 |
| EP | 206777 A2 | 12/1986 |
| EP | 239711 A1 | 10/1987 |
| EP | 333990 A2 | 9/1989 |
| EP | 511244 A1 | 11/1992 |
| EP | 567349 A1 | 10/1993 |
| EP | 595956 A1 | 5/1994 |
| EP | 661023 A2 | 7/1995 |
| EP | 726063 A1 | 8/1996 |
| EP | 728449 A2 | 8/1996 |
| EP | 842639 A2 | 5/1998 |
| EP | 861635 A2 | 9/1998 |
| EP | 1000595 A1 | 5/2000 |
| EP | 1013245 A2 | 6/2000 |
| EP | 1025816 A1 | 8/2000 |
| EP | 1080701 A2 | 3/2001 |
| EP | 1084680 A2 | 3/2001 |
| EP | 1191906 A1 | 4/2002 |
| EP | 1201191 A1 | 5/2002 |
| EP | 1263334 A1 | 12/2002 |
| EP | 1323395 A2 | 7/2003 |
| EP | 1348384 A2 | 10/2003 |
| EP | 1369089 A2 | 12/2003 |
| EP | 1435223 A1 | 7/2004 |
| EP | 1493407 A2 | 1/2005 |
| EP | 1522284 A2 | 4/2005 |
| EP | 1591084 A1 | 11/2005 |
| EP | 1738723 A1 | 1/2007 |
| EP | 1905396 A1 | 4/2008 |
| EP | 2055273 A1 | 5/2009 |
| EP | 2057969 A2 | 5/2009 |
| FR | 2606628 A1 | 5/1988 |
| FR | 2699400 A1 | 6/1994 |
| FR | 2737107 A1 | 1/1997 |
| FR | 2828397 A1 | 2/2003 |
| FR | 2832624 A1 | 5/2003 |
| FR | 2926208 A1 | 7/2009 |
| FR | 2926212 A1 | 7/2009 |
| GB | 2250441 A | 6/1992 |
| JP | 06500039 A | 1/1994 |
| JP | 10080095 A | 3/1998 |
| JP | 2000210314 A | 8/2000 |
| JP | 2000217851 A | 8/2000 |
| JP | 2002153479 A | 5/2002 |
| JP | 2002238912 A | 8/2002 |
| JP | 2003339724 A | 12/2003 |
| JP | 2004501716 A | 1/2004 |
| JP | 2004515310 A | 5/2004 |
| JP | 2004202234 A | 7/2004 |
| JP | 2004223261 A | 8/2004 |
| JP | 2004251450 A | 9/2004 |
| JP | 2006501917 A | 1/2006 |
| JP | 2006523106 A | 10/2006 |
| JP | 2007061154 A | 3/2007 |
| JP | 2007503911 A | 3/2007 |
| JP | 2007508063 A | 4/2007 |
| JP | 2009518077 A | 5/2009 |
| JP | 2009529379 A | 8/2009 |
| JP | 2010540179 A | 12/2010 |
| JP | 5148516 B2 | 2/2013 |
| JP | 5212069 B2 | 6/2013 |
| WO | 9110408 A1 | 7/1991 |
| WO | 9210138 A1 | 6/1992 |
| WO | 9301769 A1 | 2/1993 |
| WO | 9412123 A1 | 6/1994 |
| WO | 9427507 A1 | 12/1994 |
| WO | 9615738 A1 | 5/1996 |
| WO | 9615739 A1 | 5/1996 |
| WO | 9920195 A1 | 4/1999 |
| WO | 9920196 A1 | 4/1999 |
| WO | 0167997 A1 | 9/2001 |
| WO | 02102254 A2 | 12/2002 |
| WO | 03015642 A1 | 2/2003 |
| WO | 03065906 A2 | 8/2003 |
| WO | 03082159 A1 | 10/2003 |
| WO | 03092513 A1 | 11/2003 |
| WO | 03094698 A2 | 11/2003 |
| WO | 03094803 A1 | 11/2003 |
| WO | 2004028266 A1 | 4/2004 |
| WO | 2004032767 A1 | 4/2004 |
| WO | 2004089224 A2 | 10/2004 |
| WO | 2005034817 A1 | 4/2005 |
| WO | 2006078511 A1 | 7/2006 |
| WO | 2007026119 A1 | 3/2007 |
| WO | 2007098549 A1 | 9/2007 |
| WO | 2007106752 A2 | 9/2007 |
| WO | 2008069800 A1 | 6/2008 |
| WO | 2009024798 A1 | 2/2009 |
| WO | 2012138824 A2 | 10/2012 |

OTHER PUBLICATIONS

Gray, John R., ;Clinically-Oriented Geometry of the Femur;, A thesis submitted to the School of Physical & Health Education in partial fulfillment of requirements for the degree of Master of Science, Queen's University, Kingston, Ontario, Canada, Aug. 1995, 73 pages.

Zimmer, ;Metasul LDH Large Diameter Head,; Surgical Technique Enhancing Stability and Increasing Range of Motion, available at least as early as Sep. 28, 2006 (19 pages).

Depuy Orthopaedics, Inc., "S-Rom Modular Hip System, Minimally Invasive Calcar Miller Surgical Technique," 0612-04-503, 2004, Depuy Orthopaedics, Inc.

Paul, H.A., et al. "Development of a Surgical Robot for Cementless Total Hip Arthroplasty," Clinical Orthopedics & Related Research 285 Dec. 1992: 57-66.

Zimmer Fracture Equipment & Orthopaedic Appliances, 1 page, published at least as early as Sep. 29, 2005.

Japanese Office Action for Japanese Application No. 2019-190013, dated Oct. 27, 2020, 2 pages.

* cited by examiner

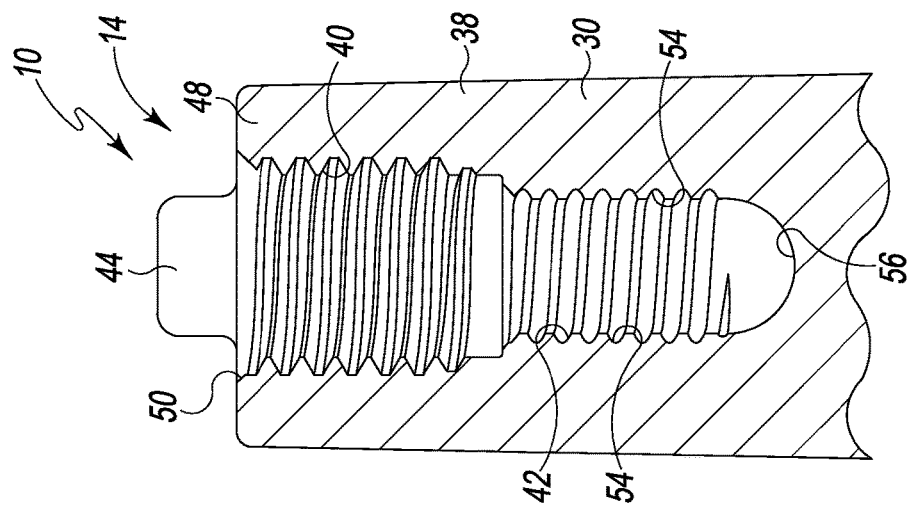
Fig. 6
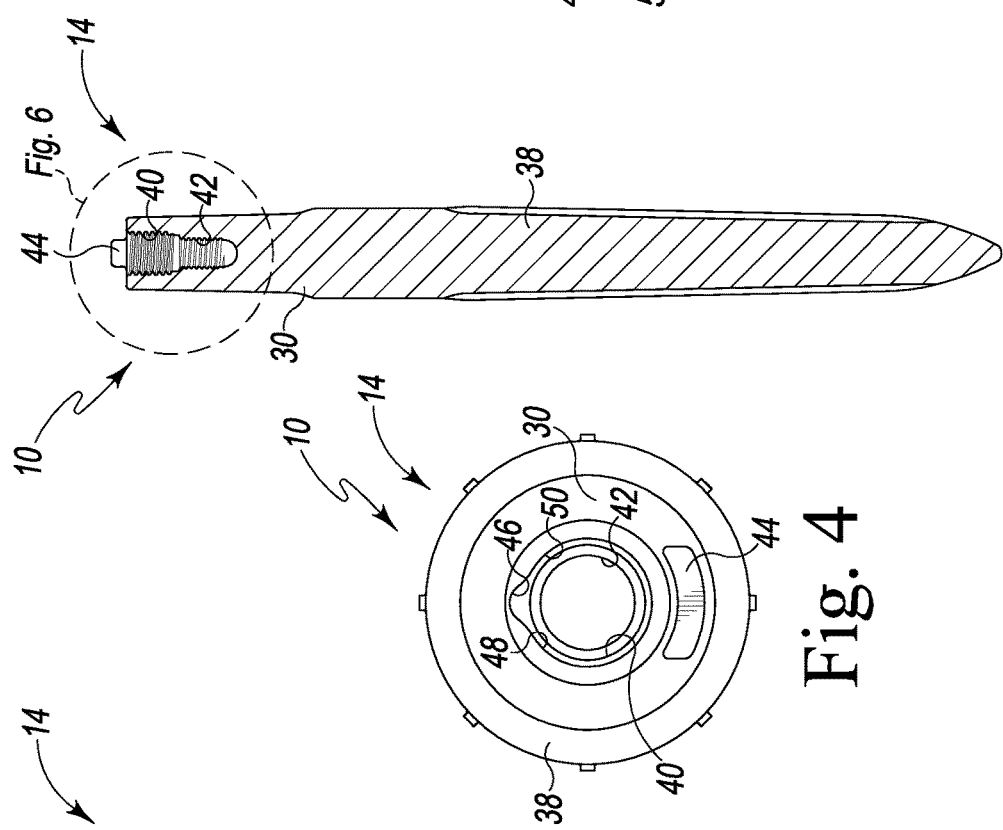
Fig. 5
Fig. 4
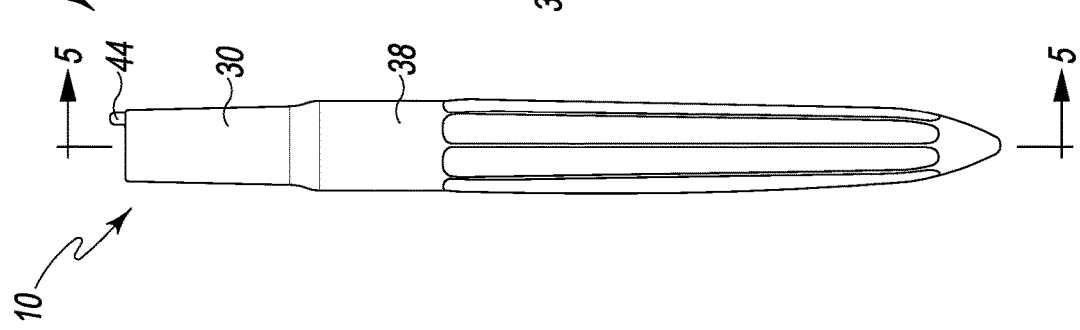
Fig. 3

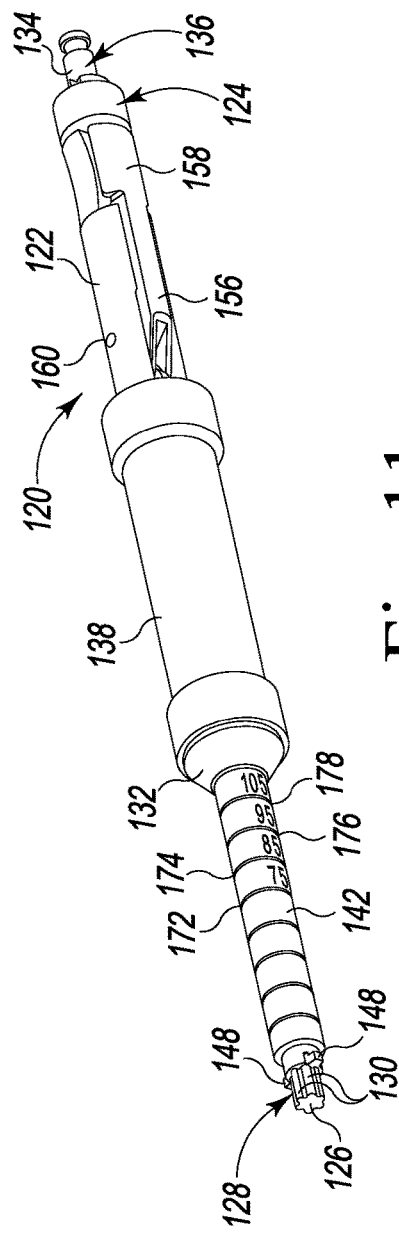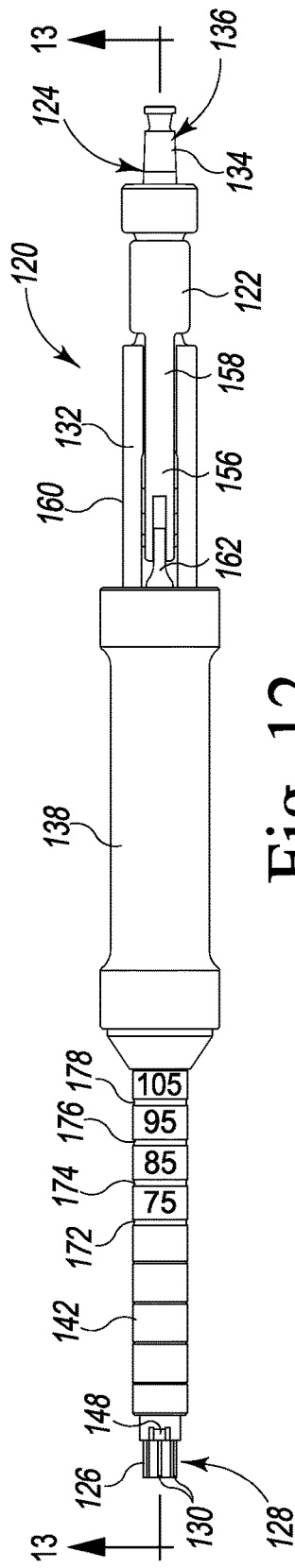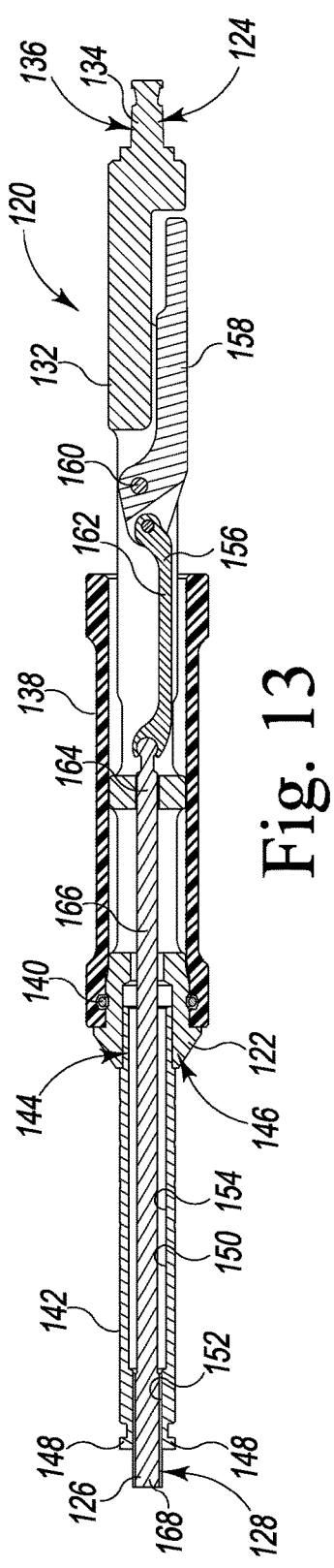

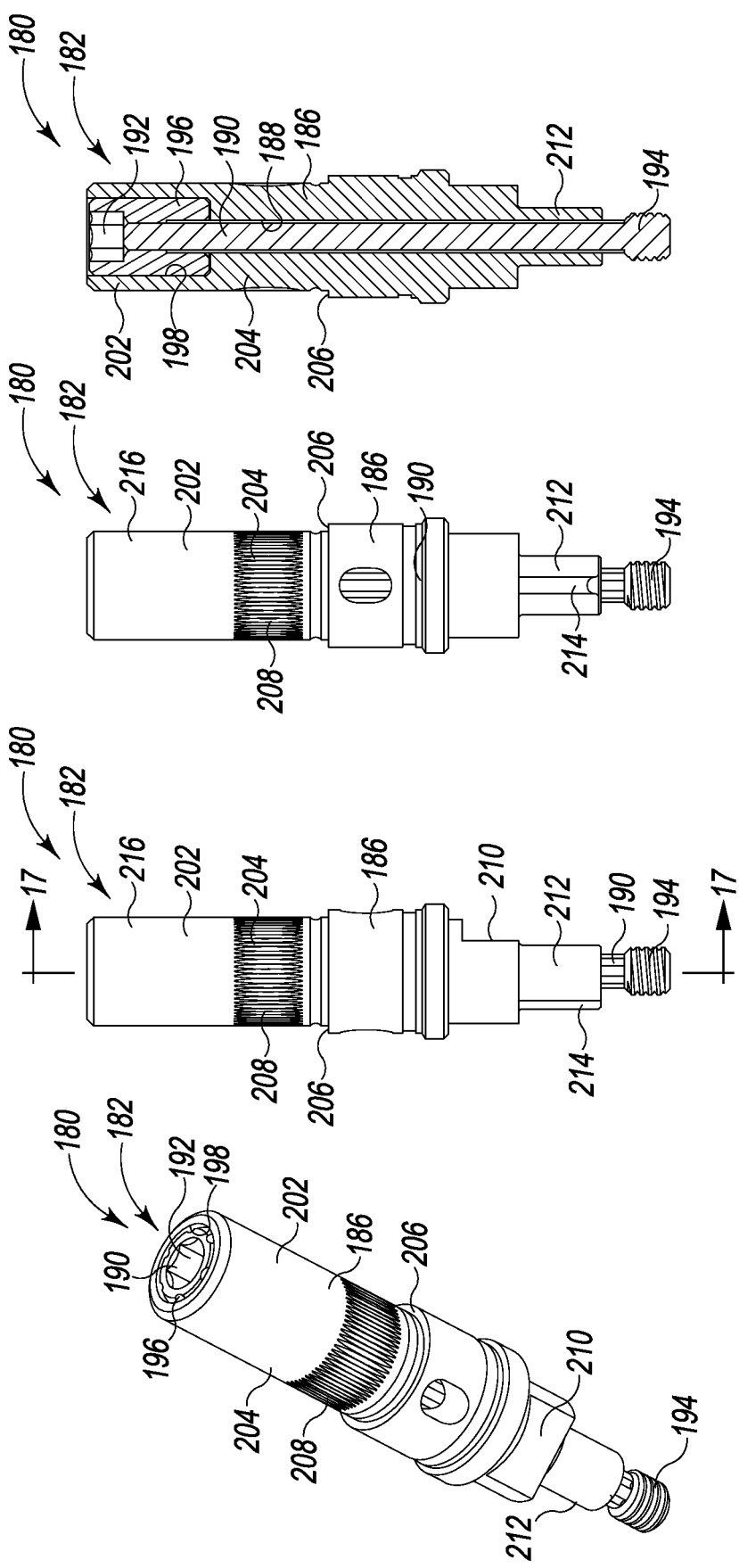

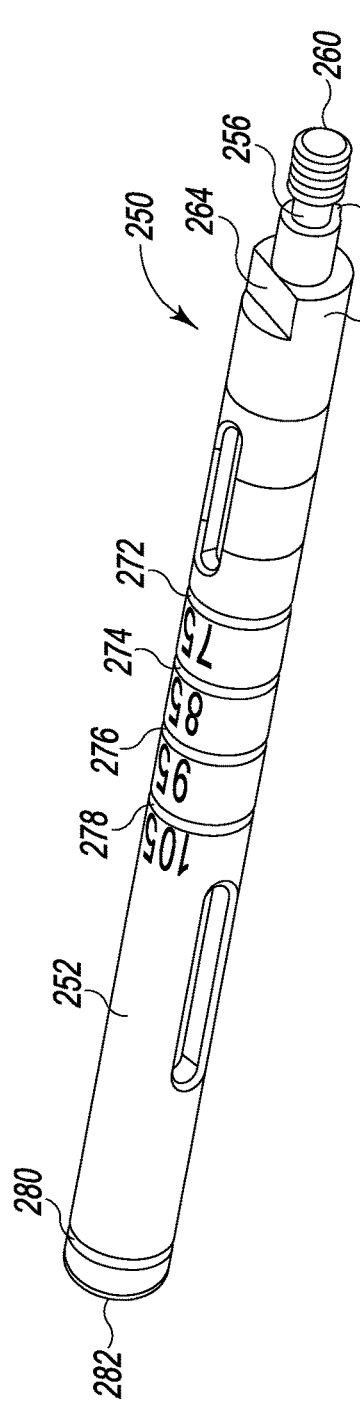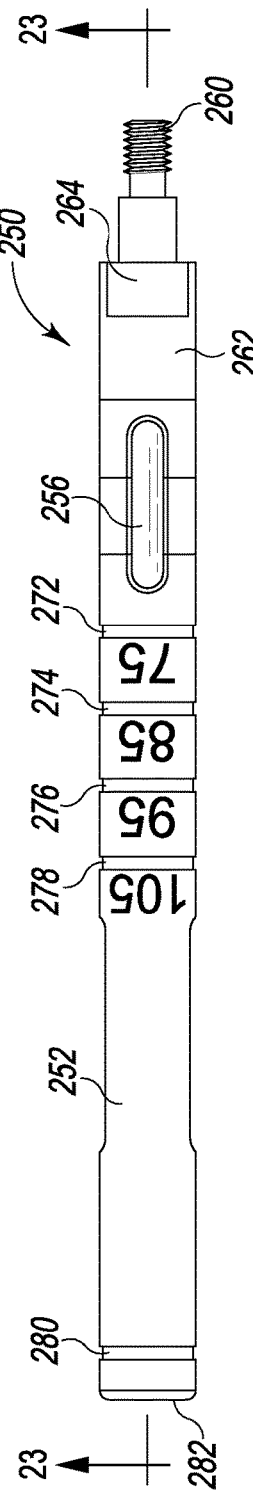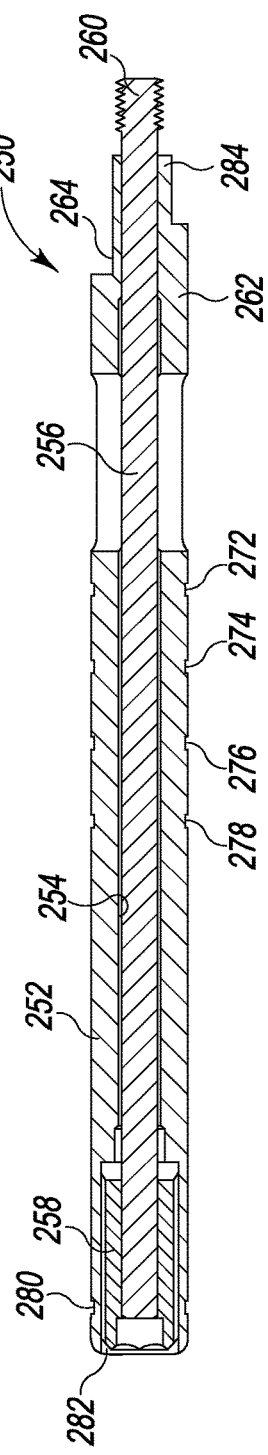

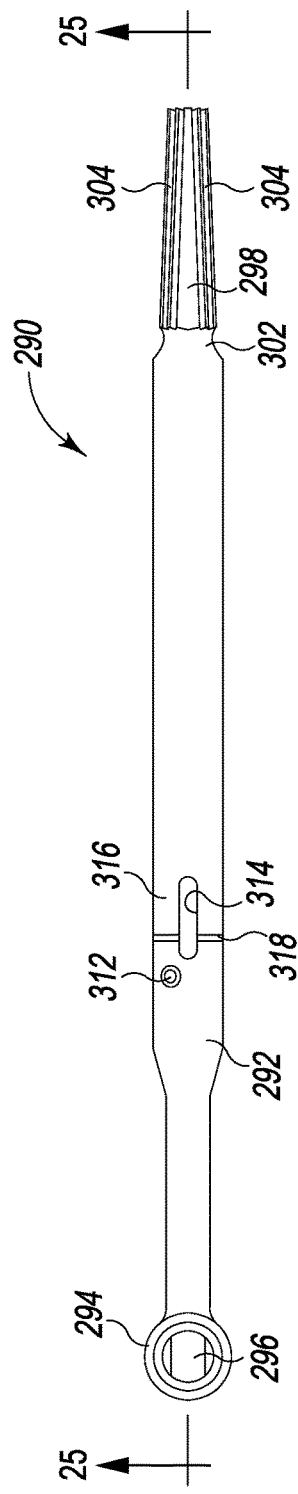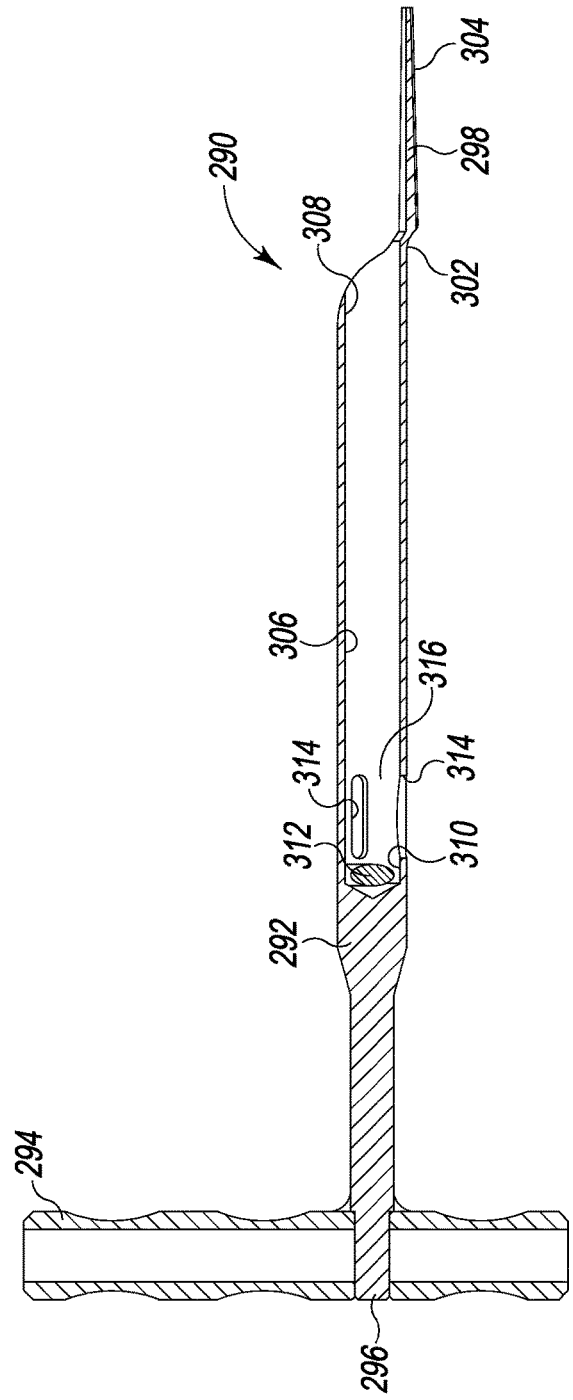
Fig. 24
Fig. 25

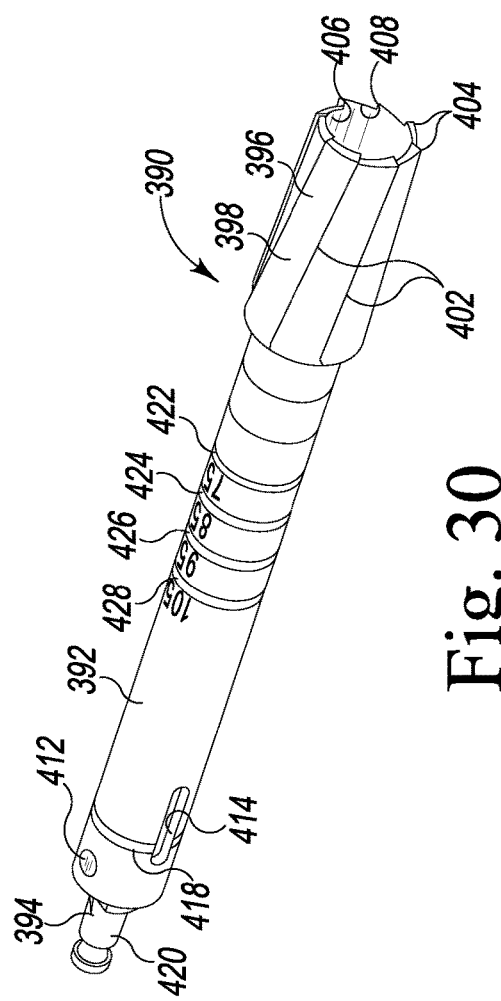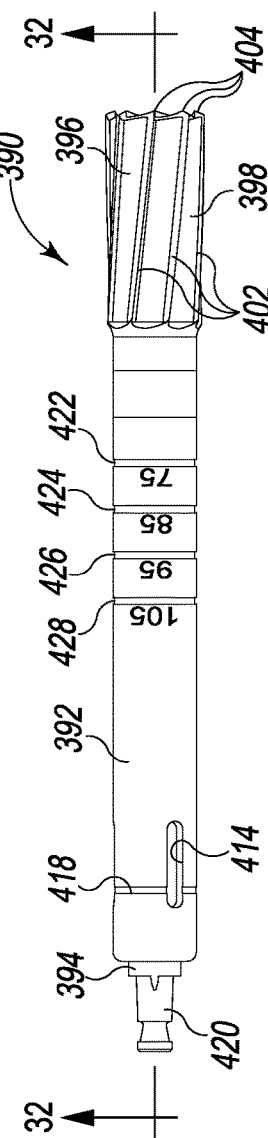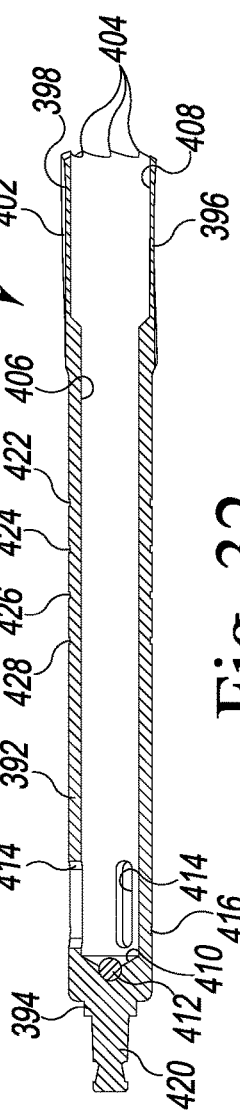
Fig. 30
Fig. 31
Fig. 32

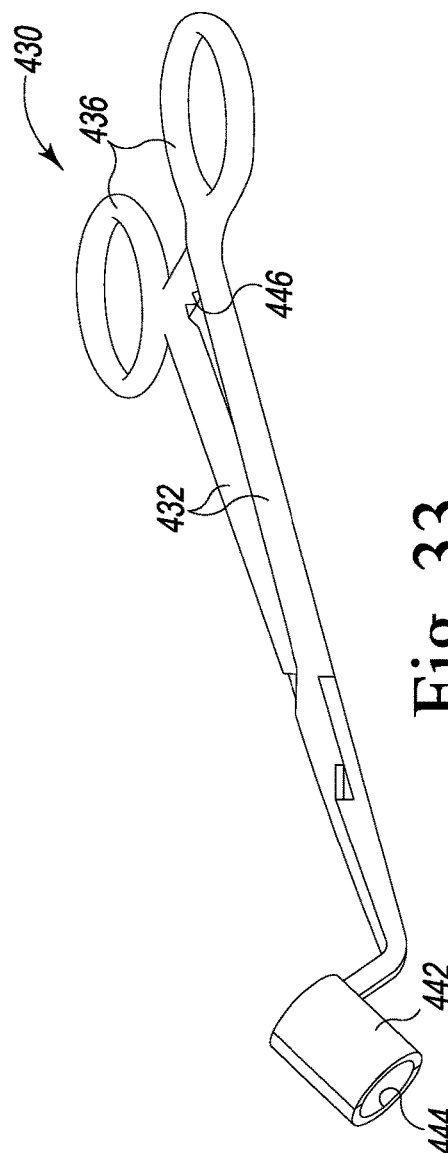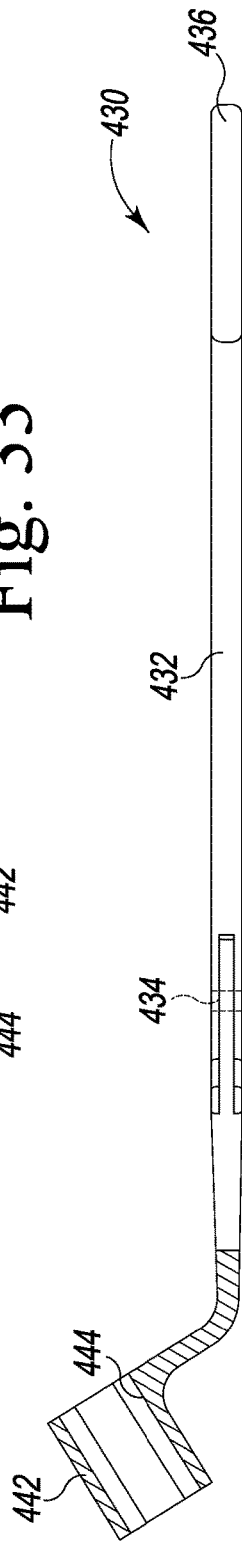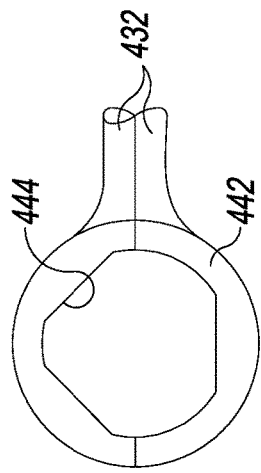
Fig. 33
Fig. 34
Fig. 35

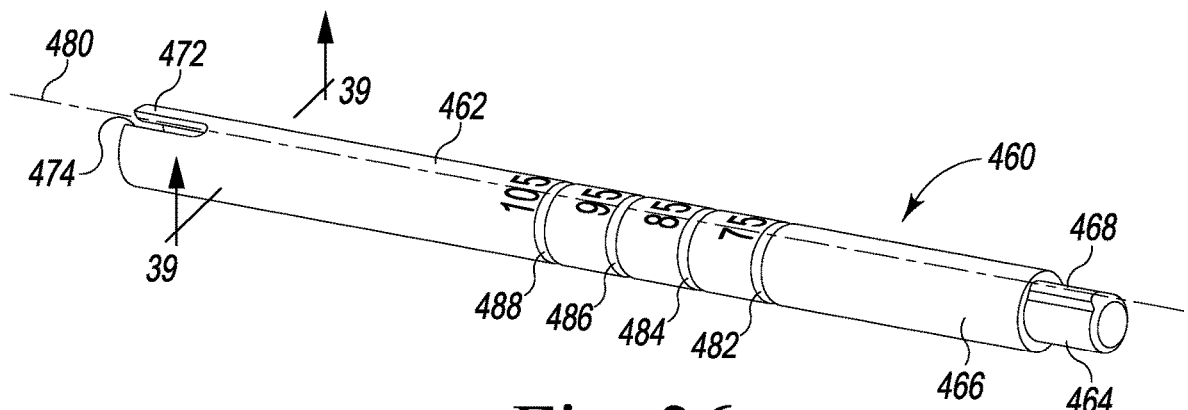
Fig. 36
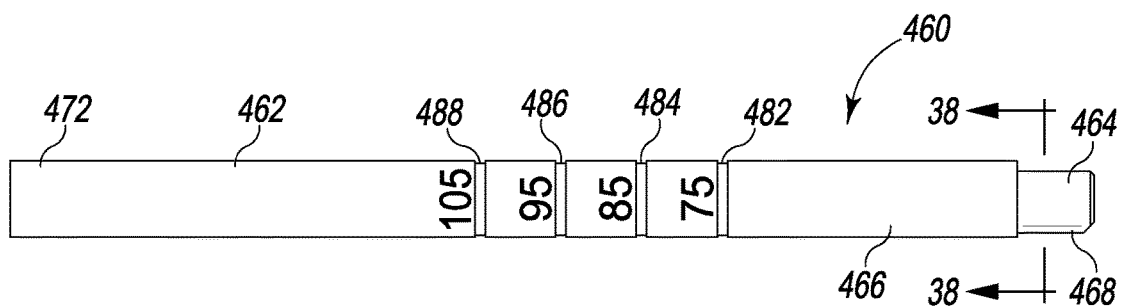
Fig. 37
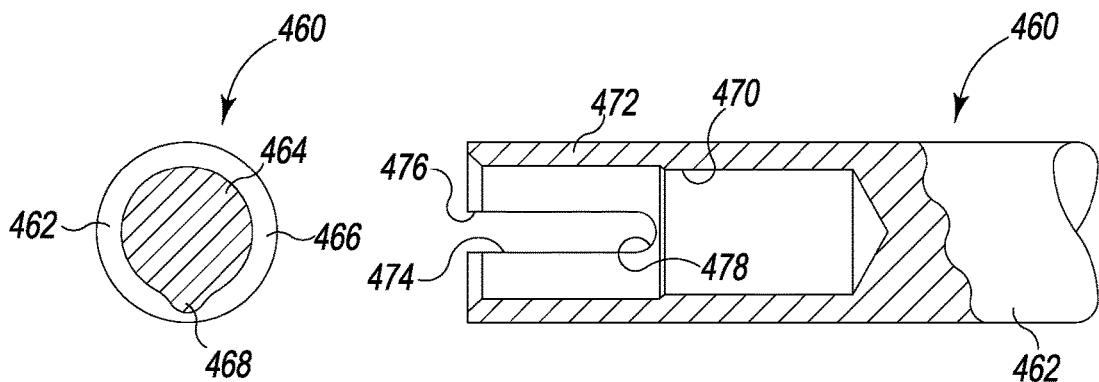
Fig. 38
Fig. 39

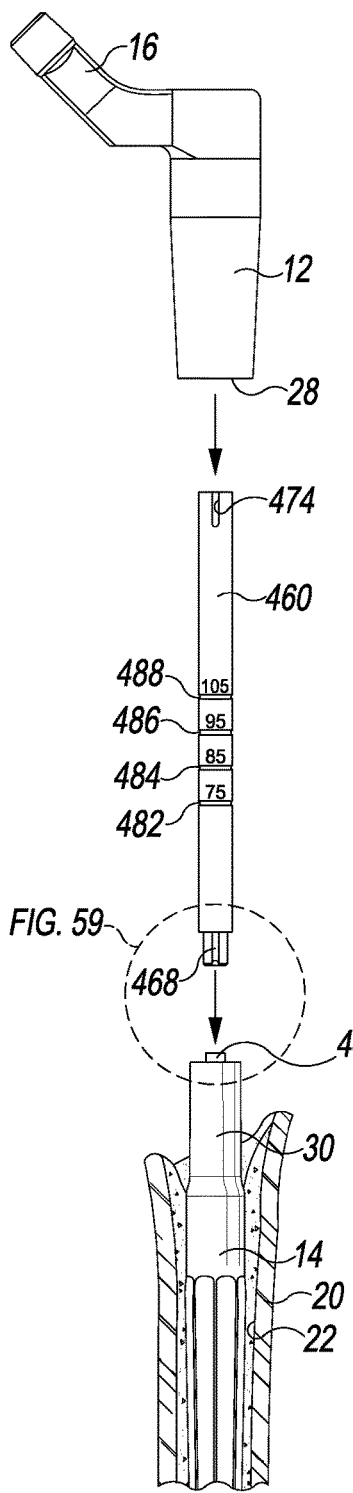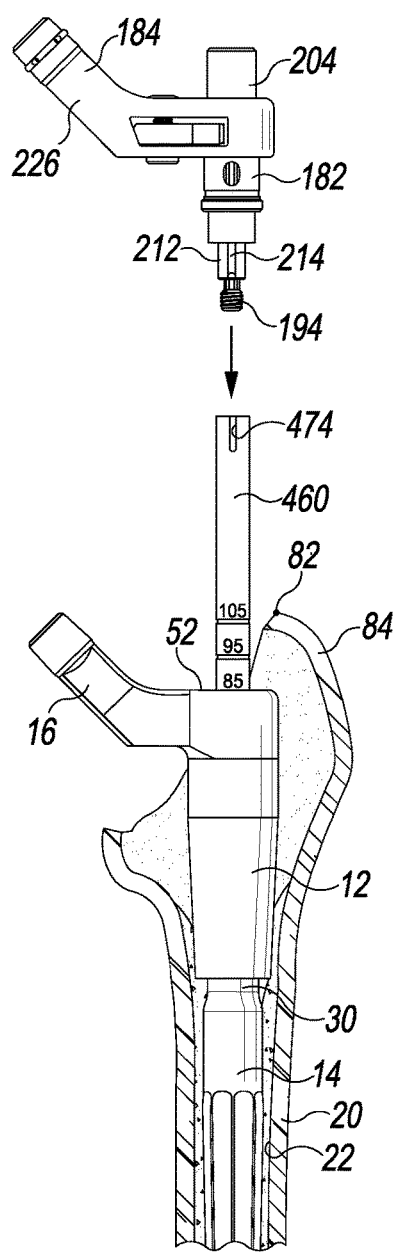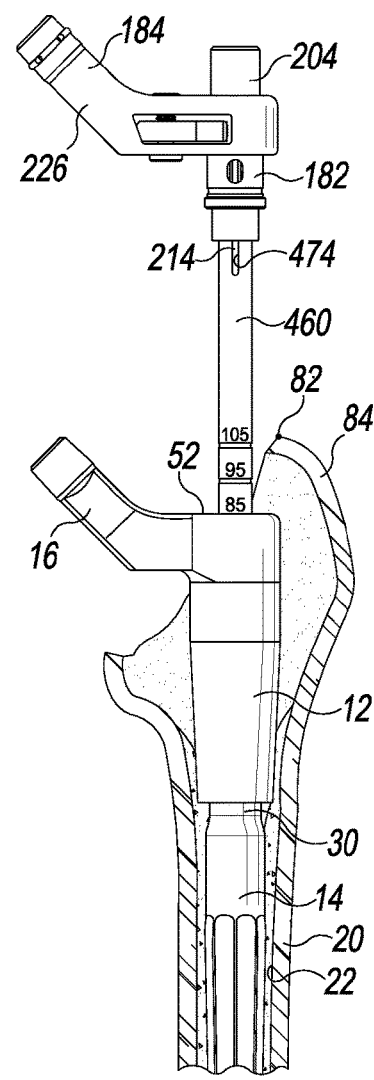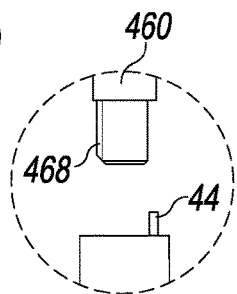
Fig. 58
Fig. 60
Fig. 61
Fig. 59

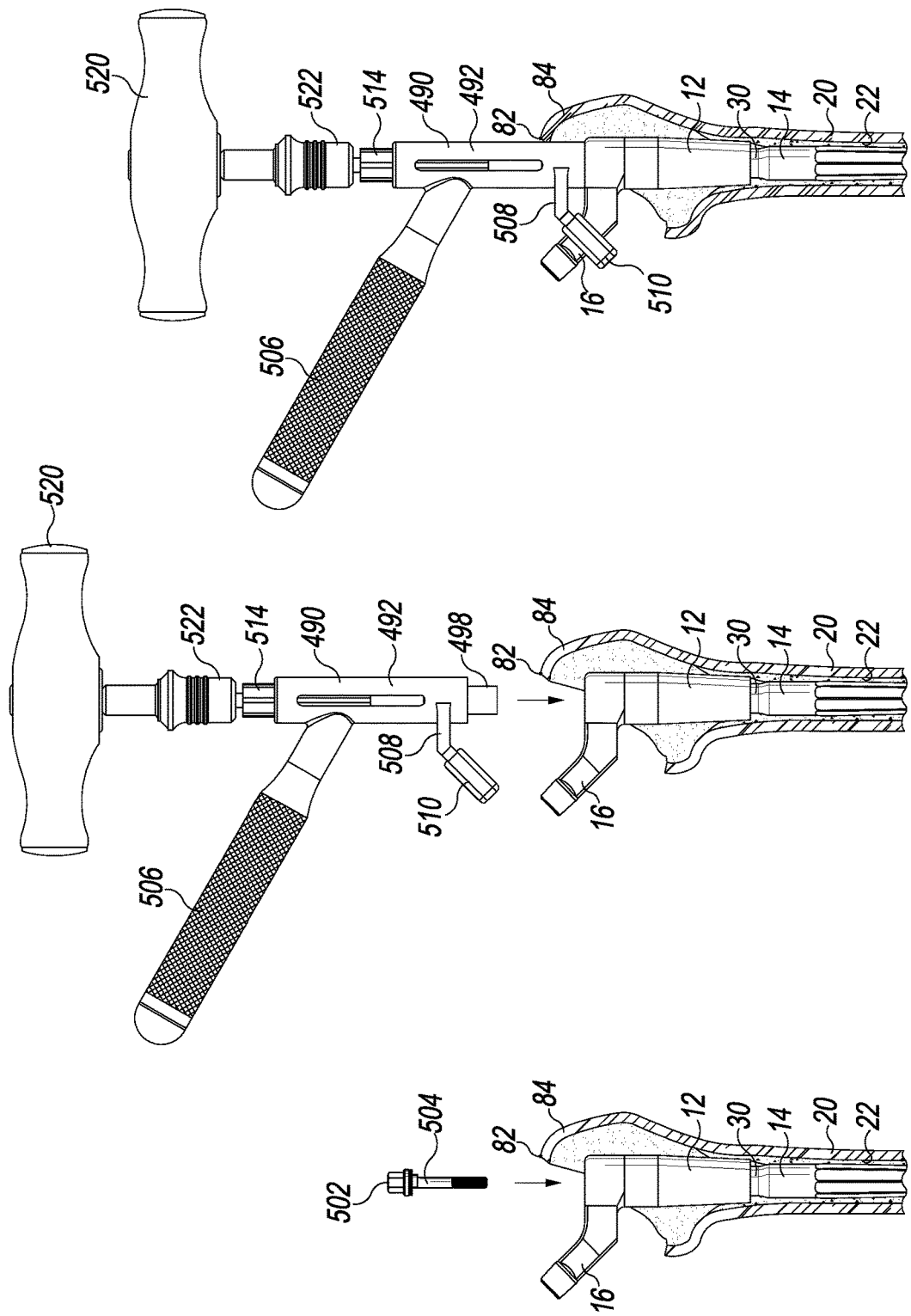

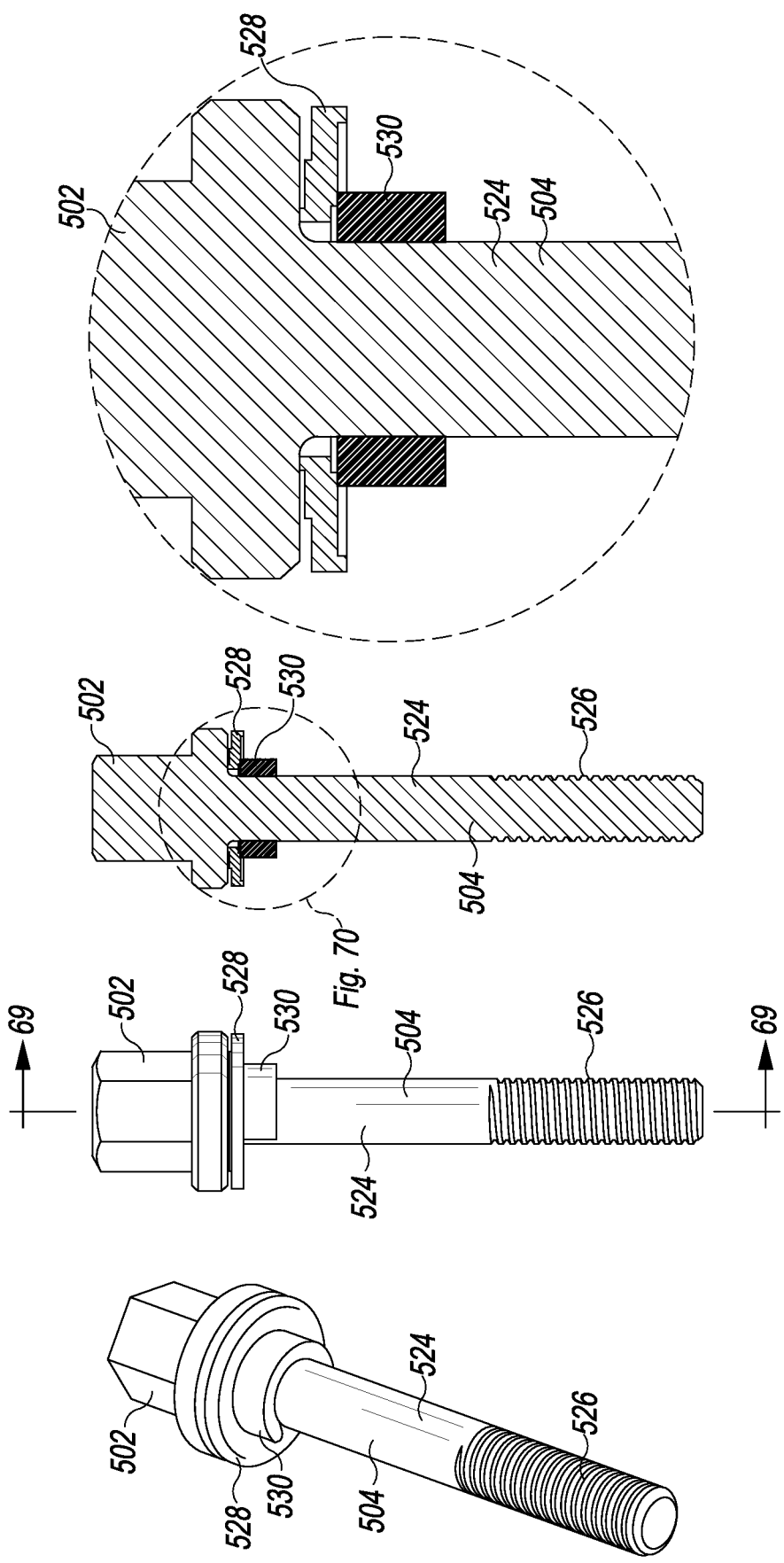

DISTAL REAMER FOR USE DURING AN ORTHOPAEDIC SURGICAL PROCEDURE TO IMPLANT A REVISION HIP PROSTHESIS

This application is a divisional application of U.S. patent application Ser. No. 13/440,406, which was on Apr. 5, 2012 and claimed priority under 35 U.S.C. § 119(e) to U.S. Provisional Patent Application Ser. No. 61/472,500 which was filed on Apr. 6, 2011. The entireties of those applications are hereby incorporated by reference.

CROSS REFERENCE

Cross reference is made to U.S. patent application Ser. No. 13/440,397, which issued as U.S. Pat. No. 8,702,807 and is entitled "REVISION HIP PROSTHESIS HAVING AN IMPLANTABLE DISTAL STEM COMPONENT;"- U.S. patent application Ser. No. 13/440,425, which issued as U.S. Pat. No. 8,900,246 entitled "PROXIMAL TRIAL INSTRUMENT FOR USE DURING AN ORTHOPAEDIC SURGICAL PROCEDURE TO IMPLANT A REVISION HIP PROSTHESIS;" U.S. patent application Ser. No. 13/440,430, which issued as U.S. Pat. No. 9,949,833 entitled "FINISHING RASP AND ORTHOPAEDIC SURGICAL PROCEDURE FOR USING THE SAME TO IMPLANT A REVISION HIP PROSTHESIS;" U.S. patent application Ser. No. 13/440,433, which issued as U.S. Pat. No. 9,597,188 entitled "VERSION-REPLICATING INSTRUMENT AND ORTHOPAEDIC SURGICAL PROCEDURE FOR USING THE SAME TO IMPLANT A REVISION HIP PROSTHESIS;" U.S. patent application Ser. No. 13/440,443, now abandoned, entitled "INSTRUMENT ASSEMBLY FOR IMPLANTING A REVISION HIP PROSTHESIS AND ORTHOPAEDIC SURGICAL PROCEDURE FOR USING THE SAME;" and U.S. patent application Ser. No. 13/440,448, which issued as U.S. Pat. No. 9,737,405 entitled "ORTHOPAEDIC SURGICAL PROCEDURE FOR IMPLANTING A REVISION HIP PROSTHESIS", each of which is assigned to the same assignee as the present application, each of which is filed concurrently herewith, and each of which is hereby incorporated by reference.

TECHNICAL FIELD

The present disclosure relates generally to orthopaedic instruments for use in the performance of an orthopaedic joint replacement procedure, and more particularly to orthopaedic instruments for use in the performance of a revision hip replacement procedure.

BACKGROUND

During the lifetime of a patient, it may be necessary to perform a joint replacement procedure on the patient as a result of, for example, disease or trauma. The joint replacement procedure may involve the use of a prosthesis which is implanted into one of the patient's bones. In the case of a hip replacement procedure, a femoral prosthesis is implanted into the patient's femur. Such a femoral prosthesis typically includes a spherically-shaped head which bears against the patient's acetabulum, along with an elongated intramedullary stem which is utilized to secure the femoral component to the patient's femur. To secure the prosthesis to the patient's femur, the intramedullary canal of the patient's femur is first surgically prepared (e.g. reamed and/or broached) such that the intramedullary stem of the femoral prosthesis may be subsequently implanted therein.

During performance of such a hip replacement procedure, it is generally necessary to provide the surgeon with a certain degree of flexibility in the selection of a prosthesis. In particular, the anatomy of the bone into which the prosthesis is to be implanted may vary somewhat from patient to patient. For example, a given patient's femur may be relatively long or relatively short thereby requiring use of a femoral prosthesis which includes a stem that is relatively long or short, respectively. Moreover, in certain cases, such as when use of a relatively long stem length is required, the stem must also be bowed in order to conform to the anatomy of the patient's femur.

As a result, modular prostheses have been designed. As its name implies, a modular prosthesis is constructed in modular form so the individual components of the prosthesis can be selected to fit the needs of a given patient's anatomy. For example, a typical modular prosthesis includes a proximal body component that can be assembled to any one of numerous distal stem components. Such a design allows the distal stem component to be selected and thereafter implanted in the patient's bone in a position which conforms to the patient's anatomy while also allowing for a degree of independent positioning of the proximal body component relative to the patient's acetabulum.

From time-to-time, a revision hip surgery may need to be performed on a patient. In such a revision hip surgery, the previously implanted hip prosthesis is surgically removed and a replacement hip prosthesis is implanted in the patient's femur.

SUMMARY

According to one aspect, a modular femoral prosthesis for use during performance of a hip revision procedure includes a proximal body component, a distal stem component, and a locking bolt.

According to another aspect, a starter reamer may be used to ream the intramedullary canal of a patient's femur during an orthopaedic surgical procedure to implant the modular femoral prosthesis.

According to another aspect, a distal reamer may be used to ream the intramedullary canal of a patient's femur subsequent to use of the starter reamer.

The distal reamer may be left in the intramedullary canal of a patient's femur subsequent to its use. A proximal trial instrument may then be coupled to the distal reamer and a trial reduction performed to confirm the appropriate leg length, component orientation, and offset.

According to another aspect, a reamer guide shaft may be coupled to the distal reamer while the reamer is positioned in the intramedullary canal of a patient's femur.

According to another aspect, a finishing rasp may be used to rasp the patient's femur.

According to yet another aspect, the distal stem component may be coupled to a stem insertion tool to facilitate implantation of the stem component into the intramedullary canal of a patient's femur.

According to another aspect, a proximal reamer may be used to ream the patient's femur to facilitate implantation of the proximal body component.

According to a further aspect, the proximal trial instrument may be coupled to a trial insertion tool and then secured to the implanted distal stem component.

According to another aspect, a version-replicating instrument may be coupled to the implanted distal stem component. The version of the proximal body component may be adjusted to match the version of the proximal trial instrument by use of the version-replicating instrument.

According to yet another aspect, a surgical tamp may be used to initially engage the taper lock connection between the distal stem component and the proximal body component.

According to another aspect, a stem stabilizer and a torque wrench may be used to install a locking bolt to lock the proximal body component to the distal stem component.

BRIEF DESCRIPTION OF THE DRAWINGS

The detailed description particularly refers to the following figures, in which:

FIG. 3 is an elevation view of a distal stem component of a modular femoral prosthesis for use along with the proximal body component during performance of a hip revision procedure;

FIG. 4 is a top elevation view of the distal stem component of FIG. 3;

FIG. 5 is a cross sectional view of the distal stem component taken along the line 5-5 of FIG. 3, as viewed in the direction of the arrows;

FIG. 6 is an enlarged fragmentary cross sectional view showing the distal stem component in greater detail, with FIG. 6 being taken from FIG. 5 as indicated by the encircled area;

FIG. 11 is a perspective view of the extension tool used to drive the distal reamer of FIGS. 9 and 10 during performance of a hip revision procedure;

FIG. 12 is an elevation view of the extension tool of FIG. 11;

FIG. 13 is a cross sectional view of the extension tool taken along the line 13-13 of FIG. 12, as viewed in the direction of the arrows;

FIG. 14 is a perspective view of the trial shaft of the proximal trial instrument used to perform a trial reduction during performance of a hip revision procedure;

FIGS. 15 and 16 are elevation views of the trial shaft of FIG. 14;

FIG. 17 is a cross sectional view of the trial shaft taken along the line 17-17 of FIG. 15, as viewed in the direction of the arrows;

FIG. 21 is a perspective view of the reamer guide shaft used to guide a number of instruments during performance of a hip revision procedure;

FIG. 22 is an elevation view of the reamer guide shaft of FIG. 21;

FIG. 23 is a cross sectional view of the reamer guide shaft taken along the line 23-23 of FIG. 22, as viewed in the direction of the arrows;

FIG. 24 is an elevation view of the finishing rasp used to surgically prepare the femur of the patient during performance of a hip revision procedure;

FIG. 25 is a cross sectional view of the finishing rasp taken along the line 25-25 of FIG. 24, as viewed in the direction of the arrows;

FIG. 30 is a perspective view of the proximal reamer used to surgically prepare the femur of the patient during performance of a hip revision procedure;

FIG. 31 is an elevation view of the proximal reamer of FIG. 30;

FIG. 32 is a cross sectional view of the proximal reamer taken along the line 32-32 of FIG. 31, as viewed in the direction of the arrows;

FIG. 33 is a perspective view of the trial insertion tool used to install the proximal trial instrument of FIGS. 14-20 during performance of a hip revision procedure;

FIG. 34 is a side elevation view of the trial insertion tool with its retention socket being shown in cross section for clarity of description;

FIG. 35 is an enlarged elevation view of the retention socket of the trial insertion tool;

FIG. 36 is a perspective view of the version-replicating instrument used during performance of a hip revision procedure;

FIG. 37 is a side elevation view of the version-replicating instrument of FIG. 36;

FIG. 38 is an enlarged cross sectional view of the distal end of the version-replicating instrument taken along the line 38-38 of FIG. 37, as viewed in the direction of the arrows;

FIG. 39 is an enlarged cross sectional view of the proximal end of the version-replicating instrument taken along the line 39-39 of FIG. 36, as viewed in the direction of the arrows;

FIG. 58 is a fragmentary elevation view showing the version-replicating instrument and the proximal body component being coupled to the implanted distal stem component during performance of a hip revision procedure;

FIG. 59 is an enlarged elevation view showing the version-replicating instrument and the distal stem component in greater detail, with FIG. 59 being taken from FIG. 58 as indicated by the encircled area, note FIG. 59 has been rotated 90° relative to FIG. 58 for clarity of description;

FIG. 60 is a fragmentary elevation view showing the proximal trial instrument being coupled to the version-replicating instrument during performance of a hip revision procedure;

FIG. 61 is a fragmentary elevation view showing the version of the proximal body component being adjusted to match the version of the proximal trial instrument by use of the version-replicating instrument during performance of a hip revision procedure;

FIG. 64 is a fragmentary elevation view showing the locking bolt being inserted into the proximal body component during performance of a hip revision procedure;

FIGS. 65 and 66 are fragmentary elevation views showing the locking bolt being tightened by use of the stem stabilizer and the T-shaped torque wrench during performance of a hip revision procedure;

FIG. 67 is a perspective view of the locking bolt of the modular femoral prosthesis for use along with the proximal body component and the distal stem component during performance of a hip revision procedure;

FIG. 68 is an elevation view of the locking bolt of FIG. 67;

FIG. 69 is a cross sectional view of the locking bolt taken along the line 69-69 of FIG. 68, as viewed in the direction of the arrows;

FIG. 70 is an enlarged cross sectional view showing the locking bolt in greater detail, with FIG. 70 being taken from FIG. 69 as indicated by the encircled area;

DETAILED DESCRIPTION OF THE DRAWINGS

Figure 2:
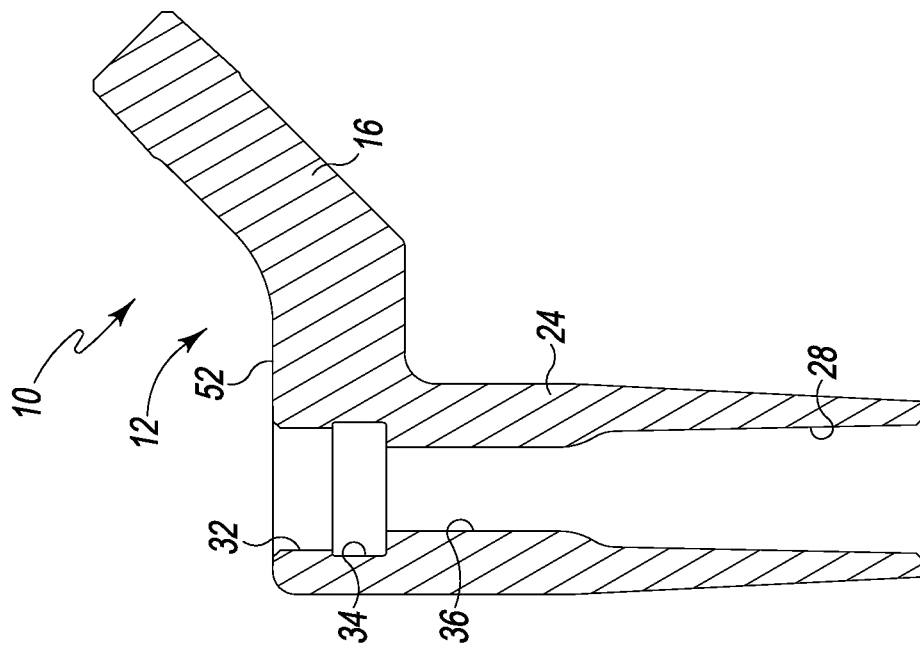
FIG. 2 is cross sectional view of the proximal body component of FIG. 1.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIGS. 1-5, there is shown a modular femoral prosthesis 10 for use during performance of a hip replacement procedure. The modular femoral prosthesis 10 includes a proximal body component 12 and a distal stem component 14. As will be discussed below in regard to FIGS. 64-66, the modular femoral prosthesis also includes a locking bolt 504 that provides a secondary lock between the proximal body component 12 and the distal stem component 14 (the primary lock being the taper lock described below). The prosthesis 10 is configured to be implanted into a femur 20 (see FIGS. 40-57) of a patient during a hip revision procedure. In particular, the modular prosthesis 10 is implanted into a surgically prepared (e.g. reamed and/or broached) intramedullary canal 22 of the patient's femur 20.

A head component (not shown) is secured to the end of the elongated neck 16 of the proximal body component 12 to bear on either the patient's natural acetabulum or a prosthetic socket which has been implanted into the patient's pelvis to replace his or her acetabulum. In such a manner, the modular femoral prosthesis 10 and the natural or artificial acetabulum collectively function as a system which replaces the natural joint of the patient's hip.

The distal stem component 14 may be provided in a number of different configurations in order to fit the needs of a given patient's anatomy. In particular, the stem component 14 may be configured in various different lengths to conform to the patient's anatomy (e.g. a relatively long stem component 14 for use with a long femur 20, a relatively short stem for use with a short femur 20, etcetera). Moreover, the distal stem component 14 may also be provided in a bow-shaped configuration if required by a given patient's anatomy. Yet further, the distal stem component 14 may also be provided in various diameters if required by a given patient's anatomy. In one illustrative embodiment, the stem component 14 may be provided in four different lengths—140 mm, 190 mm, 240 mm, and 290 mm Such stem components are provided in 1 mm diameter increments ranging from 14 to 31 mm, although in some embodiments certain of the sizes in such a range (e.g., 28 mm and 30 mm) may be omitted. In such an illustrative embodiment, straight stem components are available in the two shorter lengths (i.e., 140 mm and 190 mm lengths), with the three longer stem lengths (i.e., 190 mm, 240 mm, and 290 mm) being available with a 3° angle to accommodate the curvature of the femoral anterior bow.

Likewise, the proximal body component 12 (and the head component secured thereto) may also be provided in various different configurations to provide the flexibility necessary to conform to varying anatomies from patient to patient. For example, the proximal body component 12 may be provided in four different lengths—75 mm, 85 mm, 95 mm, and 105 mm Like the distal stem component 14, the proximal body component 12 may also be provided in various diameters. For example, in one illustrative embodiment, the proximal body component 12 may be provided in three different diameters—20 mm, 24 mm, and 28 mm. The offset of the proximal body component 12 may be varied to increase the offset of the prosthesis 10. The head component may be provided in varying diameters to fit the needs of a given patient's anatomy.

Figure 1:
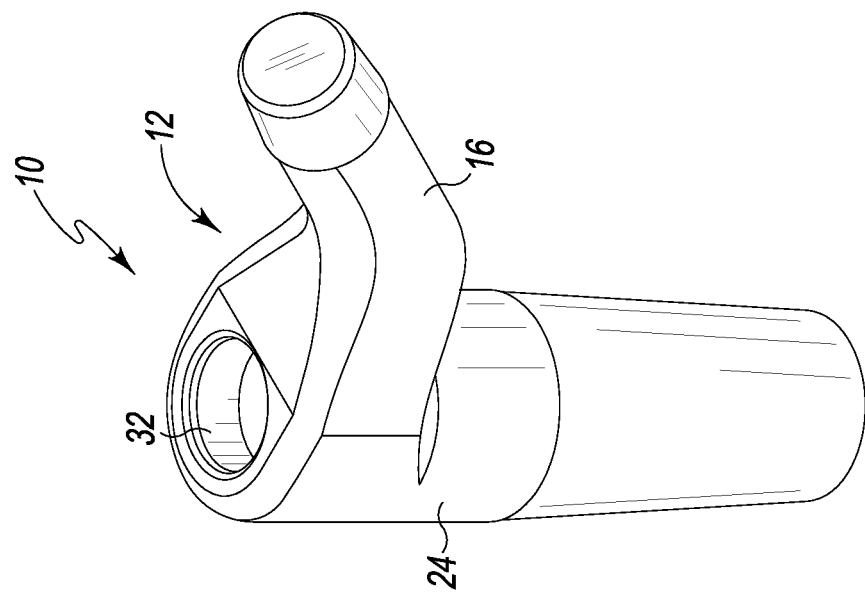
FIG. 1 is a perspective view of a proximal body component of a modular femoral prosthesis for use during performance of a hip revision procedure.

As shown in FIGS. 1 and 2, the proximal body component 12 includes a body 24, with the neck 16 extending medially therefrom. The head component (not shown) is taper fit or otherwise secured to the end of the elongated neck 16. The body 24 also has an tapered bore 28 formed therein. A tapered post 30 of the distal stem component 14 (see FIGS. 3-6) is received into the tapered bore 28 of the proximal body component 12. As will be discussed below in greater detail below, urging the tapered post 30 of the distal stem component 14 and the sidewall defining the tapered bore 28 of the proximal body component 12 toward one another taper locks the proximal body component 12 to the distal stem component 14.

The superior surface of the body 24 of the proximal body component 12 has a countersunk cavity 32 formed therein. The inferior side of the countersunk cavity 32 opens into a locking recess 34. The inferior side of the locking recess 34 opens into a connecting bore 36, which in turn opens into the tapered bore 28. As will be discussed below in greater detail, a locking bolt 504 (see FIG. 64) is inserted through the countersunk cavity 32 and thereafter extends through the connecting bore 36 to engage the distal stem component 14.

As shown in FIGS. 3-6, the tapered post 30 is formed in the superior end of the body 38 of the distal stem component 14. The superior surface of the body 38 of the distal stem component 14 has a set of upper threads 40 formed therein. As will be discussed below in more detail, the upper threads 40 are used to couple the distal stem component 14 to surgical instruments that are impacted during use thereof. A set of lower threads 42 are positioned inferiorly of the upper threads 40. The lower threads 42 are used to couple the distal stem component 14 to the locking bolt 504 (see FIG. 64) of the hip prosthesis 10, along with those surgical instruments that are not impacted during their use. By not subjecting the lower threads to impacted surgical instruments during implantation of the femoral prosthesis 10, the threads ultimately used to secure the prosthesis's bolt (i.e., the lower threads 42) are protected from damage during the surgical procedure. In the exemplary embodiment described herein, the upper threads 40 are M8 size threads, whereas the lower threads 42 are M6 size threads.

In the illustrative embodiment described herein, the lower threads 42 are embodied as modified threads designed to relieve stress risers. In particular, as can be seen best in FIG. 6, the outer edges 54 of the lower threads 42 are rounded. Unexpectedly, testing and modeling have shown that such rounded edges 54 provide relief from stress risers in the distal stem component 14. Additional relief from stress risers is also provided by the design of the distal end of the blind hole in which the lower threads 42 are formed. In particular, in lieu of a point or other geometry, the distal end 56 of the blind hole extending posteriorly from the lower threads 42 is rounded. That is, the blind hole formed in the body 38 of the distal stem component 14 that extends posteriorly from the threads 42 has a rounded distal end 56. Like the rounded outer edges 54 of the lower threads 42, testing and modeling have unexpectedly shown that such a rounded distal end 56 provides relief from stress risers in the distal stem component 14.

An alignment key 44 in the form of, for example, a tab extends superiorly from the superior surface of the body 38 of the distal stem component 14. The alignment key 44 is in line with the apex of the distal stem component 14. That is, bowed stem components 14 have an apex (i.e., a spine) that runs along the convex side of its curvature. During implantation of the distal stem component 14, the apex must be properly aligned with the corresponding side of the patient's femur 20 possessing a similar curvature. As will be described below, the alignment key 44 facilitates proper orientation of the apex of the distal stem component 14 by allowing the surgeon to visualize the location of the apex even when the stem component 14 is positioned in the intramedullary canal.

As can be seen in FIG. 4, a keyway 46 is formed in the superior surface of the body 38 of the distal stem component 14. The keyway 46 is formed in the sidewall 48 that defines the outer opening 50 of the upper threads 40. In the exemplary embodiment described herein, the keyway 46 is embodied as a lobe-shaped slot configured to receive a lobe-shaped key of a surgical trial instrument, although other shaped slots and tabs may be used. As will be discussed below, such a feature allows a trialed orientation of a proximal trial body component to be replicated for use in implanting the proximal body component 12.

Figures 7, 8, 9, 10:
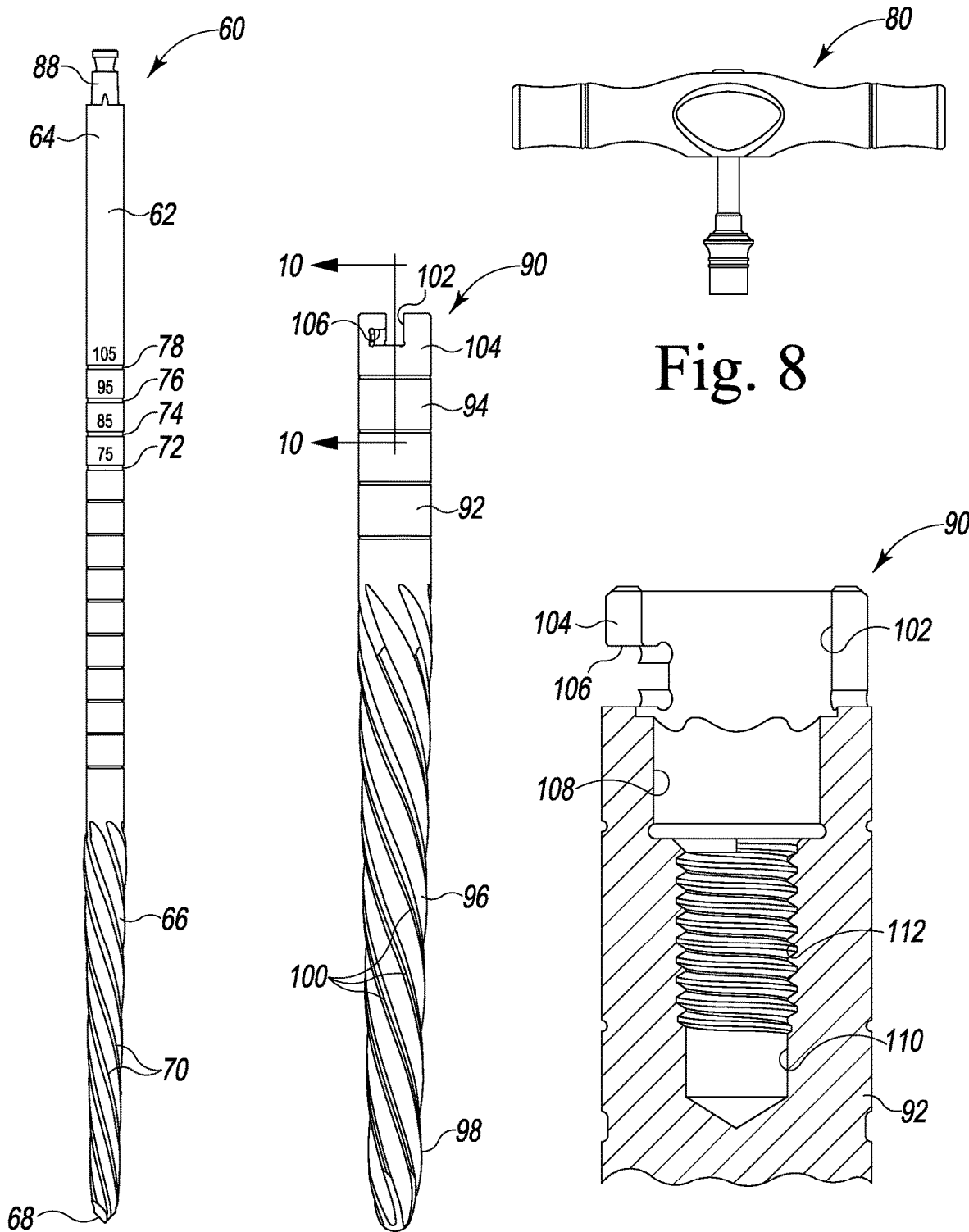
FIG. 7 is an elevation view of the starter reamer used to surgically prepare the femur of the patient during performance of a hip revision procedure.
FIG. 8 is a manual handle that may be used to drive the various instruments described herein.
FIG. 9 is an elevation view of the distal reamer used to surgically prepare the femur of the patient during performance of a hip revision procedure.
FIG. 10 is an enlarged cross sectional view of the distal reamer taken along the line 10-10 of FIG. 9, as viewed in the direction of the arrows.

Referring now to FIGS. 7-43, there are shown the various instruments used to implant the femoral prosthesis 10 into the intramedullary canal 22 of the patient's femur 20. In FIG. 7, there is shown a starter reamer 60 that may be used during the initial steps of the surgical preparation of the patient's femur 20. The starter reamer 60 is used to ream the portion of the patient's intramedullary canal 22 into which the distal stem component 14 is implanted. The starter reamer 60 includes an elongated shank 62 having a proximal end 64 that fits into the chuck of a rotary power tool 86 (see FIG. 45) or a manual handle 80 (see FIGS. 8 and 44). The starter reamer 60 also includes a cutting head 66 located at the opposite, distal end of the shank 62. The cutting head 66 of the starter reamer 60 includes a sharp cutting tip 68 with a plurality of helical cutting flutes 70 extending therefrom.

The cutting tip 68 cuts through any debris or cement remnants from the previously-removed femoral prosthesis. When the starter reamer 60 is positioned in the intramedullary canal 22 of the patient's femur 20 and rotated, the cutting head 66 reams or otherwise cuts the bone tissue of the femur thereby obtaining clear access to the femoral canal. Such access to the femoral canal ensures proper alignment of the components of the femoral prosthesis 10.

The starter reamer 60 includes a number of colored depth marks 72, 74, 76, 78 formed on its shank 62 at a location above the proximal end of the cutting head 66. Each of the colored depth marks 72, 74, 76, 78 corresponds to the standard head center of a number of different proximal body components 12. For example, the proximal body component 12 may be provided in four different lengths—75 mm, 85 mm, 95 mm, and 105 mm. In the exemplary embodiment described herein, the depth mark 72 is blue and corresponds to the location of the center of the head of a 75 mm proximal body component 12, the depth mark 74 is green and corresponds to the location of the center of the head of a 85 mm proximal body component 12, the depth mark 76 is yellow and corresponds to the location of the center of the head of a 95 mm proximal body component 12, and the depth mark 78 is red and corresponds to the location of the center of the head of a 105 mm proximal body component 12. The depth marks 72, 74, 76, 78 may be embodied as grooves engraved in the shank 62, each of which is filled with an epoxy ink of the corresponding color. During a surgical procedure, the starter reamer 60 is advanced deeper into the intramedullary canal 22 of the patient's femur 20 until the desired depth mark aligns with the tip 82 of the greater trochanter 84 (see FIG. 44) and clear access to the canal 22 is achieved. In such a way, over reaming of the distal end of the canal 22 is avoided if the starter reamer 60 is not driven beyond the appropriate colored depth mark 72, 74, 76, 78.

A male connector 88 is formed in the proximal end 64 of the shank 62 of the starter reamer 60. The connector 88 fits into the chuck of a rotary power tool 86 (see FIG. 45) or a manual handle 80 (see FIG. 8) to couple the starter reamer 60 to a rotary drive source.

The starter reamer 60 may be constructed from a medical-grade metal such as stainless steel, cobalt chrome, or titanium, although other metals or alloys may be used. Moreover, in some embodiments, rigid polymers such as polyetheretherketone (PEEK) may also be used.

Referring now to FIGS. 9 and 10, there is shown a distal reamer 90 that may be used after the starter reamer 60 during the surgical preparation of the patient's femur 20. Like the starter reamer 60, the distal reamer 90 is used to ream the portion of the patient's intramedullary canal 22 into which the distal stem component 14 is implanted. The use of progressively larger distal reamers 90 produces a bore possessing the final geometry (i.e., the shape) required to accept the distal stem component 14 of the femoral prosthesis 10. The distal reamer 90 includes an elongated shank 92 having a proximal end 94 that mates with an extension tool 120 (see FIGS. 11-13). As will be described below in greater detail, the extension tool 120 may in turn be secured to the chuck of the rotary power tool 86 (see FIG. 45) or the manual handle 80 (see FIG. 8).

The distal reamer 90 also includes a cutting head 96 located at the opposite, distal end 98 of the shank 92. The cutting head 96 of the distal reamer 90 includes a plurality of helical cutting flutes 100. The outer cutting surfaces of the cutting flutes 100 are tapered to mimic the geometry of the distal stem component 14. When the distal reamer 90 is positioned in the intramedullary canal 22 of the patient's femur 20 and rotated, the cutting flutes 100 ream or otherwise cut the bone tissue of the femur 20.

To accommodate the various different configurations of the distal stem components 14, the distal reamer 90 may likewise be provided in a number of different configurations. In particular, the distal reamer 90 may be configured in various different lengths to produce a reamed bore of a size sufficient to receive distal stem components 14 of various different lengths (e.g. a relatively long distal reamer 90 to prepare the femur 20 for implantation of a relatively long stem component 14, a relatively short distal reamer 90 to prepare the femur 20 for implantation of a relatively short stem component 14, etcetera). Yet further, the distal reamer 90 may be provided in a number of various diameters to produce a reamed bore of the diameter sufficient to receive distal stem components 14 of various diameters. In one illustrative embodiment, the distal reamer 90 may be provided in four different lengths—140 mm, 190 mm, 240 mm, and 290 mm Such reamers 90 are provided in 1 mm diameter increments ranging from 14 to 31 mm.

The proximal end 94 of the distal reamer 90 has a countersunk drive connector 102 formed therein. The drive connector 102 is shaped to receive the locking jaws 148 and the drive spline 126 of the extension tool 120 (see FIGS. 11-13). The sidewall 104 that defines the drive connector 102 has a number of L-shaped locking slots 106 defined therein. Positioned posteriorly of the locking slots 106, the sidewall 104 that defines the drive connector 102 has a female drive socket 108 defined therein. In the illustrative embodiment described herein the female drive socket 108 is embodied as a female hex drive socket the compliments the size and shape of the drive spline 126 of the extension tool 120. As will described below in regard to FIGS. 11-13, the locking jaws 148 of the extension tool 120 may be positioned in the locking slots 106 and thereafter engaged with the sidewall 104 to selectively lock the extension tool 120 to the proximal end 94 of the distal reamer 90. In doing so, the extension tool's drive spline 126 is received into the female drive socket 108 of the distal reamer 90. When the extension tool 120 is locked to the distal reamer 90 in such a way, rotation of the extension tool's drive spline 126 causes rotation of the distal reamer 90.

As can be seen in the cross section of FIG. 10, the proximal end of a blind bore 110 opens into the connector 102. The blind bore 110 extends distally away from the female drive socket 108. The upper end of the blind bore 110 is threaded. Namely, a number of threads 112 are formed in the sidewall that defines the proximal end of the blind bore 110. In the illustrative embodiment described herein, the threads 112 do not extend throughout the length of the blind bore 110. As a result, the bore's distal end is smooth (i.e., not threaded). The threads 112 are sized to match the lower threads 42 of the distal stem component 14. As such, in the illustrative embodiment described herein, the threads 112 are M6 size threads.

Like the starter reamer 60, the distal reamer 90 may be constructed from a medical-grade metal such as stainless steel, cobalt chrome, or titanium, although other metals or alloys may be used. Moreover, in some embodiments, rigid polymers such as polyetheretherketone (PEEK) may also be used.

Referring now to FIGS. 11-13, there is shown an extension tool 120 that may be used in conjunction with the distal reamer 90 during the surgical preparation of the patient's femur 20. The extension tool 120 may be used to drive the distal reamer 90 to ream the portion of the patient's intramedullary canal 22 into which the distal stem component 14 is implanted. The extension tool 120 includes an elongated drive shaft 122 having a proximal end 124 that fits into the chuck of a rotary power tool 86 (see FIG. 45) or a manual handle 80 (see FIG. 8). The extension tool 120 also includes a drive spline 126 located at the opposite, distal end 128 of the drive shaft 122. The drive spline 126 of the extension tool 120 includes a plurality of drive teeth 130. When the drive teeth 130 of the drive spline 126 are positioned in the female drive socket 108 of the distal reamer 90, the drive shaft 122 is coupled to the distal reamer 90. As such, rotation of the drive shaft 122 causes rotation of the distal reamer 90.

The drive shaft 122 of the extension tool 120 includes an elongated shaft body 132. A male connector 134 is formed in the proximal end 136 of the shaft body 132. The connector 134 fits into the chuck of a rotary power tool 86 (see FIG. 45) or a manual handle 80 (see FIG. 8) to couple the drive shaft 122 to a rotary drive source. A sleeve 138 is positioned around the shaft body 132. The sleeve 138 is coupled to the outer surface of the shaft body 132 through a bearing 140. As such, the shaft body 132 (and hence the drive shaft 122) rotates freely of the sleeve 138. The sleeve 138 functions as a grip for allowing the surgeon to hold the extension tool 120 during rotation of the drive shaft 122.

An elongated tip 142 extends distally away from the distal end of the shaft body 132. In particular, a proximal end 144 of the elongated tip 142 is secured to the distal end 146 of the shaft body 132. The elongated tip 142 has a pair of locking flanges 148 formed in its distal end. The locking jaws 148 face oppositely one another. The tip 142 has an elongated bore 150 extending therethrough. The distal end of the elongated bore 150 (i.e., the portion of the bore 150 proximate the locking jaws 148) defines a distal bore 152 that has a smaller diameter than a proximal bore 154 defined by the remainder of the bore 150. The sidewall defining the distal bore 152 has an internal geometry that matches the external geometry of the drive spline 126. Such a complimentary feature enhances the rotational stability of the extension tool 120 as it drives the distal reamer 90.

The drive shaft 122 also includes a locking assembly 156. The locking assembly 156 includes a locking lever 158 that is pivotally coupled to the shaft body 132 via a pivot pin 160. One end of a spring link 162 is coupled to the locking lever 158, with its other end being coupled to the proximal end 164 of a spline shaft 166. The drive spline 126 is formed in the distal end 168 of the spline shaft 166. The drive spline 126 is positionable between an extended or locked position (as shown in FIG. 13) in which the drive spline 126 extends out of the distal end of the elongated tip 142 and a retracted or unlocked position in which the drive spline 162 is retracted into the distal bore 152 of the elongated tip 142 to a location that is proximal of the locking jaws 148.

To secure the extension tool 120 to the distal reamer 90, the locking jaws 148 are inserted through the open ends of the locking slots 106 of the distal reamer's drive connector 102 and thereafter rotated. The drive spline 126 is then positioned in its extended (i.e., locked) position in which it is received in the distal reamer's female drive socket 108 to secure the extension tool 120 to the distal reamer 90.

By virtue of being coupled to the spline shaft 166 via the spring link 162, the locking lever 158 is operable to move the drive spline 126 between its extended (i.e., locked) position and its retracted (i.e., unlocked) position. Namely, when the locking lever 158 is positioned in its locked position (as shown in FIG. 13), the drive spline is positioned in its extended (i.e., locked) position. However, when the locking lever 158 is pulled downwardly (in the orientation of FIG. 13) so as to pivot about the pivot pin 160, the spring link 162 and hence the spline shaft 166 are urged to the right (in the orientation of FIG. 13) so as to relieve tension from the spring link 162 and position the drive spline 126 in its retracted (i.e., unlocked) position.

The extension tool 120 includes a number of colored depth marks 172, 174, 176, 178 formed on its elongated tip 142. Like the depth marks 72, 74, 76, 78 of the starter reamer 60, each of the colored depth marks 172, 174, 176, 178 corresponds to the standard head center of one of the various proximal body components 12. For example, the proximal body component 12 may be provided in four different superior/inferior lengths—75 mm, 85 mm, 95 mm, and 105 mm. In the exemplary embodiment described herein, the depth mark 172 is blue and corresponds to the location of the center of the head of a 75 mm proximal body component 12, the depth mark 174 is green and corresponds to the location of the center of the head of a 85 mm proximal body component 12, the depth mark 176 is yellow and corresponds to the location of the center of the head of a 95 mm proximal body component 12, and the depth mark 178 is red and corresponds to the location of the center of the head of a 105 mm proximal body component 12. The depth marks 172, 174, 176, 178 may be embodied as grooves engraved in the elongated tip 142, each of which is filled with an epoxy ink of the corresponding color. During a surgical procedure, the extension tool 120 is advanced deeper into the intramedullary canal 22 of the patient's femur 20 until the desired depth mark aligns with the tip 82 of the greater trochanter 84 (see FIG. 45). In such a way, over reaming of the distal end of the canal 22 is avoided if the extension tool 120 is not driven beyond the appropriate colored depth mark 172, 174, 176, 178.

The extension tool 120 is configured to mate with any of the various configurations of the distal reamer 90. In other words, each of the various configurations of the distal reamers 90 is compatible with the extension tool 120.

The metallic components of the extension tool 120 (e.g., the various components of the drive shaft 126, the distal tip 142, etcetera) may be constructed from a medical-grade metal such as stainless steel, cobalt chrome, or titanium, although other metals or alloys may be used. Moreover, in some embodiments, rigid polymers such as polyetheretherketone (PEEK) may also be used. The sleeve 138 may be constructed from similar metals or from a polymer such as delrin.

Referring now to FIGS. 14-20, there is shown a proximal trial instrument 180. The proximal trial instrument 180 is modular and, as a result, is embodied as two separate components—a trial shaft 182 and a trial neck 184. Like the other instruments and implants described herein, the components of the proximal trial instrument 180 (i.e., the trial shaft 182 and the trial neck 184) may be provided in a number of different sizes. For example, in the illustrative embodiment described herein, the trial shaft 182 may be embodied in four different lengths (e.g., 75 mm, 85 mm, 95 mm, or 105 mm) so as to, when assembled to the distal reamer 90 or the distal stem component 14, mimic a 75 mm, 85 mm, 95 mm, or 105 mm proximal body component 12. In the illustrative embodiment described herein, the trial neck 184 may be provided in two different offset sizes—45 mm and 40 mm. The various configurations of the trial shaft 182 and the trial neck 184 may be mixed and matched to produce trials of different sizes. Such a modular instrument significantly reduces the number of instruments needed to perform the associated surgical procedure. For example, some prior art trial instrument sets included 12 different proximal trial instruments, whereas the illustrative system described herein has six instruments (four trial shafts and two trial necks).

As can be seen in FIGS. 14-17, the trial shaft 182 includes a body 186 having an elongated bore 188 extending therethrough. A locking screw 190 is captured in the bore 188. A hex drive head 192 is formed in the proximal end of the locking screw 190, with a number of locking threads 194 being formed in its opposite, distal end. The threads 194 are sized to be received into the lower threads 42 of the distal stem component 14 and the threads 112 of the distal reamer 90. As such, in the illustrative embodiment described herein, the threads 194 of the locking screw 190 are M6 size threads. As can be seen in the perspective view of FIG. 14 and the cross-sectional view of FIG. 17, the drive head 192 of the locking screw 190 is captured in a bearing 196 and positioned in a recess 198 formed in the proximal end of the trial shaft's body 186.

The body 186 of the trial shaft 182 is generally cylindrical in shape. The proximal end 202 of the body 186 defines a stem 204 to receive the trial neck 184. A shoulder 206 is formed in the body 186. The trial neck 184 slides down the stem 204 and is supported by the shoulder 206. As can be seen in FIGS. 14-16, the stem 204 has a splined surface 208 formed therein. As will be described in more detail below, the splined surface 208 is engaged by a locking pawl 244 of the trial neck 184 (see FIG. 18) to lock the trial neck 184 into a desired orientation or "version" (i.e., rotational angle) relative to the trial shaft 182.

As can be seen in FIGS. 14-16, an alignment flat 210 is formed in the trial shaft's body 186. The flat 210 is formed near the body's distal end 212. The alignment flat 210 is embodied as a flat, shallow slot. The flat 210 facilitates insertion of the proximal trial instrument 180 during a surgical procedure.

The trial shaft 182 also includes an alignment key 214 in the form of, for example, a rib that extends outwardly from the distal end 212 of the body 186. The long axis of the alignment key 214 extends in the superior/inferior direction. The alignment key 214 is configured to mate with the keyway 46 formed in the superior surface of the body 38 of the distal stem component 14 (see FIG. 4). In the exemplary embodiment described herein, the cross-sectional shape of the alignment key 214 is lobe shaped to compliment the shape of the stem component's keyway 46.

Figure 19:
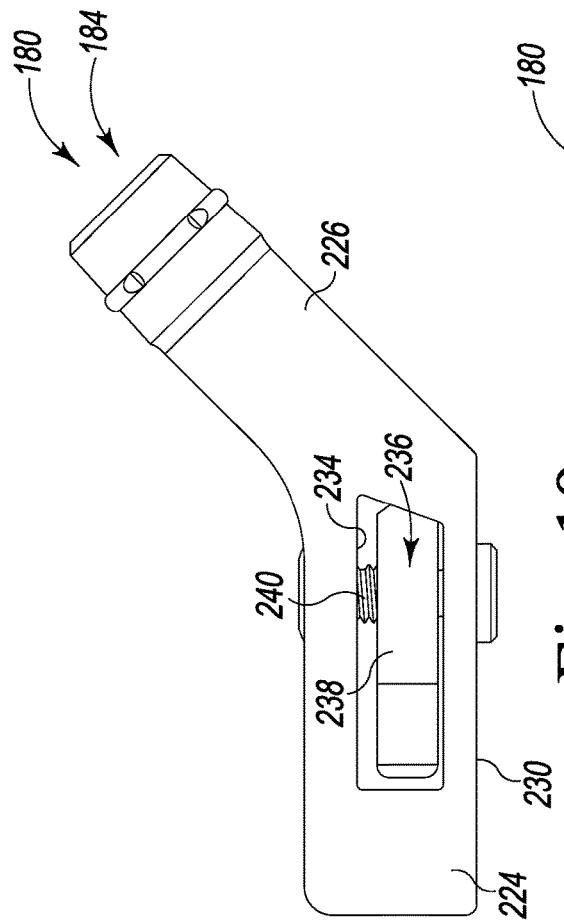
FIG. 19 is an elevation view of the trial neck of FIG. 18.
Figure 20:
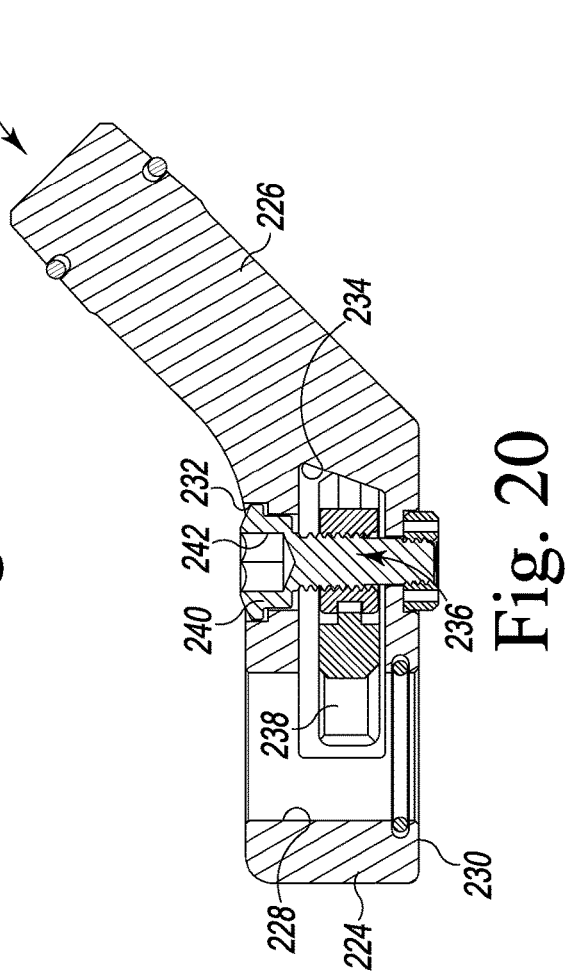
FIG. 20 is a cross sectional view of the trial neck taken along the line 20-20 of FIG. 18, as viewed in the direction of the arrows.
Figure 18:
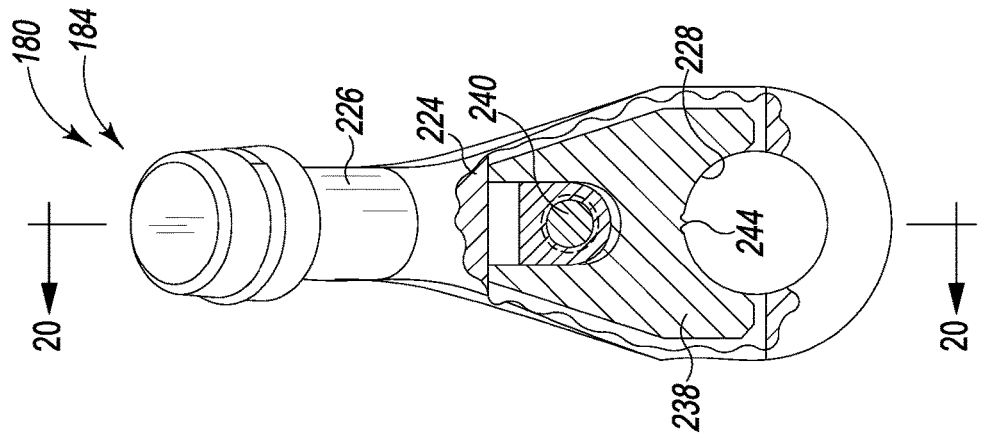
FIG. 18 is a top elevation view of the trial neck of the proximal trial instrument used to perform a trial reduction during performance of a hip revision procedure, note a portion of the trial neck has been cutaway to show the trial neck's friction clamp in greater detail.

As shown in FIGS. 18-20, the trial neck 184 includes a body 224 having a neck 226 extending medially therefrom. A trial head (not shown) is taper fit or otherwise secured to the neck 226. The body 224 also has a bore 228 formed therein. The bore 228 extends in the superior/inferior direction through the lateral portion of the body 224. The proximal stem 204 of the trial shaft 182 is received into the bore 228 of the trial neck 184. The trial neck 184 slides down the stem 204 of the trial shaft 182 until an inferior surface 230 of the trial neck's body 224 contacts the shoulder 206 formed in the body 186 of the trial shaft (see FIGS. 14-17).

The superior surface of the body 224 of the trial neck 184 has a countersunk cavity 232 formed therein. The inferior side of the countersunk cavity 232 opens into a locking recess 234. The cavity 232 and the recess 234 house a locking mechanism 236. The locking mechanism 236 includes a friction clamp 238 and a locking screw 240. A hex drive head 242 is formed in the proximal end of the locking screw 240. When the trial neck 184 is positioned on the trial shaft 182, the locking mechanism 236 may used to lock the trial neck 184 into a desired orientation or "version" (i.e., rotational angle) relative to the trial shaft 182. In particular, when the locking screw 240 is tightened by use of a hex driver (such as the one shown in FIG. 56), the friction clamp 238 clamps onto or otherwise engages the outer surface of the stem 204 of the trial shaft 182 thereby preventing the trial neck 184 from rotating relative to the trial shaft 182. As can be seen in FIG. 18, the friction claim 238 has a locking pawl 244 formed therein. When the locking screw 240 is tightened by use of a hex driver 512 (such as the one shown in FIG. 56), the locking pawl 244 is urged into positioned in one of the grooves of the splined surface 208 of the trial shaft 182. The locking pawl 244 contacts the sidewalls forming the groove of the splined surface 208 thereby preventing the trial neck 184 from rotating relative to the trial shaft 182. When the locking screw 240 is loosened with the hex driver, the friction clamp 238 disengages the stem 204 of the trial shaft 182 thereby allowing the trial neck 184 to rotate freely about the trial shaft 182.

The trial shaft 182 and the trial neck 184 of the proximal trial instrument 180 may be constructed from a medical-grade metal such as stainless steel, cobalt chrome, or titanium, although other metals or alloys may be used. Moreover, in some embodiments, rigid polymers such as polyetheretherketone (PEEK) may also be used.

Referring now to FIGS. 21-23, there is shown a reamer guide shaft 250. The reamer guide shaft 250 may be secured to the distal stem component 14 or the distal reamer 90 positioned in the intramedullary canal 22 of the patient's femur 20 to guide a surgeon's advancement of a finishing rasp 290 (see FIGS. 24 and 25) or proximal reamer 390 (see FIGS. 30-32). The reamer guide shaft 250 includes a body 252 having an elongated bore 254 extending therethrough. A locking screw 256 is captured in the bore 254. A hex drive socket 258 is formed in the proximal end of the locking screw 256, with a number of locking threads 260 being formed in its opposite, distal end. As will be described below in greater detail, a hex driver may be inserted into the hex drive socket 258 and rotated to tighten the reamer guide shaft 250 to the distal stem component 14 or the distal reamer 90. The locking screw's threads 260 are sized to be received into the lower threads 42 of the distal stem component 14 and the threads 112 of the distal reamer 90. As such, in the illustrative embodiment described herein, the threads 260 of the locking screw 256 are M6 size threads.

The distal end 262 of the body 252 of the reamer guide shaft 250 has an alignment flat 264 formed therein. The alignment flat 264 is embodied as a flat, shallow slot. The alignment flat 264 is sized and shaped to closely complement the size and shape of the alignment key 44 extending superiorly from the superior surface of the body 38 of the distal stem component 14. As mentioned above, the alignment key 44 aligns with the apex of the distal stem component 14. During attachment of the reamer guide shaft 250 to the distal stem component 14, the alignment key 44 abuts into contact with the alignment flat 264 formed in the reamer guide shaft's body 252.

Like the trial shaft 182 of the proximal trial instrument 180, the reamer guide shaft 250 also includes an alignment key 284 in the form of, for example, a rib that extends outwardly from the distal end 262 of the body 252. The long axis of the alignment key 284 extends in the superior/inferior direction. The alignment key 284 is configured to mate with the keyway 46 formed in the superior surface of the body 38 of the distal stem component 14 (see FIG. 4). In the exemplary embodiment described herein, the cross-sectional shape of the alignment key 284 is lobe shaped to compliment the shape of the stem component's keyway 46.

The reamer guide shaft 250 includes a number of colored depth marks 272, 274, 276, 278 formed on its body 252. Like the depth marks 72, 74, 76, 78 of the starter reamer 60 and the depth marks 172, 174, 76, 178 of the extension tool 120, each of the colored depth marks 272, 274, 276, 278 corresponds to the standard head center of one of the various proximal body components 12. For example, as described above, the proximal body component 12 may be provided in four different superior/inferior lengths—75 mm, 85 mm, 95 mm, and 105 mm. In the exemplary embodiment described herein, the depth mark 272 is blue and corresponds to the location of the center of the head of a 75 mm proximal body component 12, the depth mark 274 is green and corresponds to the location of the center of the head of a 85 mm proximal body component 12, the depth mark 276 is yellow and corresponds to the location of the center of the head of a 95 mm proximal body component 12, and the depth mark 278 is red and corresponds to the location of the center of the head of a 105 mm proximal body component 12. The depth marks 272, 274, 276, 278 may be embodied as grooves engraved in the body 252 of the reamer guide shaft 250, each of which is filled with an epoxy ink of the corresponding color.

The reamer guide shaft 250 also includes another colored mark 280 formed near its proximal end. As can be seen in FIGS. 21 and 22, the colored mark 280 is formed in the outer surface of the reamer guide shaft's body 252. Like the colored depth marks 272, 274, 276, 278, the colored mark 280 may be embodied as a groove that is engraved in the reamer guide shaft's body 252 and filled with an epoxy ink of a predetermined color, or, alternatively, may be embodied as a laser mark. In the illustrative embodiment described herein, the colored mark 280 is black. As will be described below in greater detail, the colored mark 280 allows a surgeon to visually confirm that proper seating height has been achieved by observing the colored mark 280 through the window 314 formed in the finishing rasp 290 (see FIGS. 24 and 25) or the window 414 formed in the proximal reamer 390 (see FIGS. 30-32). In particular, during a surgical procedure, the finishing rasp 290 (see FIGS. 24 and 25) or proximal reamer 390 (see FIGS. 30-32) is advanced deeper into the intramedullary canal 22 of the patient's femur 20 until the colored mark 280 is visible through a window 314 formed in the finishing rasp 290 (see FIGS. 24 and 25) or a window 414 formed in the proximal reamer 390 (see FIGS. 30-32), respectively. In such a way, over rasping or over reaming of the intramedullary canal 22 is avoided.

The reamer guide shaft 250 may be constructed from a medical-grade metal such as stainless steel, cobalt chrome, or titanium, although other metals or alloys may be used. Moreover, in some embodiments, rigid polymers such as polyetheretherketone (PEEK) may also be used.

Referring now to FIGS. 24 and 25, the finishing rasp 290 is shown in more detail. The finishing rasp 290 is used in the surgical preparation of the femur 20 of certain patients. For example, when implanting bowed distal stem components 14 having relatively small diameters (e.g., 14-20 mm) in patients who do not present a large proximal deformity, it may be necessary to utilize the finishing rasp 290. The finishing rasp 290 removes additional bone to facilitate the proper seating of a bowed distal stem component 14.

Like the other instruments and implants described herein, the finishing rasp 290 may be provided in a number of different sizes. For example, finishing rasp 290 may be provided in various diameters to accommodate the different diameters of the various different distal stem components 14. In one illustrative embodiment, the stem component 14 may be provided in 1 mm diameter increments ranging from 14 to 31 mm. In such a case, the finishing rasp 290 may be provided in similar sizes.

The finishing rasp 290 includes an elongated shaft 292 having a handle 294 secured to its proximal end 296. The finishing rasp 290 also includes a cutting head 298 secured to the opposite, distal end 302 of the shaft 292. The cutting head 298 of the finishing rasp 290 is arcuate in shape and includes a plurality of cutting teeth 304 on its two outer sides. The cutting teeth 304 extend longitudinally along the length of the cutting head 298. When the finishing rasp 290 is advanced with oscillating motion, the cutting teeth 304 of the finishing rasp 290 abrade or otherwise cut the bone tissue of the femur 20 in two directions thereby gradually creating a notch possessing the geometry (i.e., the shape) required to accept a bowed distal stem component 14.

As can be seen in FIG. 25, the handle 294 is positioned on the shaft 292 of the finishing rasp 290 such that one end of the handle 294 is longer than the other. This provides a visual reference to the surgeon as to the location of the cutting head 298. Namely, the cutting head 298 is located on the same side of the shaft 292 as the short side of the handle 294. In doing so, the short side of the handle 294 provides the surgeon with a visual reference as to where the cutting head 298 is located during use of the finishing rasp 290 This allows the cutting head 298 to be aligned 180° from the anticipated location of the distal stem component's apex.

The shaft 292 of the finishing rasp 290 has a blind guide bore 306 formed therein. As can be seen in the cross sectional view of FIG. 25, the distal end 308 of the guide bore 306 is defined in (i.e., opens through) the distal end 302 of the shaft 292 of the finishing rasp 290 at a location proximate to the cutting head 298. As noted above, the cutting head 298 is generally arcuate in shape with its concave side facing the central axis of the shaft 292. Such a shape provides clearance for the reamer guide shaft 250 to enter the guide bore 306.

The opposite, proximal end 310 of the guide bore 306 is located in the rasp's elongated shaft 292 at a location between its proximal end 296 and its distal end 302. The proximal end 310 of the guide bore 306 is located on the proximal side of the middle of the shaft 292 near where the shaft 292 tapers down to its smaller diameter that is secured to the handle 294. The center line of the guide bore 306 and the longitudinal axis of the finishing rasp 290 lie on the same line.

A depth stop 312 is located in the proximal end 310 of the guide bore 306. The depth stop 312 bottoms out on the superior surface 282 of the drive socket 258 of the reamer guide shaft's locking screw 256 (see FIGS. 21-23) when the finishing rasp 290 is fully seated. In the illustrative embodiment described herein, the depth stop 312 is embodied as a dowel pin welded into a bore formed in the rasp's shaft 292 at an angle transverse to its longitudinal axis. It should be appreciated that other configurations of depth stops may be used, including configurations integral to the rasp's shaft 292.

As can be seen in FIGS. 24 and 25, a number of slotted openings or "viewing windows" 314 are defined in the sidewall 316 of the rasp's shaft 292 that defines the guide bore 306. The viewing windows 314 allow the surgeon to visualize the reamer guide shaft 250 as it is received in the guide bore 306. In doing so, the surgeon can visually confirm that proper seating of the finishing rasp 290 has been achieved by observing the colored mark 280 of the reamer guide shaft 250 through the viewing windows 314 formed in the finishing rasp 290. Specifically, as can be seen in the elevation view of FIG. 24, the outer surface of the rasp's shaft 292 has colored mark 318 formed therein. The colored mark 318 extends around the outer circumference of the shaft 292 and intersects the viewing windows 314. Like the colored mark 280 of the reamer guide shaft 250, the colored mark 318 may be embodied as a groove that is engraved in the outer surface of the rasp's shaft 292 and filled with an epoxy ink of a predetermined color, or, alternatively, may be embodied as a laser mark. In the illustrative embodiment described herein, the colored mark 318 is black. The surgeon may visually confirm that proper seating of the finishing rasp 290 has been achieved when the colored mark 280 of the reamer guide shaft 250 (which is visible through the viewing windows 314) aligns with the colored mark 318 of the finishing rasp 290.

In the illustrative embodiment described herein, the finishing rasp 290 is designed as a finishing tool that removes modest amounts of bone tissue. As such, unlike the other instruments described herein, the handle 294 is irremovably secured to the proximal end 296 of the rasp's shaft 292, for example by welding. Such an arrangement prevents the finishing rasp 290 from being coupled to a power tool. In other arrangements, it may be desirable to implement a powered version of a rasp. In such a case, a removable handle, such as the manual handle 80 of FIG. 8 may be employed.

The finishing rasp 290 may be constructed from a medical-grade metal such as stainless steel, cobalt chrome, or titanium, although other metals or alloys may be used. Moreover, in some embodiments, rigid polymers such as polyetheretherketone (PEEK) may also be used.

Figure 26:
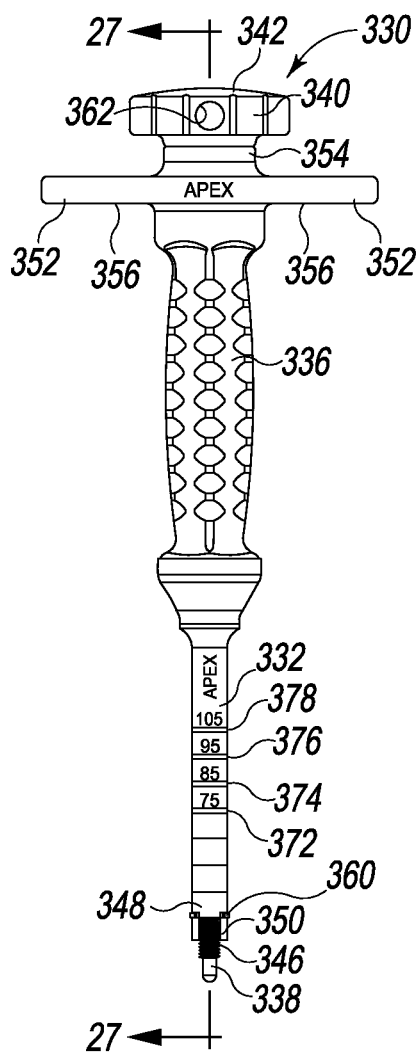
FIG. 26 is an elevation view of the stem insertion tool used to surgically implant the distal stem component into the femur of the patient during performance of a hip revision procedure.
Figure 27:
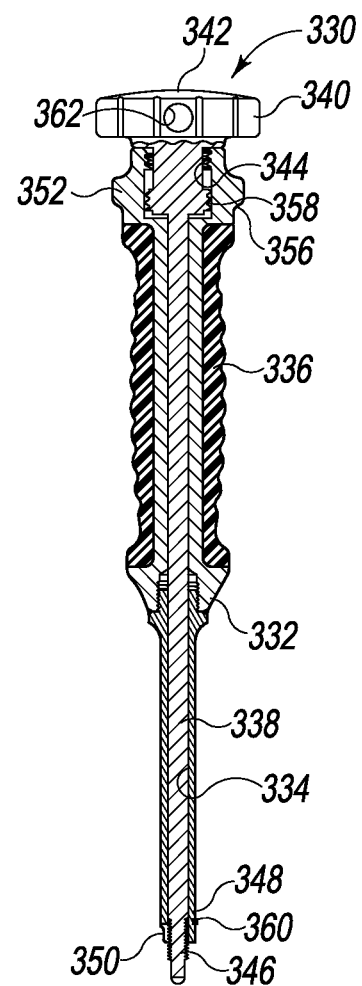
FIG. 27 is a cross sectional view of the stem insertion tool taken along the line 27-27 of FIG. 26, as viewed in the direction of the arrows.

Referring now to FIGS. 26 and 27, there is shown a stem insertion tool 330. The stem insertion tool 330 may be secured to the distal stem component 14 to facilitate implantation of the distal stem component 14 into the intramedullary canal 22 of the patient's femur 20. The stem insertion tool 330 includes a body 332 having an elongated bore 334 extending therethrough. A sleeve 336 is positioned around the insertion tool's body 332. The sleeve 336 is immovably coupled to the outer surface of the insertion tool's body 332, such as by, for example, overmolding. The sleeve 336 functions as a grip for allowing the surgeon to hold the stem insertion tool during implantation of the distal stem component 14.

A locking rod 338 is captured in the bore 334. A knob 340 is secured to the proximal end of the locking rod 338. In addition to being used to secure the stem insertion tool 330 to the distal stem component 14, the knob 340 is also used as an impact surface. Namely, the surgeon strikes the superior surface 342 of the knob 340 to drive the distal stem component 14 into the bone tissue within the intramedullary canal 22 of the patient's femur 20. As can be seen in FIGS. 26 and 27, the knob 340 has a number of holes 362 formed therein. A rod or other type of handle (not shown) may be inserted into the holes 362 to increase the surgeon's leverage during rotation of the knob 340.

As can be seen in the cross section of FIG. 27, a set of internal threads 344 formed in the body 332 within the bore 334 and a set of external threads 358 on the locking rod 338 allow the locking rod 338 to be maintained with the bore 334 while also allowing the stem insertion tool 330 to be disassembled for cleaning between uses.

The locking rod 338 has a set of locking threads 346 formed in its distal end. The threads 346 are sized to be received into the upper threads 40 of the distal stem component 14 (see FIG. 6). As alluded to above, the upper threads 40 are used to couple the distal stem component 14 to the stem insertion tool 330 and any other surgical instrument that is impacted during use thereof. As such, a set of threads that are not used in assembly of the locking bolt 504 to the femoral prosthesis 10 (i.e., the upper threads 40) are subjected to the loads associated with impaction of the stem insertion tool 330 by the surgeon. In doing so, the set of threads used in assembly of the locking bolt 504 to the femoral prosthesis 10 (i.e., the lower threads 42), are not subjected to the loads associated with impaction of the stem insertion tool 330 by the surgeon. Such "thread preservation" ensures the stem component's threads that received the locking bolt 504 (i.e., the lower threads 42) are unharmed by the stem insertion process. In other words, by not subjecting the lower threads 42 to surgical instruments that are impacted during implantation of the femoral prosthesis 10, the threads ultimately used to secure the prosthesis's locking bolt 504 (i.e., the lower threads 42) are protected from damage during the surgical procedure. As noted above, the upper threads 40 of the distal stem component 14 are M8 size threads, whereas the lower threads 42 are M6 size threads. As such, the locking threads 346 of the insertion tool 330 are M8 size threads. By being a larger thread size (e.g., M8 vs. M6), the locking threads 346 of the stem insertion tool 330 cannot inadvertently be driven into the lower threads 42 of the distal stem component 14.

The distal end 348 of the body 332 of the stem insertion tool 330 has an alignment notch 350 formed therein. The alignment notch 350 is sized and shaped to closely complement the size and shape of the alignment key 44 extending superiorly from the superior surface of the body 38 of the distal stem component 14 (see FIG. 4). As mentioned above, the alignment key 44 aligns with the apex of the distal stem component 14. During attachment of the stem insertion tool 330 to the distal stem component 14, the alignment key 44 is received into the alignment notch 350 formed in the insertion tool's body 332.

The distal end 348 of the body 332 of the stem insertion tool 330 has an retaining flange 360 secured thereto. The retaining flange 360 extends around a portion of the outer periphery of the body 332. As will be discussed below in greater detail, the retaining flange 360 prevents the taper-protecting sleeve 380 from inadvertently being dislodged from the distal stem component 14 during use of the stem insertion tool 330.

A pair of impact wings 352 extend outwardly from the proximal end 354 of the body 332 of the stem insertion tool 330. In the illustrative embodiment described herein, the impact wings 352 are integrally formed with the body 332 of the insertion tool 330. As described above, during implantation of the distal stem component 14, the surgeon strikes the superior surface 342 of the knob 340 to drive the distal stem component 14 into the bone tissue within the intramedullary canal 22 of the patient's femur 20 (i.e., drive the distal stem component 14 in the inferior direction). If the surgeon needs to reposition or remove the distal stem component 14 from the intramedullary canal 22 of the patient's femur 20 (with the distal stem component 14 still secured thereto), the surgeon strikes the underside 356 of the impact wings 352 (i.e., the inferior side of the impact wings 352). Such an impact drives the stem insertion tool 330 (and hence the distal stem component 14 attached thereto) in the superior direction thereby allowing it to be removed from, or repositioned within, the intramedullary canal 22 of the patient's femur 20.

Once the surgeon has positioned the distal stem component 14 in the intramedullary canal 22 of the patient's femur 20, the stem insertion tool 330 may be disconnected from the distal stem component 14 by rotating the knob 340 to release the locking threads 346 from the upper threads 40 of the distal stem component 14.

The stem insertion tool 330 includes a number of colored depth marks 372, 374, 376, 378 formed on its body 332. Like the depth marks 72, 74, 76, 78 of the starter reamer 60, the depth marks 172, 174, 176, 178 of the extension tool 120, and the depth marks 272, 274, 276, 278 of the reamer guide shaft 250, each of the colored depth marks 372, 374, 376, 378 corresponds to the standard head center of one of the various proximal body components 12. For example, as described above, the proximal body component 12 may be provided in four different superior/inferior lengths—75 mm, 85 mm, 95 mm, and 105 mm. In the exemplary embodiment described herein, the depth mark 372 is blue and corresponds to the location of the center of the head of a 75 mm proximal body component 12, the depth mark 374 is green and corresponds to the location of the center of the head of a 85 mm proximal body component 12, the depth mark 376 is yellow and corresponds to the location of the center of the head of a 95 mm proximal body component 12, and the depth mark 378 is red and corresponds to the location of the center of the head of a 105 mm proximal body component 12. The depth marks 372, 374, 376, 378 may be embodied as grooves engraved in the body 332 of the stem insertion tool 330, each of which is filled with an epoxy ink of the corresponding color. During a surgical procedure, the stem insertion tool 330, with the distal stem component 14 secured thereto, is advanced deeper into the intramedullary canal 22 of the patient's femur 20 until the desired depth mark aligns with the tip 82 of the greater trochanter 84 (see FIG. 51). In such a way, the desired implant depth of the distal stem component 14 can be achieved.

The metallic components of the stem insertion tool 330 (e.g., the insertion tool's body 332, locking rod 338, etcetera) may be constructed from a medical-grade metal such as stainless steel, cobalt chrome, or titanium, although other metals or alloys may be used. Moreover, in some embodiments, rigid polymers such as polyetheretherketone (PEEK) may also be used. The grip 336 may be constructed from a polymer such as silicone.

Figure 28:
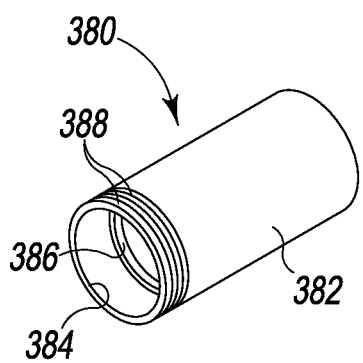
FIG. 28 is a perspective view of the taper-protecting sleeve used to protect the taper of the distal stem component during performance of a hip revision procedure.
Figure 29:
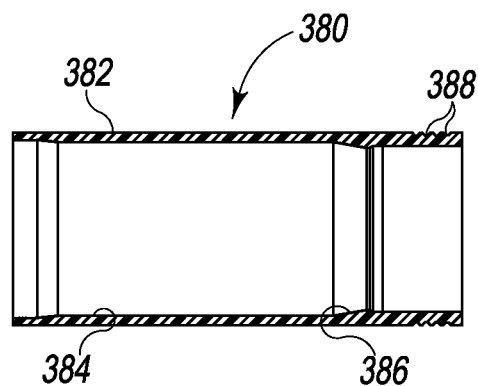
FIG. 29 is an enlarged cross sectional view of the taper-protecting sleeve of FIG. 28.

Referring now to FIGS. 28 and 29, there is shown a taper-protecting sleeve 380. In the illustrative embodiment described herein, the taper-protecting sleeve 380 is packaged with the distal stem component 14. The taper-protecting sleeve 380 is installed on the tapered post 30 formed in the superior end of the distal stem component 14 (see FIGS. 50-52). As described above, the tapered post 30 of the distal stem component 14 is received into the tapered bore 28 of the proximal body component 12 with an applied compressive force taper locking the tapers of the two components together. The taper-protecting sleeve 380 reduces, or even eliminates, potential damage to the outer surfaces of the tapered post 30 of the distal stem component 14 during the surgical process thereby enhancing the integrity of the taper lock between the distal stem component 14 and the proximal body component 12. The taper-protecting sleeve 380 includes a cannulated body 382 having an elongated bore 384 extending therethrough.

A beveled edge 386 located in the elongated bore 384 divides the taper-protecting sleeve 380 into a superior portion and an inferior portion. When the taper-protecting sleeve 380 is assembled to the body 38 of the distal stem component 14, the proximal start of the beveled edge 386 of the taper-protecting sleeve 380 engages the proximal surface of the tapered post 30 of the distal stem component 14. During such assembly, the portion of the body 382 of the taper-protecting sleeve 380 that defines the distal end of the elongated bore 384 also engages the distal surface of the tapered post 30 of the distal stem component 14. As such, the superior portion of the taper-protecting sleeve 380 sits above the superior surface of the body 38 of the distal stem component 14. In such a way, the superior portion of the taper-protecting sleeve 380 functions as a grip to be grabbed or otherwise engaged by forceps or other instrument to facilitate removal of the taper-protecting sleeve 380 after its use. The outer surface of the superior portion of the taper-protecting sleeve 380 includes a number of ribs 388. The ribs 388 provide an engagement surface for the forceps during removal of the taper-protecting sleeve 380.

As alluded to above, the taper-protecting sleeve 380 is packaged with the distal stem component 14. As a result, it is provided to the surgeon in a sterile package, along with the distal stem component 14. The taper-protecting sleeve 380 may be pre-installed on the distal stem component 14 and, as a result, provided to the surgeon in the same sterile package as the distal stem component 14. Alternatively, the taper-protecting sleeve 380 may be provided to the surgeon in a separate sterile package from the sterile package that includes the distal stem component 14. In such a case, the surgeon removes the taper-protecting sleeve 380 from the separate package and installs it onto the distal stem component 14 prior to implantation thereof.

The taper-protecting sleeve 380 may be made of any suitable material, including medical-grade polymeric material. Examples of such polymeric materials include polyethylene such as ultrahigh molecular weight polyethylene (UHMWPE) or polyetheretherketone (PEEK). In such a configuration, the taper-protecting sleeve 380 may be used as a disposable instrument.

Referring now to FIGS. 30-32, there is shown the proximal reamer 390 in more detail. The proximal reamer 390 is used to surgically prepare the patient's femur 20 for implantation of the proximal body component 12. As will be discussed below in regard to FIG. 48, operation of the proximal reamer 390 is performed over the distal stem component 14 to ensure final seating height and stem biomechanics. In some embodiments, operation of the proximal reamer 390 may also be performed over the distal reamer 90 when the distal reamer 90 is positioned in the patient's femur 20.

Like the other instruments and implants described herein, the proximal reamer 390 may be provided in a number of different sizes. For example, proximal reamer 390 may be provided in various diameters to accommodate the various different configurations of the proximal body components 12. In one illustrative embodiment, the proximal reamer 390 may be provided with 20 mm, 24 mm, and 28 mm cutting head diameters.

The proximal reamer 390 includes an elongated shaft 392 having a proximal end 394 that fits into the chuck of a rotary power tool 86 (see FIG. 53) or a manual handle 80 (see FIG. 8). The proximal reamer 390 also includes a cutting head 396 located at the opposite, distal end 398 of the shaft 392. The cutting head 396 of the proximal reamer 390 includes a plurality of helical cutting flutes 402. When the proximal reamer 390 is positioned in the patient's femur 20 and rotated, the cutting flutes 402 ream or otherwise cut the bone tissue of the femur 20 to form a surgically-created cavity to accommodate the geometry of the proximal body component 12. The cutting head 396 is generally cylindrical or conical in shape. The center line of the cutting head 396 and the longitudinal axis of the proximal reamer 390 lie on the same line. As can be seen in FIGS. 30 and 31, the lead cutting edge 404 of the cutting flutes 402 extends beyond the distal end 398 of the shaft 392.

The shaft 392 of the proximal reamer 390 has a blind guide bore 406 formed therein. As can be seen in the cross sectional view of FIG. 32, the distal end 408 of the guide bore 406 is defined in (i.e., opens through) the distal end 398 of the shaft 392 of the proximal reamer 390 at a location proximate to the cutting head 396. The opposite, proximal end 410 of the guide bore 406 is located near the proximal end 394 of the reamer's elongated shaft 392. The center line of the guide bore 406 and the longitudinal axis of the proximal reamer 390 lie on the same line.

A depth stop 412 is located in the proximal end 410 of the guide bore 406. The depth stop 412 bottoms out on the superior surface 282 of the drive socket 258 of the locking screw 256 of the reamer guide shaft 250 (see FIGS. 22 and 23) when the proximal reamer 390 is fully seated. In the illustrative embodiment described herein, the depth stop 412 is embodied as a dowel pin welded into a bore formed in the reamer's shaft 392 at an angle transverse to its longitudinal axis. It should be appreciated that other configurations of depth stops may be used, including configurations integral to the reamer's shaft 392.

As can be seen in FIGS. 30-32, a number of slotted openings or "viewing windows" 414 are defined in sidewall 416 of the reamer's shaft 392 that defines the guide bore 406. The viewing windows 414 allow the surgeon to visualize the reamer guide shaft 250 as it is received in the guide bore 406. In doing so, the surgeon can visually confirm that proper seating of the proximal reamer 390 has been achieved by observing the colored mark 280 of the reamer guide shaft 250 through the viewing windows 414 formed in the proximal reamer 390. Specifically, as can be seen in the elevation view of FIG. 30, the outer surface of the reamer's shaft 392 has colored mark 418 formed therein. The colored mark 418 extends around the outer circumference of the shaft 392 and intersects the viewing windows 414. Like the colored mark 280 of the reamer guide shaft 250, the colored mark 418 may be embodied as a groove that is engraved in the outer surface of the reamer's shaft 392 and filled with an epoxy ink of a predetermined color, or, alternatively, may be embodied as a laser mark. In the illustrative embodiment described herein, the colored mark 418 is black. The surgeon may visually confirm that proper seating of the proximal reamer 390 has been achieved when the colored mark 280 of the reamer guide shaft 250 (which is visible through the viewing windows 414) aligns with the colored mark 418 of the proximal reamer 390.

A male connector 420 is formed in the proximal end 394 of the reamer's shaft 392. The connector 420 fits into the chuck of a rotary power tool 86 (see FIG. 53) or a manual handle 80 (see FIG. 8) to couple the proximal reamer 390 to a rotary drive source.

The proximal reamer 390 includes a number of colored depth marks 422, 424, 426, 428 formed on its body 392. Like the depth marks 72, 74, 76, 78 of the starter reamer 60, the depth marks 172, 174, 176, 178 of the extension tool 120, the depth marks 272, 274, 276, 278 of the reamer guide shaft 250, and the depth marks 372, 374, 376, 378 of the stem insertion tool 330, each of the colored depth marks 422, 424, 426, 428 corresponds to the standard head center of one of the various proximal body components 12. For example, as described above, the proximal body component 12 may be provided in four different superior/inferior lengths—75 mm, 85 mm, 95 mm, and 105 mm. In the exemplary embodiment described herein, the depth mark 422 is blue and corresponds to the location of the center of the head of a 75 mm proximal body component 12, the depth mark 424 is green and corresponds to the location of the center of the head of a 85 mm proximal body component 12, the depth mark 426 is yellow and corresponds to the location of the center of the head of a 95 mm proximal body component 12, and the depth mark 428 is red and corresponds to the location of the center of the head of a 105 mm proximal body component 12. The depth marks 422, 424, 426, 428 may be embodied as grooves engraved in the body 392 of the proximal reamer 390, each of which is filled with an epoxy ink of the corresponding color.

The proximal reamer 390 may be constructed from a medical-grade metal such as stainless steel, cobalt chrome, or titanium, although other metals or alloys may be used.

Referring now to FIGS. 33 and 34, there is shown a trial insertion tool 430. The trial insertion tool 430 may be used to clasp the proximal trial instrument 180 to facilitate its attachment to the distal reamer 90 or the distal stem component 14 implanted in the intramedullary canal 22 of the patient's femur 20. The trial insertion tool 430 is similar to a pair of surgical scissors or a surgical clamp in that it includes a pair of levers 432 pivoted together with a pivot pin 434. A proximal end of each of the levers 432 has a handle or loop 436 secured thereto. The distal end of the levers 432 cooperate to form a cylindrically-shaped retention socket 442. The retention socket 442 is sized and shaped to receive the stem 204 formed in the proximal end 202 of the trial shaft 182. In particular, as shown in the elevation view of FIG. 35, the retention socket 442 has a recess 444 formed therein. The recess 444 is sized to closely mimic the size of the outer surface of the stem 204 of the trial shaft 182 so as to receive it therein. As can also be seen in the elevation view of FIG. 35, the recess 444 is configured with a "tri-lobe" geometry to ensure that the retention socket 442 firmly engages the trial shaft 182.

When a surgeon urges the two loops 436 away from one another, the levers 432 pivot about the pin 434 and the two halves of the retention socket 442 spread slightly away from one another. The stem 204 of the trial shaft 182 may then be advanced into the recess 444 of the retention socket 442. Thereafter, the surgeon may squeeze or otherwise urge the two loops 436 toward one another thereby causing the levers 432 to pivot about the pin 434 toward one another. Doing so urges the two halves of the retention socket 442 toward one another thereby squeezing the stem 204 of the trial shaft 182 so as to retain the trial shaft 182 in the retention socket 442. As can be seen in FIG. 33, each of the levers 432 of the trial insertion tool 430 has a number of ratchet teeth 446 formed therein at a location between the loops 436. The ratchet teeth 446 allow the surgeon to lock the levers 432 in a position in which the trial shaft 182 is locked in the retention socket 442.

The trial insertion tool 430 may be constructed from a medical-grade metal such as stainless steel, cobalt chrome, or titanium, although other metals or alloys may be used.

Referring now to FIGS. 36-39, there is shown a version-replicating instrument 460. As will be discussed below in more detail in regard to FIGS. 58-61, the version-replicating instrument 460 may be used to ensure that the version of the implanted proximal body component 12 replicates the version that was determined by use of the proximal trial instrument 180 during trialing.

The version-replicating instrument 460 includes an elongated shaft 462 having an alignment stem 464 extending from its distal end 466. In the illustrative embodiment described herein, the version-replicating instrument 460 is embodied as a monolithic component. Hence, the alignment stem 464 is integrally formed with the elongated shaft 462. An alignment key 468 in the form of, for example, a rib extends outwardly from the alignment stem 464. The longitudinal axis of the alignment key 468 extends in the superior/inferior direction. The alignment key 468 is configured to mate with the keyway 46 formed in the superior surface of the body 38 of the distal stem component 14 (see FIG. 4). In the exemplary embodiment described herein, the cross-sectional shape of the alignment key 468 is lobe shaped to compliment the shape of the stem component's keyway 46. In such a way, the alignment key 468 is identical to the alignment key 214 formed on the distal end 212 of the trial shaft 182 of the proximal trial instrument 180 (see FIGS. 14-16).

As shown in the cross sectional view of FIG. 39, the version-replicating instrument's shaft 462 has a countersunk blind hole 470 formed in its proximal end 472. The shaft's proximal end 472 also has an alignment slot 474 formed therein. Like the alignment key 468, the longitudinal axis of the alignment slot 474 extends in the superior/inferior direction. The proximal end 476 of the alignment slot 474 is open, with its distal end 478 being closed in the shaft 462. As can be seen in the cross sectional view of FIG. 39, the alignment slot 474 opens into the hole 470 formed in the shaft 462.

As can be seen in FIG. 36, the version-replicating instrument's alignment slot 474 is aligned with its alignment key 468. In particular, the longitudinal axis of the alignment slot 474 and the longitudinal axis of the alignment key lie on the same imaginary line 480.

As will be discussed below in more detail in regard to FIGS. 58-61, during a surgical procedure to taper lock the proximal body component 12 to the implanted distal stem component 14, the distal end 212 of the trial shaft 182 of the proximal trial instrument 180 (see FIGS. 14-16) is inserted into the blind hole 470 formed in the proximal end of the version-replicating instrument's shaft 462. In doing so, the alignment key 214 formed on the trial shaft 182 of the proximal trial instrument 180 is received into the alignment slot 474 formed in the version-replicating instrument's shaft 462.

Like many of the other instruments described herein, the version-replicating instrument 460 includes a number of colored depth marks 482, 484, 486, 488 formed on the outer surface of its shaft 462. Unlike the other depth marks described herein (e.g., the depth marks 72, 74, 76, 78 of the starter reamer 60, the depth marks 172, 174, 76, 178 of the extension tool 120, etcetera), each of the colored depth marks 482, 484, 486, 488 does not correspond to the standard head center of one of the various proximal body components 12, but rather corresponds to the location of the shoulder 52 of the one of the various proximal body components 12 (see FIG. 2). For example, as described above, the proximal body component 12 may be provided in four different superior/inferior lengths—75 mm, 85 mm, 95 mm, and 105 mm. In the exemplary embodiment described herein, the depth mark 482 is blue and corresponds to the location of the shoulder 52 of a 75 mm proximal body component 12, the depth mark 484 is green and corresponds to the location of the shoulder 52 of a 85 mm proximal body component 12, the depth mark 486 is yellow and corresponds to the location of the shoulder 52 of a 95 mm proximal body component 12, and the depth mark 488 is red and corresponds to the location of the shoulder 52 of a 105 mm proximal body component 12. The depth marks 482, 484, 486, 488 may be embodied as grooves engraved in the shaft 462 of the version-replicating instrument 460, each of which is filled with an epoxy ink of the corresponding color.

The version-replicating instrument 460 may be constructed from a medical-grade metal such as stainless steel, cobalt chrome, or titanium, although other metals or alloys may be used. Moreover, in some embodiments, rigid polymers such as polyetheretherketone (PEEK) may also be used.

Referring now to FIGS. 40-43, there is shown a stem stabilizer 490. The stem stabilizer 490 may be secured to the proximal body component 12 to prevent the implanted modular femoral prosthesis 10 from rotating during installation of the locking bolt 504 (see FIGS. 64-66). The stem stabilizer 490 includes a body 492 having an elongated bore 494 extending therethrough. A drive rod 514 is captured in the bore 494. A square-type drive head 496 is formed in the proximal end of the drive rod 514, with a drive socket 498 being formed in its opposite, distal end. The drive socket 498 is sized to receive the head 502 of the locking bolt 504 (see FIG. 64). As such, rotation of the drive head 496 of the drive rod 514 causes rotation of the drive socket 498 and hence the head 502 of the locking bolt 504 positioned therein.

Figure 40:
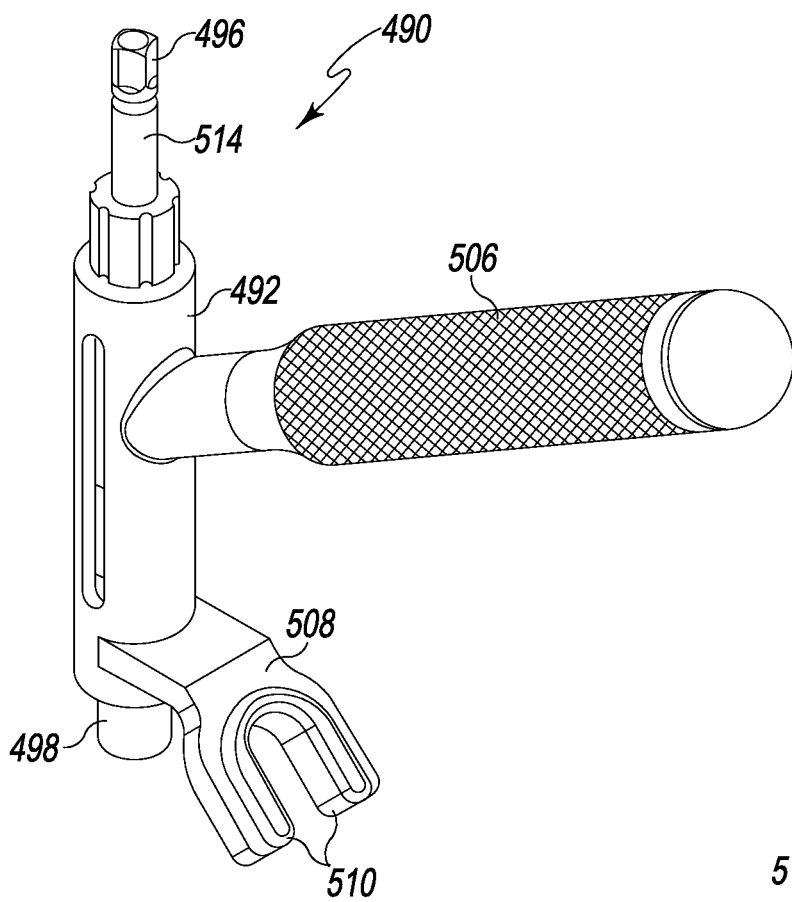
FIG. 40 is a perspective view of the stem stabilizer used during performance of a hip revision procedure.
Figure 41:
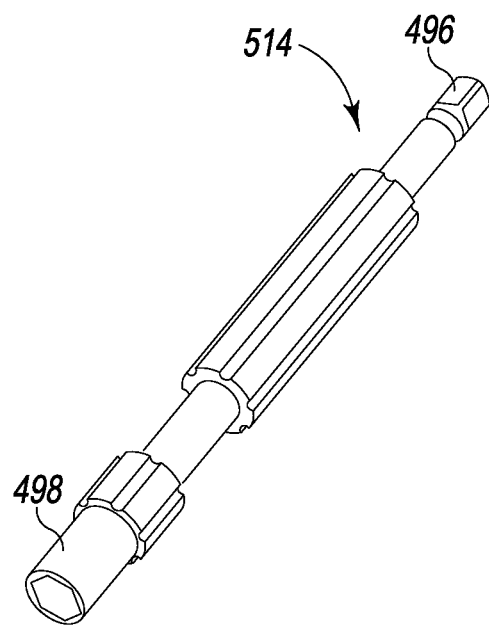
FIG. 41 is an enlarged perspective view of the drive rod of the stem stabilizer of FIG. 40.
Figure 43:
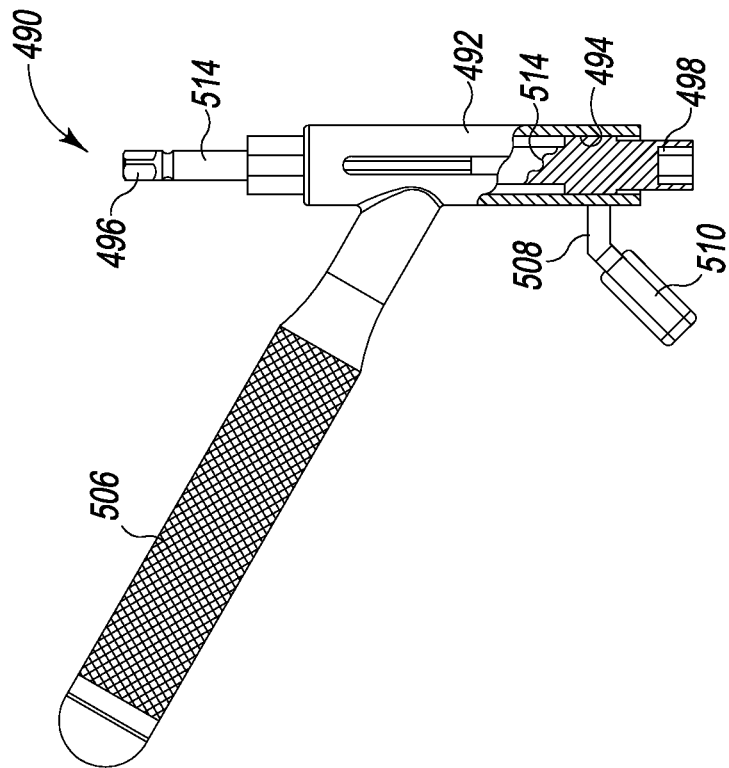
FIG. 43 is a view similar to FIG. 42, but showing a portion of the stem stabilizer in cross section for clarity of description.
Figure 42:
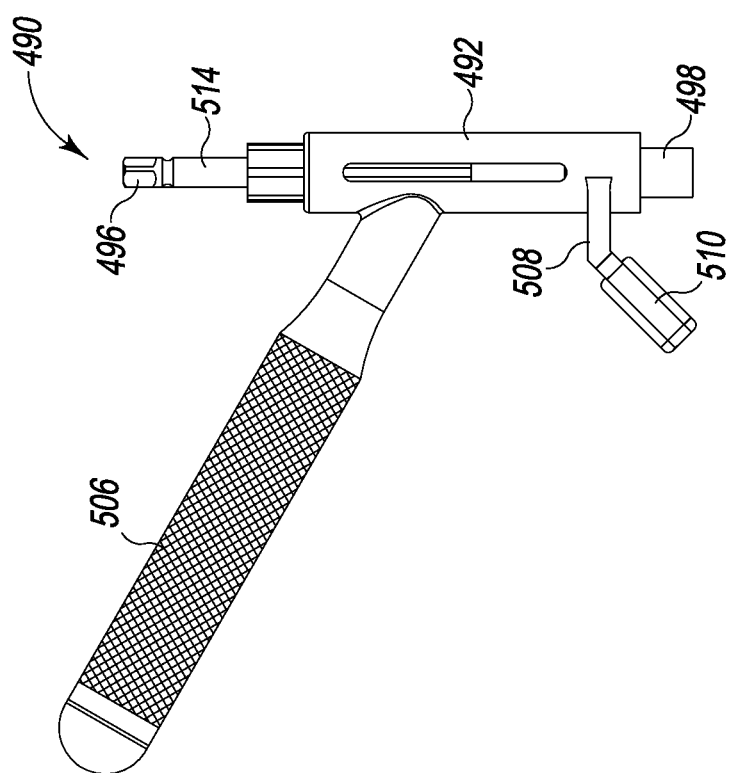
FIG. 42 is a side elevation view of the stem stabilizer of FIG. 40.

As shown in FIGS. 40 and 42, a handle 506 extends upwardly away from the body 492 of the stem stabilizer 490. A surgeon holds onto the handle 506 to prevent rotation of the stem stabilizer 490 (and hence corresponding rotation of the proximal body component 12) during installation of the locking bolt 504. As can be seen in FIGS. 40 and 42, the handle 506 has a knurled outer surface. Such a textured surface increases the surgeon's ability to grip the handle 506, particularly in the presence of the fluids commonly present during a surgical procedure.

A fork 508 extends away from the body 492 of the stem stabilizer 490 in a generally downward direction. As will be discussed below in regard to FIGS. 64-66, the elongated neck 16 of the proximal body component 12 is captured between the tines 510 of the fork 508 when the stem stabilizer 490 is installed on the implanted modular femoral prosthesis 10. As such, when the surgeon prevents the stem stabilizer from rotating during installation of the locking bolt 504, the implanted modular femoral prosthesis 10 is likewise prevented from rotating by virtue of having the elongated neck 16 of the proximal body component 12 captured in the fork 508. The tines 510 of the fork 508 may be coated or otherwise covered with a non-metal (e.g., radel) cap to prevent damage to the elongated neck 16 of the proximal body component 12.

The stem stabilizer 490 may be constructed from a medical-grade metal such as stainless steel, cobalt chrome, or titanium, although other metals or alloys may be used.

Referring now to FIGS. 44-66, there is shown a surgical procedure in which the various instruments described herein in regard to FIGS. 7-43 are used to surgically prepare the patient's femur 20 for implantation of the femoral prosthesis 10 of FIGS. 1-6. Typically, the femoral prosthesis 10 is being implanted as part of a revision procedure. As such, the surgical procedure begins with preoperative planning in which, amongst other things, a CT scan or other type of preoperative image may be obtained to plan the removal of the existing femoral implant, along with placement location and orientation of the revision femoral prosthesis 10. With the preoperative planning complete, the patient's soft tissue is dissected and retracted in order to allow access to the hip joint. Full exposure of the patient's existing femoral prosthesis is typically achieved (i.e., the prosthesis that was previously implanted and now being removed and replaced with the femoral prosthesis 10).

Figure 44:
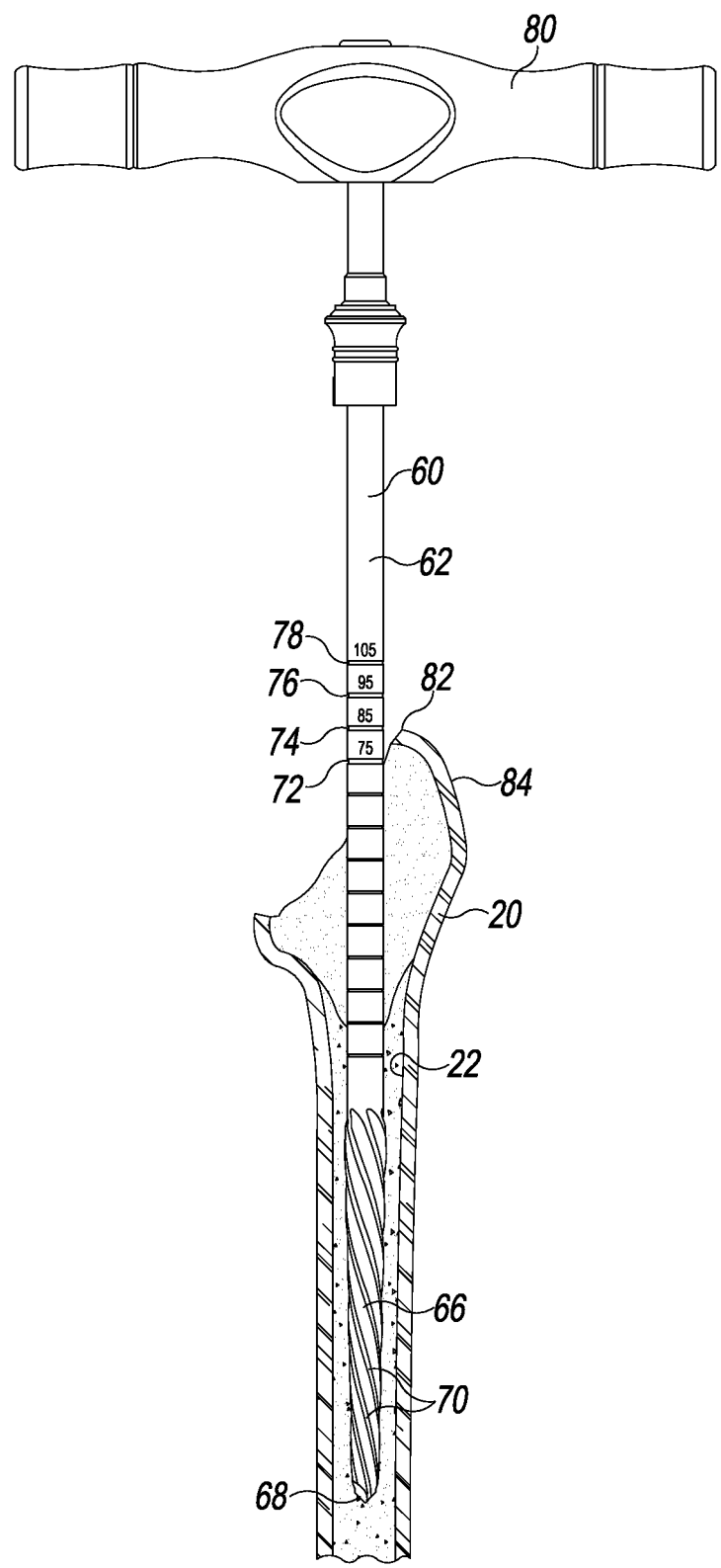
FIG. 44 is a fragmentary elevation view showing the starter reamer being used to ream the intramedullary canal of a patient's femur during performance of a hip revision procedure.

Thereafter, the previous femoral implant is removed. In particular, the surgeon extracts the previous femoral implant thereby leaving an exposed opening in the patient's femur 20 where the previous femoral implant was located. The surgeon then prepares the intramedullary canal 22 of the patient's femur 20 to receive the revision femoral prosthesis 10. Initially, as shown in FIG. 44, the surgeon uses the starter reamer 60 to ream the portion of the patient's intramedullary canal 22 into which the distal stem component 14 is implanted. To do so, the surgeon inserts the proximal end 64 of the starter reamer into the chuck of the manual handle 80 (or, optionally, a rotary power tool 86). The surgeon then positions the cutting head 66 of the starter reamer 60 in the intramedullary canal 22 of the patient's femur 20 and thereafter rotates the handle 80. Such rotation of the handle causes the cutting flutes 70 to ream or otherwise cut the bone tissue of the femur thereby obtaining clear access to the femoral canal. Such access to the intramedullary canal 22 ensures proper alignment of the components of the revision femoral prosthesis 10 during subsequent surgical steps. In the illustrative embodiment described herein, a 140 mm length starter reamer 60 may be used to obtain such clear access to the femoral canal prior to distal reaming.

As described above, each of the colored depth marks 72, 74, 76, 78 on the starter reamer's shank 62 corresponds to the standard head center of a number of different proximal body components 12. For example, the proximal body component 12 may be provided in four different lengths—75 mm, 85 mm, 95 mm, and 105 mm. In the illustrative method described herein, the starter reamer 60 may be seated to the level of the 85 mm proximal body to re-establish the center of rotation of the femoral head. In doing so, one size proximal body shorter and two longer then remain to either increase or decrease leg length. As such, the starter reamer 60 is advanced deeper into the intramedullary canal 22 of the patient's femur 20 until the depth mark 74 (the green depth mark) aligns with the tip 82 of the greater trochanter 84 (see FIG. 44). Having gained clear access to the intramedullary canal 22 of the patient's femur 20, the starter reamer 60 is then removed.

The surgeon next utilizes the distal reamer 90 to ream the portion of the patient's intramedullary canal 22 into which the distal stem component 14 is implanted. The distal reamer 90 produces a bore possessing the final geometry (i.e., the shape) required to accept the distal stem component 14 of the femoral prosthesis 10. Based on the desired diameter and length of the distal stem component 14 determined during a preoperative templating process, the surgeon first selects the appropriate size of the distal reamer 90 to be used. In particular, as discussed above, the distal reamer 90 may be provided in four different lengths—140 mm, 190 mm, 240 mm, and 290 mm—each of which corresponds to one of the available lengths of the distal stem component 14. Such reamers 90 are provided in 1 mm diameter increments ranging from 14 to 31 mm.

Depending on the size of the intramedullary canal 22 of the patient's femur 20, the surgeon selects and attaches a distal reamer 90 having an appropriately sized diameter and length to the extension tool 120. To do so, the surgeon first pulls downwardly (in the orientation of FIG. 13) on the locking lever 158 of the extension tool 120 so as to position the drive spline 126 of the extension tool 120 in its retracted (i.e., unlocked) position. The surgeon then inserts the locking jaws 148 of the extension tool 120 through the open ends of the locking slots 106 of the distal reamer's drive connector 102. The surgeon then rotates the extension tool 120 such that the locking jaws 148 are captured in the locking slots 106 of the distal reamer's drive connector 102. This creates axial stability between the extension tool 120 and the selected distal reamer 90. The surgeon then moves the locking lever 158 to its locked position (as shown in FIG. 13) thereby moving the drive spline 126 to its extended (i.e., locked) position in which it is received into the distal reamer's female drive socket 108. This locks the distal reamer 90 to the extension tool 120 thereby creating rotational stability between the extension tool 120 and the distal reamer 90.

Figure 45:
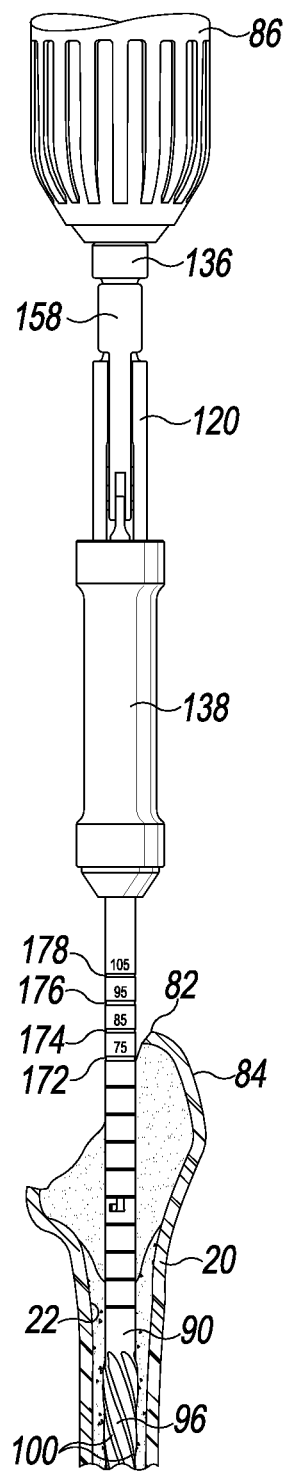
FIG. 45 is a fragmentary elevation view showing the extension tool and the distal reamer being used to ream the intramedullary canal of a patient's femur during performance of a hip revision procedure.

The male connector 134 of the extension tool 120 is then inserted into the chuck of the rotary power tool 86. As shown in FIG. 45, the surgeon then inserts the cutting head 96 of the distal reamer 90 into the intramedullary canal 22 of the patient's femur 20 and activates the power tool 86. The power tool 86 rotates the distal reamer 90 thereby causing its cutting flutes 100 to ream or otherwise cut the bone tissue of the femur 20. The extension tool 120, with the distal reamer 90 secured thereto, is advanced deeper into the intramedullary canal 22 of the patient's femur 20 until the desired depth mark 172, 174, 176, 178 aligns with the tip 82 of the greater trochanter 84.

The initial distal reamer 90 is then removed from the extension tool 120 and the reamer 90 with the next larger diameter and/or length is then attached to the extension tool 120 and the process repeated. The surgeon progressively reams in diameter and/or length with increasingly larger distal reamers 90 until engagement with sufficient cortical bone tissue is achieved (known as "good cortical chatter") and the appropriate depth is obtained.

Figure 46:
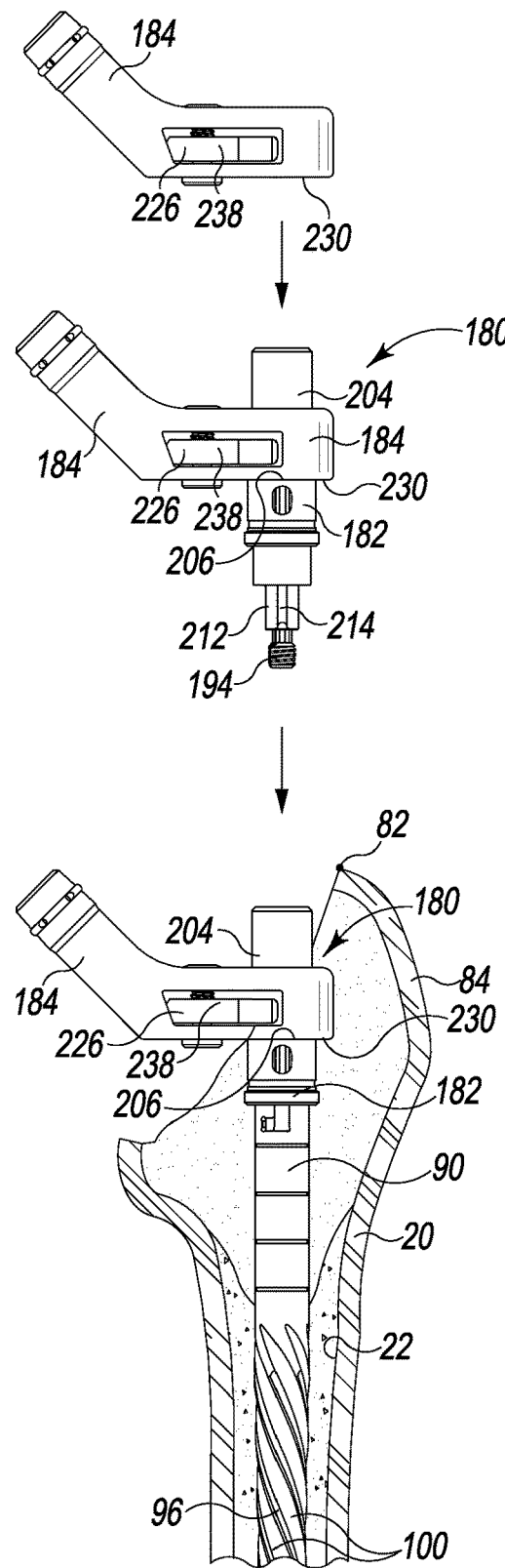
FIG. 46 is a fragmentary elevation view showing the proximal trial instrument coupled to the distal reamer during performance of a hip revision procedure.
Figure 47:
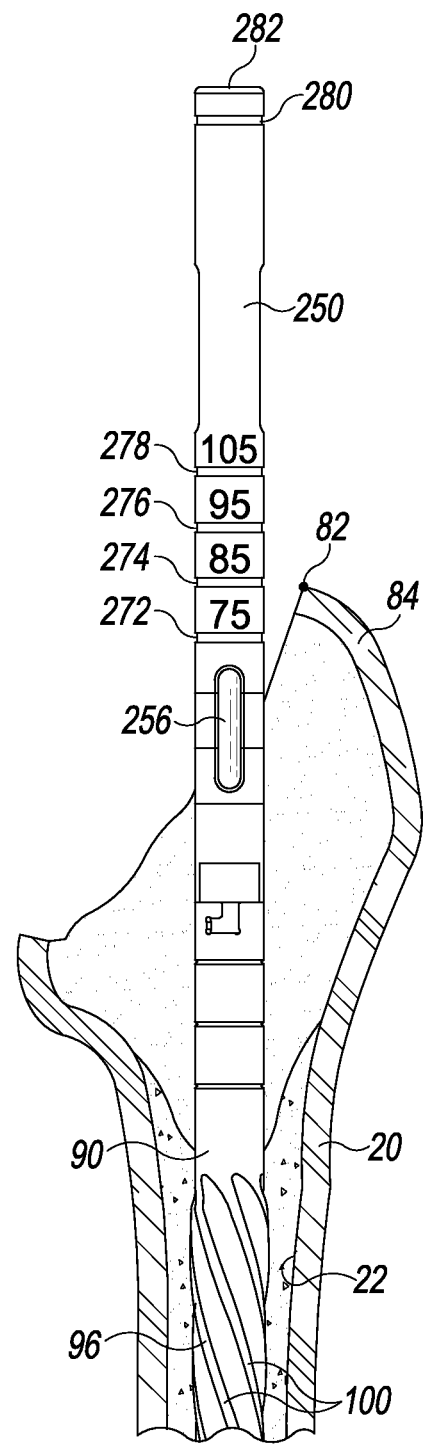
FIG. 47 is a fragmentary elevation view showing the reamer guide shaft coupled to the distal reamer during performance of a hip revision procedure.

Thereafter, the surgeon may opt to perform a trial procedure with use of the distal reamer 90. In particular, if a large proximal deformity exists and traditional bony landmarks are absent, trialing off the distal reamer 90 may be conducted to obtain an early indication of leg length and offset, for example. In such a case, the surgeon pulls the locking lever 158 on the extension tool 120 thereby allowing the extension tool 120 to be decoupled from the distal reamer 90 still positioned in the intramedullary canal 22 of the patient's femur 20. Thereafter, as shown in FIG. 46, the surgeon secures the proximal trial instrument 180 to the distal reamer positioned in the intramedullary canal 22 of the patient's femur 20. Specifically, the surgeon selects a trial shaft 182 which corresponds to the distal reamer depth that was referenced during distal reaming (i.e., based on which depth mark 172, 174, 176, 178) was utilized during reaming. To insert the trial shaft 182, the surgeon uses the trial insertion tool 430. Specifically, the surgeon urges the two loops 436 of the insertion tool 430 away from one another such that the levers 432 pivot about the pin 434 and the two halves of the retention socket 442 spread slightly away from one another. The stem 204 of the trial shaft 182 may then be advanced into the recess 444 of the retention socket 442. Thereafter, the surgeon squeezes or otherwise urges the two loops 436 toward one another thereby causing the levers 432 to pivot about the pin 434. Doing so urges the two halves of the retention socket 442 toward one another thereby squeezing the stem 204 of the trial shaft 182 so as to retain the trial shaft 182 in the retention socket 442.

The distal end of the trial shaft 182 is then inserted into the countersunk drive connector 102 formed in the proximal end 94 of the distal reamer 90. In doing so, the locking threads 194 of the trial shaft 182 are started in the threads 112 of the distal reamer 90. The surgeon then inserts a hex driver 512 (such as the one shown in FIG. 56) into the hex drive head 192 of the trial shaft's locking screw 190. Thereafter, the surgeon rotates the hex driver 512 so as to rotate the locking threads 194 formed in the distal end of the trial shaft's locking screw 190 thereby driving the trial shaft's threads 194 into the threads 112 of the distal reamer 90. It should be appreciated that the hex driver 512 may be embodied as a torque limiting hex driver to prevent over tightening of the locking screw 190.

As shown in FIG. 46, the trial neck 184 may be installed on the trial shaft 182 prior to coupling the trial shaft 182 to the distal reamer 90. If it is not installed beforehand, the trial neck 184 may be installed on the trial shaft 182 after the shaft is coupled to the distal reamer 90. To do so, the surgeon advances the trial neck 184 such that the proximal stem 204 of the trial shaft 182 is received into the bore 228 of the trial neck 184. The trial neck 184 slides down the stem 204 of the trial shaft 182 until the inferior surface 230 of the trial neck's body 224 contacts the shoulder 206 formed in the body 186 of the trial shaft 182 (see also FIGS. 14-17).

At this point, the trial neck 184 is freely movable relative to the trial shaft 182. Upon orientating the trial neck 184 in the proper version, it may be secured in the desired position by inserting a manual universal hex driver 512 (such as the one shown in FIG. 56) in the hex drive head 242 formed in the proximal end of the trial neck's locking screw 240. The surgeon may then tighten the locking screw 240 by rotating the hex driver 512. By doing so, the locking pawl 244 of the trial neck's friction clamp 238 is urged into positioned in one of the grooves of the splined surface 208 of the trial shaft 182. The locking pawl 244 contacts the sidewalls forming the groove of the splined surface 208 thereby preventing the trial neck 184 from rotating relative to the trial shaft 182. It should be appreciated that the hex driver 512 may be embodied as a torque limiting hex driver to prevent over tightening of the locking screw 240.

The surgeon may then install a trial femoral head (not shown) on the trial neck 184 and perform a trial reduction to confirm appropriate leg length, offset, and component orientation. Once the trial reduction is complete, the proximal trial instrument 180 is removed by coupling the trial insertion tool 430 to the trial shaft 182 in the manner described above. The surgeon then inserts the hex driver 512 into the hex drive head 192 of the trial shaft's locking screw 190 and rotates it in the opposite direction it was rotated during installation thereby rotating the locking threads 194 formed in the distal end of the trial shaft's drive shaft 122 in a direction which causes them to exit the threads 112 of the distal reamer 90. The proximal trial instrument 180 may then be removed from the distal reamer 90.

Figure 48:
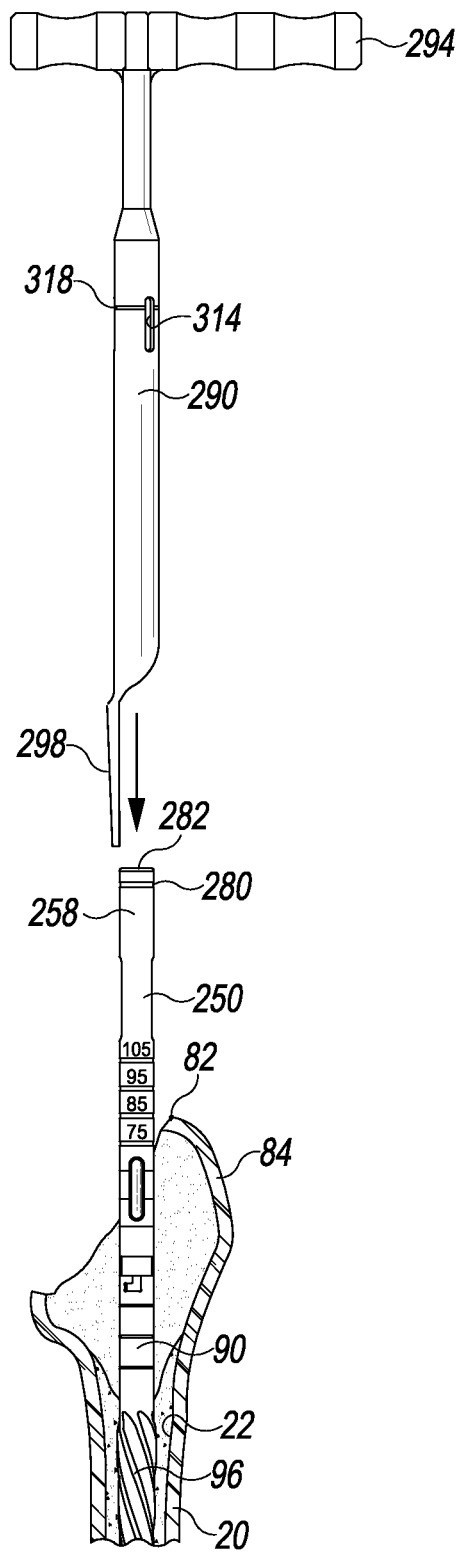
FIGS. 48 and 49 are fragmentary elevation views showing the finishing rasp being used to rasp the patient's femur during performance of a hip revision procedure.
Figure 49:
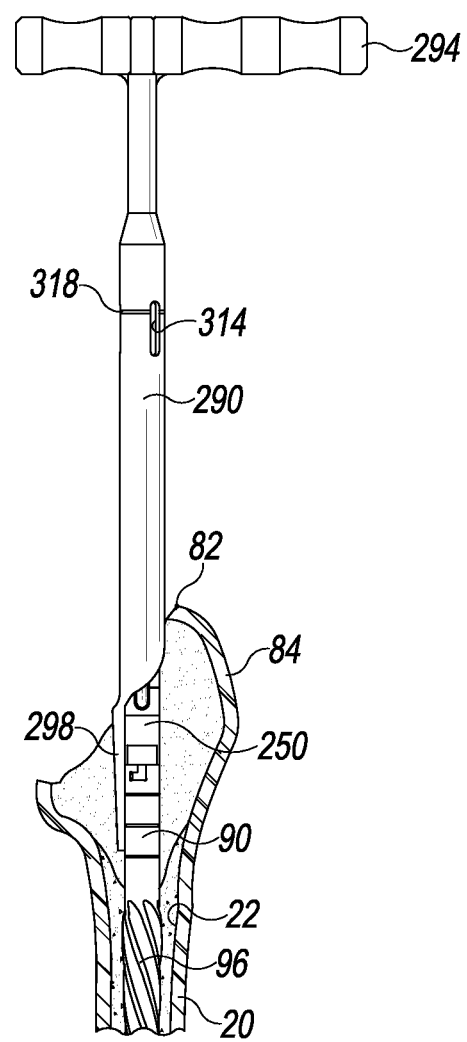

When implanting bowed distal stem components 14 having relatively small diameters (e.g., 14-20 mm) in patients who do not present a large proximal deformity, it may be necessary to utilize the finishing rasp 290. As shown in FIGS. 48 and 49, the surgeon may use the finishing rasp 290 to remove additional bone to facilitate the proper seating of a bowed distal stem component 14. To use the finishing rasp 290, the surgeon first couples the reamer guide shaft 250 to the distal reamer 90 that is still positioned in the intramedullary canal 22 of the patient's femur 20 (see FIG. 47). To do so, the distal end of the reamer guide shaft 250 is positioned on the proximal end 94 of the distal reamer 90. The surgeon then secures the reamer guide shaft 250 to the distal reamer 90 by inserting a manual universal hex driver 512 (such as the one shown in FIG. 56) in the hex drive socket 258 formed in the proximal end of the reamer guide shaft's locking screw 256. The surgeon may then rotate the hex driver to drive the reamer guide shaft's locking screw 256 thereby driving its threads 260 into the threads 112 of the distal reamer 90. It should be appreciated that the hex driver 512 may be embodied as a torque limiting hex driver to prevent over tightening of the locking screw 256.

The surgeon then selects a finishing rasp 290 that has a diameter that corresponds to that diameter of the final distal reamer 90 used during the progressive distal reaming operation (such a size also corresponds to the size of the distal stem component 14 that was preoperatively determined). The surgeon then positions the finishing rasp 290 such that the distal end 308 of its guide bore 306 is located above the proximal end of the reamer guide shaft 250. The finishing rasp 290 is then advanced such that the reamer guide shaft 250 enters the guide bore 306 of the finishing rasp 290. Once inserted over the reamer guide shaft 250, the surgeon uses the handle 294 to oscillate the finishing rasp 290 back and forth through 180° of oscillating motion thereby causing the cutting teeth 304 of the finishing rasp 290 to abrade or otherwise cut the excess bone tissue of the medial cortex in two directions. Thus, a notch possessing the geometry (i.e., the shape) required to accept a bowed distal stem component 14 is gradually created and should be positioned 180° from the planned location of the distal stem component's apex. The finishing rasp's depth stop 312 bottoms out on the superior surface 282 of the drive socket 258 of the reamer guide shaft's locking screw 256 (see also FIGS. 22 and 23) when the finishing rasp 290 is fully seated.

During such use of the finishing rasp 290, the rasp's viewing windows 314 allow the surgeon to visualize the reamer guide shaft 250 as it is advanced along the rasp's guide bore 306. In doing so, the surgeon can visually confirm that proper seating of the finishing rasp 290 has been achieved by observing the colored mark 280 of the reamer guide shaft 250 through the viewing windows 314 formed in the finishing rasp 290. Specifically, the surgeon may visually confirm that proper seating of the finishing rasp 290 has been achieved when the colored mark 280 of the reamer guide shaft 250 (which is visible through the viewing windows 314) aligns with the colored mark 318 of the finishing rasp 290.

Once the rasping operation is complete, the finishing rasp 290 is removed from the reamer guide shaft 250. The reamer guide shaft 250 is then itself removed from the distal reamer 90 by inserting the manual universal hex driver 512 in the hex drive socket 258 formed in the proximal end of the reamer guide shaft's locking screw 256 and rotating the locking screw 256 in the opposite direction it was rotated during installation thereby rotating the locking threads 260 formed in the distal end of the locking screw 256 in a direction which causes them to exit the threads 112 of the distal reamer 90. The reamer guide shaft 250 may then be removed from the distal reamer 90.

The distal reamer may then be removed from the intramedullary canal 22 of the patient's femur 20. To do so, the surgeon couples the extension tool 120 to the distal reamer 90 in the manner described above. Thereafter, the surgeon operates the rotary power tool 86 (or the manual handle 80) to back the distal reamer 90 out of the intramedullary canal 22 of the patient's femur 20.

Once the distal reamer 90 has been removed, the surgeon may then implant the distal stem component 14. To do so, the surgeon first ensures the taper-protecting sleeve 380 is installed on the tapered post 30 formed in the superior end of the distal stem component 14. The taper-protecting sleeve 380 reduces, or even eliminates, potential damage to the outer surfaces of the tapered post 30 of the distal stem component 14 during the subsequent surgical steps thereby enhancing the integrity of the taper lock between the distal stem component 14 and the proximal body component 12. As alluded to above, the taper-protecting sleeve 380 may be pre-installed on the distal stem component 14 by the manufacturer and, as a result, require no additional attention by the surgeon. Alternatively, if the taper-protecting sleeve 380 is provided to the surgeon in a separate sterile package, the surgeon removes the taper-protecting sleeve 380 from the separate package and installs it onto the distal stem component 14 prior to implantation thereof.

Figure 50:
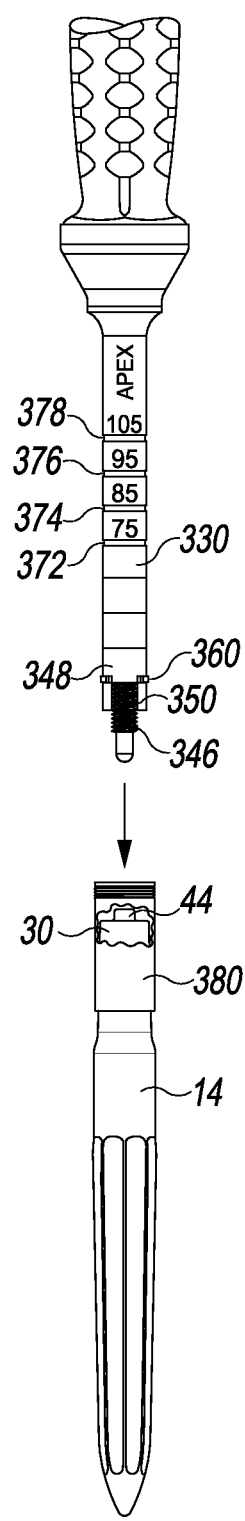
FIG. 50 is a fragmentary elevation view showing the distal stem component being coupled to the stem insertion tool during performance of a hip revision procedure.

Thereafter, as shown in FIG. 50, the distal stem component 14 is coupled to the stem insertion tool 330. The surgeon aligns the stem insertion tool's alignment notch 350 with the alignment key 44 extending superiorly from the superior surface of the body 38 of the distal stem component 14. As described above, the alignment key 44 aligns with the apex of the distal stem component 14. The distal stem component 14 is positioned relative to the stem insertion tool 330 such that the alignment key 44 is received into the alignment notch 350 formed in the insertion tool's distal end.

The surgeon then rotates the knob 340 of the stem insertion tool 330 to drive the locking threads 346 of its locking rod 338 into the upper threads 40 of the distal stem component 14 (see FIG. 6). As alluded to above, the upper threads 40 are used to couple the distal stem component 14 to the stem insertion tool 330 and any other loaded surgical instrument during implantation of the stem component.

Figure 51:
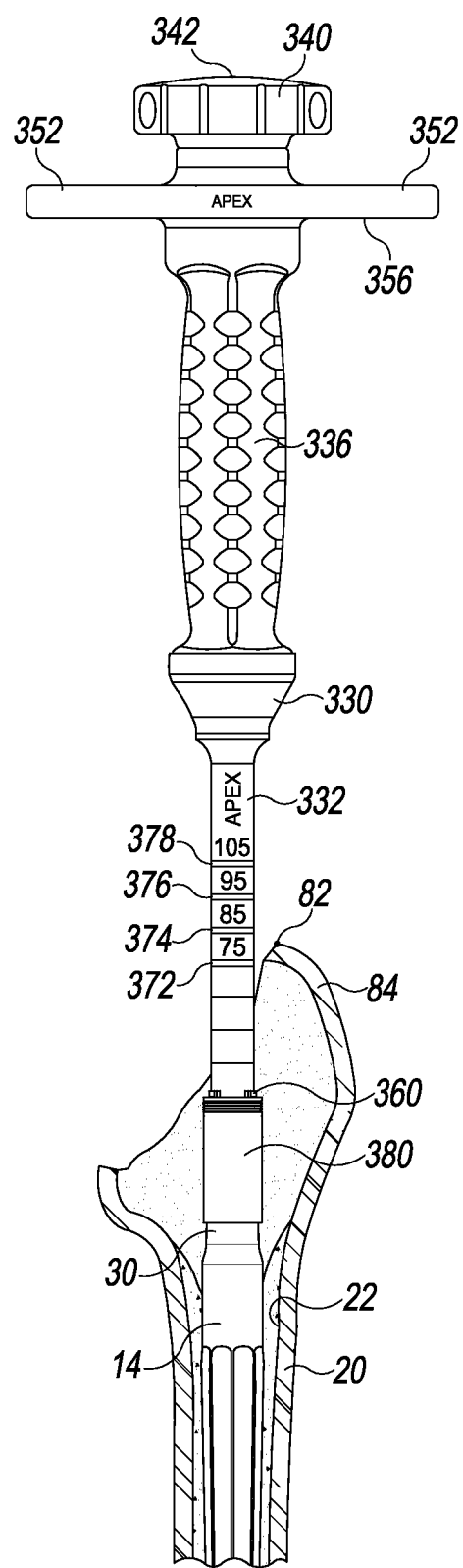
FIG. 51 is a fragmentary elevation view showing the stem insertion tool being used to implant the distal stem component into the intramedullary canal of a patient's femur during performance of a hip revision procedure.
Figure 52:
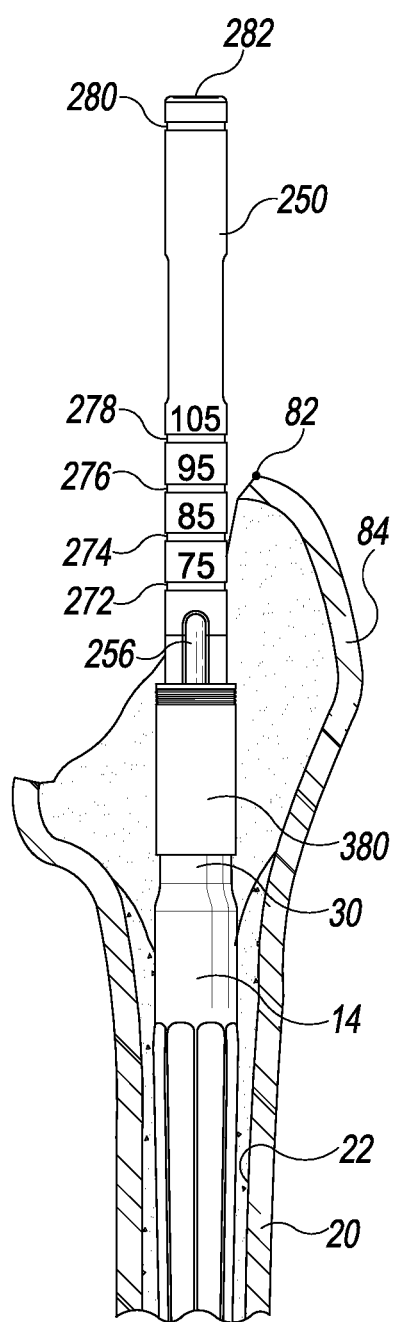
FIG. 52 is a fragmentary elevation view showing the reamer guide shaft secured to the distal stem component during performance of a hip revision procedure.

As shown in FIG. 51, the surgeon then inserts the distal stem component into the intramedullary canal 22 of the patient's femur 20. The surgeon may use a surgical mallet (not shown) to impact the superior surface 342 of the knob 340 to drive the distal stem component 14 into the bone tissue within the intramedullary canal 22 of the patient's femur 20. The surgeon continues to drive the distal stem component 14 deeper into the intramedullary canal 22 of the patient's femur 20 until the desired depth mark 372, 374, 376, 378 of the stem insertion tool 330 aligns with the tip 82 of the greater trochanter 84 (see FIG. 51). During such implantation of the distal stem component, the "APEX" indicia located on the stem insertion tool 330 provides a visual indicator of the location of the apex of the bowed distal stem component 14. In such a way, the surgeon can properly orientate bowed distal stem components 14 in the intramedullary canal 22 of the patient's femur 20.

Once the desired implant depth of the distal stem component 14 has been achieved, the stem insertion tool 330 is removed. To do so, the surgeon rotates the knob 340 of the stem insertion tool 330 in the opposite direction it was rotated during installation thereby rotating the locking threads 346 formed in the distal end of the locking rod 338 in a direction which causes them to exit the upper threads 40 of the distal stem component 14. The surgeon may then remove the stem insertion tool 330 from the intramedullary canal 22 of the patient's femur 20.

With the distal stem component 14 implanted, the surgeon next prepares the patient's femur 20 to receive the proximal body component 12. Although proximal body preparation may be completed over the distal reamer 90, performing it over the implanted distal stem component 14 facilitates final seating height and stem biomechanics. The taper-protecting sleeve 380 remains secured to the tapered post 30 of the distal stem component 14 during proximal body preparation.

Figure 53:
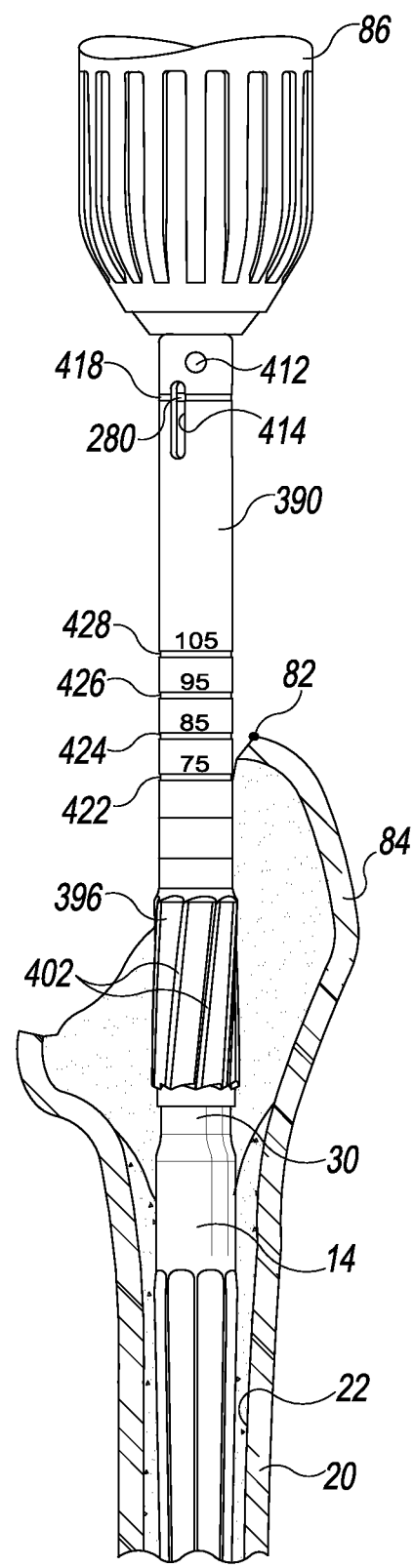
FIG. 53 is a fragmentary elevation view showing the proximal reamer being used to ream the patient's femur during performance of a hip revision procedure.

As shown in FIG. 53, the surgeon may use the proximal reamer 390 to remove additional bone tissue to facilitate the proper seating of proximal body component 12. To use the proximal reamer 390, the surgeon first couples the reamer guide shaft 250 to the implanted distal stem component 14 (see FIG. 52). To do so, the surgeon aligns the reamer guide shaft's alignment flat 264 with the alignment key 44 extending superiorly from the superior surface of the body 38 of the distal stem component 14. In doing so, the reamer guide shaft 250 is positioned relative to the distal stem component 14 such that the reamer guide shaft's alignment key 284 is aligned with, and received into, the keyway 46 formed in the superior surface of the distal stem component 14 (see FIG. 4) thereby inserting the distal end of the reamer guide shaft 250 into the opening formed by the distal stem component's upper threads 40. As a result, the locking threads 260 of the reamer guide shaft 250 are started in the lower threads 42 of the distal stem component 14. The surgeon then locks the reamer guide shaft 250 to the distal stem component 14 by inserting a manual universal hex driver 512 (see FIG. 56) in the hex drive socket 258 formed in the proximal end of the reamer guide shaft's locking screw 256. The surgeon may then rotate the hex driver to drive the reamer guide shaft's locking screw 256 thereby driving the threads 260 into the lower threads 42 of the distal stem component 14. As noted above, the hex driver 512 may be embodied as a torque limiting hex driver to prevent over tightening of the locking screw 256.

The surgeon then selects a starting size of a proximal reamer 390. In an illustrative method, the surgeon may select a proximal reamer 390 having a 20 mm diameter as a starting size. The male connector 420 of the selected starting proximal reamer 390 (e.g., the 20 mm proximal reamer) is then inserted into the chuck of the rotary power tool 86 or the manual handle 80. The surgeon then positions the proximal reamer 390 such that the distal end 408 of its guide bore 406 is located above the proximal end of the reamer guide shaft 250. The proximal reamer 390 is then advanced such that the reamer guide shaft 250 enters the guide bore 406 of the proximal reamer 390.

Once inserted over the reamer guide shaft 250, the surgeon activates the rotary power tool 86 to drive (i.e., rotate) the proximal reamer 390 thereby causing the helical cutting flutes 402 of the reamer's cutting head 396 to abrade or otherwise cut the bone tissue of the femur 20. The proximal reamer's depth stop 412 bottoms out on the superior surface 282 of the drive socket 258 of the locking screw 256 of the reamer guide shaft 250 (see FIGS. 22 and 23) when the proximal reamer 390 is fully seated. During such use of the proximal reamer 390, the reamer's viewing windows 414 allow the surgeon to visualize the reamer guide shaft 250 as it is advanced along the reamer's guide bore 406. In doing so, the surgeon can visually confirm that proper seating of the proximal reamer 390 has been achieved by observing the colored mark 280 of the reamer guide shaft 250 through the viewing windows 414 formed in the proximal reamer 390. Specifically, the surgeon may visually confirm that proper seating of the proximal reamer 390 has been achieved when the colored mark 280 of the reamer guide shaft 250 (which is visible through the viewing windows 414) aligns with the colored mark 418 of the proximal reamer 390.

The surgeon then removes the proximal reamer 390 having the starting size (e.g., 20 mm diameter) and progressively reams the patient's femur 20 with increasingly larger proximal reamers 390 until desired cortical bone contact is achieved and the reamed cavity possesses the desired final geometry (i.e., the shape) required to accept the proximal body component 12 selected by the surgeon.

Once the proximal reaming operation is complete, the proximal reamer 390 possessing the final desired size is removed from the femur 20. The reamer guide shaft 250 is then itself removed from the distal stem component 14 by inserting a manual universal hex driver 512 (such as the one shown in FIG. 56) in the hex drive socket 258 formed in the proximal end of the reamer guide shaft's locking screw 256 and rotating the locking screw 256 in the opposite direction it was rotated during installation thereby rotating the locking threads 260 formed in the distal end of the locking screw 256 in a direction which causes them to exit the lower threads 42 of the distal stem component 14. The reamer guide shaft 250 may then be removed from the distal stem component 14.

Figures 54, 55, 56:
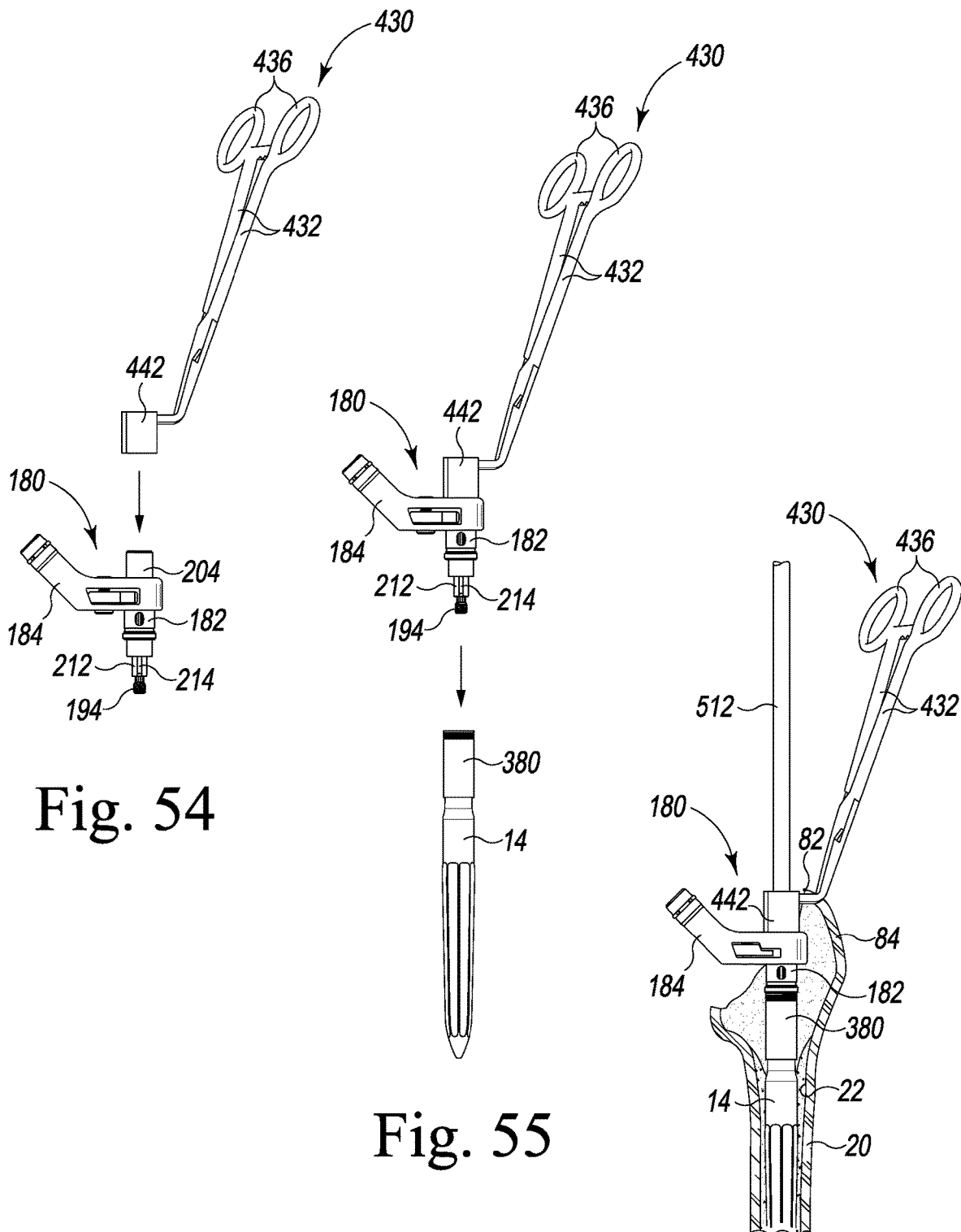
FIGS. 54-56 are elevation views showing the trial insertion tool being used to couple the proximal trial instrument to the distal stem component during performance of a hip revision procedure.

As shown in FIGS. 54-56, once the reamer guide shaft 250 has been removed from the distal stem component 14, a proximal body trialing procedure may be performed. To do so, the surgeon first secures the proximal trial instrument 180 to the distal stem component 14 implanted in the intramedullary canal 22 of the patient's femur 20. Specifically, the surgeon selects a trial shaft 182 which corresponds to the distal stem depth that was referenced during stem insertion (i.e., based on which depth mark 372, 374, 376, 378 was utilized during stem insertion). To insert the trial shaft 182, the surgeon uses the trial insertion tool 430. Specifically, the surgeon urges the two loops 436 of the insertion tool 430 away from one another such that the levers 432 pivot about the pin 434 and the two halves of the retention socket 442 spread slightly away from one another. The stem 204 of the trial shaft 182 may then be advanced into the recess 444 of the retention socket 442. Thereafter, the surgeon squeezes or otherwise urges the two loops 436 toward one another thereby causing the levers 432 to pivot about the pin 434. Doing so urges the two halves of the retention socket 442 toward one another thereby squeezing the stem 204 of the trial shaft 182 so as to retain the trial shaft 182 in the retention socket 442.

The distal end of the trial shaft 182 is then inserted into the superior end of the implanted distal stem component 14. To do so, the surgeon aligns the alignment flat 210 formed on the distal end of the trial shaft 182 with the alignment key 44 extending superiorly from the superior surface of the body 38 of the distal stem component 14 (see FIG. 4). In doing so, the alignment key 214 formed in the distal end of the trial shaft 182 is aligned with, and received into, the keyway 46 formed in the superior surface of the distal stem component 14 (see FIG. 4) thereby inserting the distal end of the trial shaft 182 into the opening formed by the distal stem component's upper threads 40. As a result, the locking threads 194 of the trial shaft 182 are started in the lower threads 42 of the distal stem component 14. The surgeon then inserts the hex driver 512 (see FIG. 56) into the hex drive head 192 of the trial shaft's locking screw 190. Thereafter, the surgeon rotates the hex driver 512 so as to rotate the locking threads 194 formed in the distal end of the trial shaft's locking screw 190 thereby driving the trial shaft's threads 194 into the lower threads 42 of the distal stem component 14. Once the trial shaft 182 is secured to the distal stem component 14, the trial insertion tool 430 is removed. As noted above, the hex driver 512 may be embodied as a torque limiting hex driver to prevent over tightening of the locking screw 190.

As shown in FIGS. 54 and 55, the trial neck 184 may be installed on the trial shaft 182 prior to coupling the trial shaft 182 to the distal stem component 14. If it is not installed beforehand, the trial neck 184 may be installed on the trial shaft 182 after the shaft is coupled to the distal stem component 14. To do so, the surgeon advances the trial neck 184 such that the proximal stem 204 of the trial shaft 182 is received into the bore 228 of the trial neck 184. The trial neck 184 slides down the stem 204 of the trial shaft 182 until the inferior surface 230 of the trial neck's body 224 contacts the shoulder 206 formed in the body 186 of the trial shaft 182 (see also FIGS. 14-17).

Figure 57:
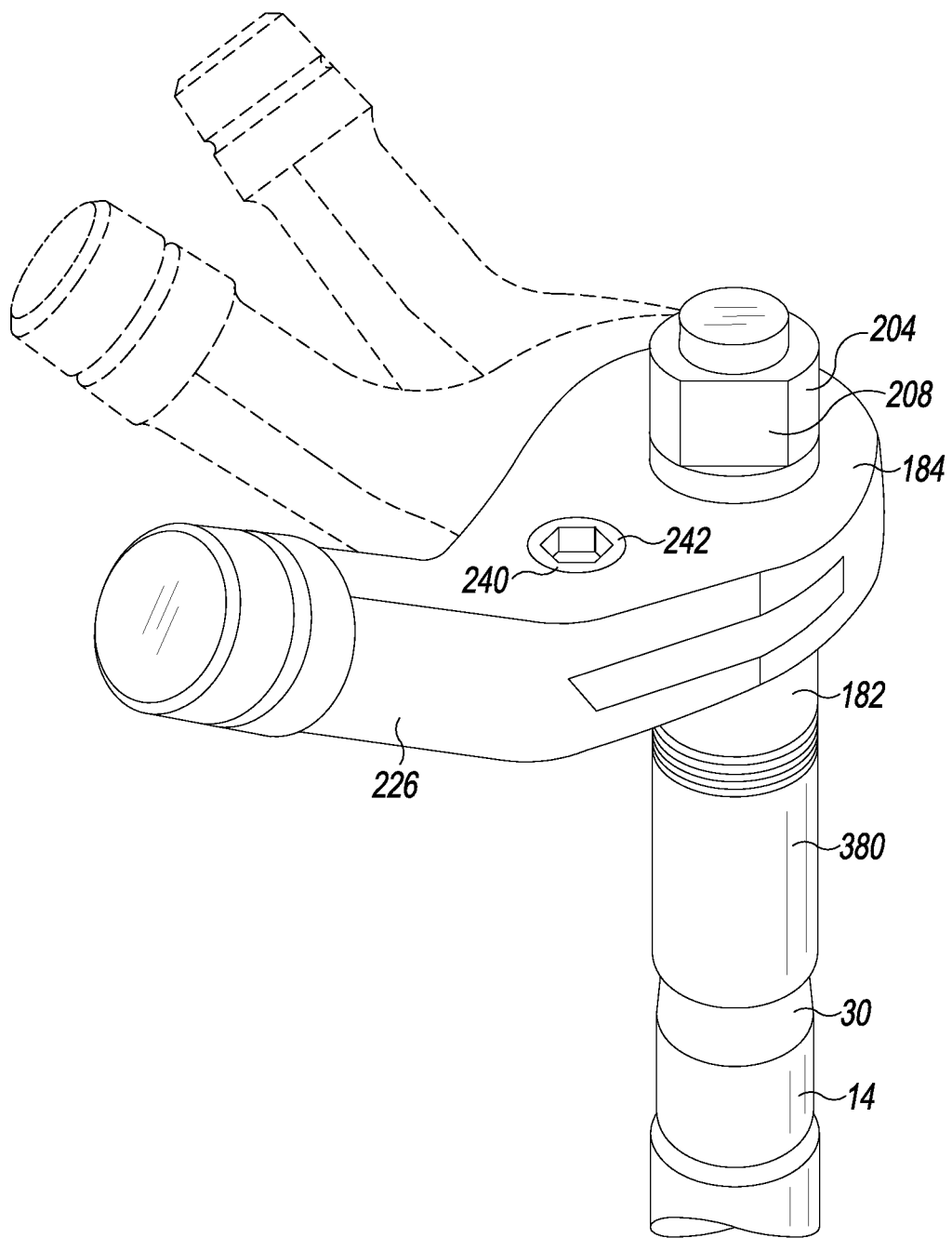
FIG. 57 is an enlarged fragmentary perspective view showing the version of the trial neck being adjusted during performance of a hip revision procedure.

As shown in FIG. 57, the trial neck 184 is freely movable relative to the trial shaft 182 at this point in the process. Upon orientating the trial neck 184 in the proper version, it may be secured in the desired position by inserting a manual universal hex driver 512 (such as the one shown in FIG. 56) in the hex drive head 242 formed in the proximal end of the trial neck's locking screw 240. The surgeon may then tighten the locking screw 240 by rotating the hex driver. By doing so, the locking pawl 244 of the trial neck's friction clamp 238 is urged into position in one of the grooves of the splined surface 208 of the trial shaft 182. The locking pawl 244 contacts the sidewalls forming the groove of the splined surface 208 thereby preventing the trial neck 184 from rotating relative to the trial shaft 182. As noted above, the hex driver 512 may be embodied as a torque limiting hex driver to prevent over tightening of the locking screw 240.

The surgeon may then install a trial femoral head (not shown) on the trial neck 184 and perform a trial reduction to confirm appropriate leg length, offset, and component orientation. If need be after performance of the trial reduction, the surgeon can repeat the process by loosening the locking screw 240 of the trial neck 184, adjusting the version, and then retightening the locking screw 240. Once a trial reduction that is satisfactory to the surgeon is complete, the proximal trial instrument 180 is removed without unlocking the trial neck 184 from the trial shaft 182. In other words, the orientation of the trial neck 184 relative to the trial shaft 182 (i.e., the instrument's version) is maintained during removal of the proximal trial instrument 180 from the implanted distal stem component 14. To remove the proximal trial instrument 180 without disturbing the orientation of the trial neck 184 relative to the trial shaft 182 (i.e., the instrument's version), the trial insertion tool 430 is coupled to the trial shaft 182 in the manner described above. The surgeon then inserts the hex driver 512 into the hex drive head 192 of the trial shaft's locking screw 190 and rotates it in the opposite direction it was rotated during installation thereby rotating the locking threads 194 formed in the distal end of the trial shaft's drive shaft 122 in a direction which causes them to exit the lower threads 42 of the implanted distal stem component 14. The proximal trial instrument 180 may then be removed from the distal stem component 14 with its trial-generated version still intact.

As shown in FIGS. 58-61, the version created by the proximal trial procedure using the proximal trial instrument 180 may be replicated to the proximal body component 12 by use of the version-replicating instrument 460. Initially, the surgeon removes the taper-protecting sleeve 380 so as to expose the tapered post 30 formed in the superior end of the distal stem component 14. The surgeon then inspects the tapered post 30 to ensure that it is dry and clear of debris. The tapered post 30 may be washed with a pressurized saline wash and thereafter thoroughly dried if cleansing is required.

The version-replicating instrument 460 may then be coupled to the implanted distal stem component 14. To do so, the surgeon aligns the alignment key 468 formed in the distal end of the version-replicating instrument 460 with the keyway 46 formed in the superior surface of the distal stem component 14 (see FIG. 4) and inserts the distal end of the version-replicating instrument 460 into the opening formed by the distal stem component's upper threads 40. As can be seen in FIG. 58, the proximal body component 12 may then be installed over the version-replicating instrument 460. To do so, the surgeon advances the proximal body component 12 such that the version-replicating instrument 460 is received into the tapered bore 28 of the proximal body component 12. The proximal body component 12 is then slid down the version-replicating instrument 460 such that the tapered post 30 of the distal stem component 14 is received into its tapered bore 28.

The proximal trial instrument 180, with the trial shaft 182 and trial neck 184 still locked in the version determined during proximal trialing (see FIGS. 54-57), is then coupled to the proximal end of the version-replicating instrument 460. Specifically, as shown in FIGS. 60 and 61, the distal end 212 of the trial shaft 182 of the proximal trial instrument 180 (see FIGS. 14-16) is inserted into the blind hole 470 formed in the proximal end of the version-replicating instrument 460. In doing so, the alignment key 214 formed on the trial shaft 182 of the proximal trial instrument 180 is received into the alignment slot 474 formed in the version-replicating instrument's shaft 462.

The proximal body component 12 may then be rotated to match the version of the proximal trial instrument 180. Namely, the surgeon can view down the longitudinal axis of the version-replicating instrument 460 and rotate the proximal body component 12 so that its neck 16 is aligned with the elongated neck 226 of the trial neck 184. Thus, the proximal body component 12 is placed in the same version that was obtained during proximal trialing (see FIGS. 54-57). Once the version of the proximal trial instrument 180 has been replicated in the position of the proximal body component 12, the proximal trial instrument 180 is then lifted off of the proximal end of the version-replicating instrument 460.

Figure 62:
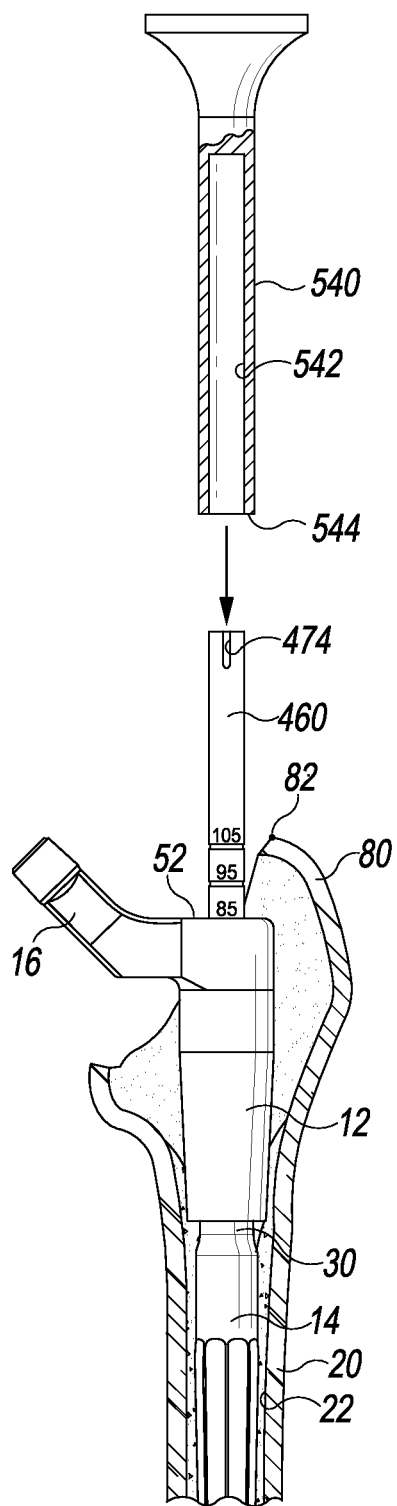
FIGS. 62 and 63 are fragmentary elevation views showing a surgical tamp being used to initially engage the taper lock connection between the distal stem component and the proximal body component during performance of a hip revision procedure.
Figure 63:
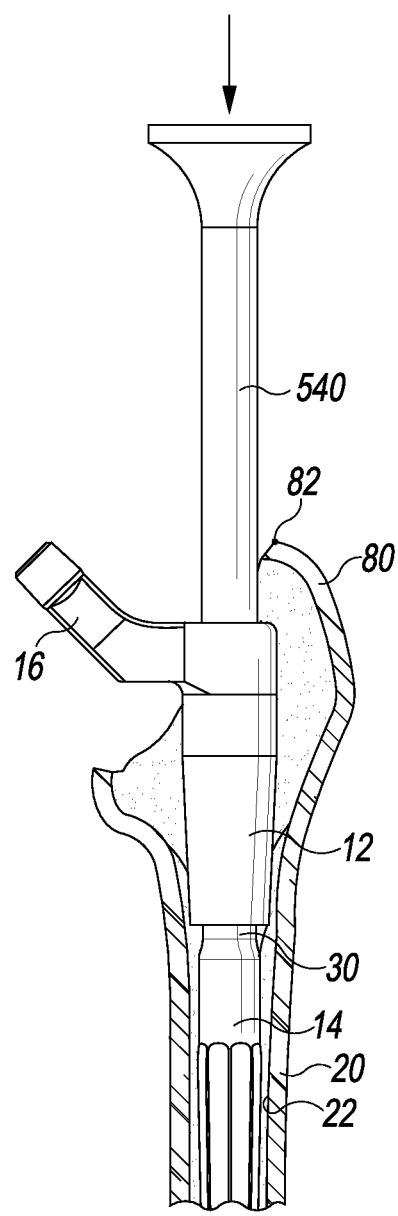

As shown in FIGS. 62 and 63, once the proximal trial instrument 180 has been removed, a taper tamp 540 may be slipped over the version-replicating instrument 460. As can be seen in FIG. 62, the taper tamp 540 has an elongated blind bore 542 formed therein. The bore 542 is sized such that the distal edge 544 of the taper tamp 540 contacts the shoulder 52 of the proximal body component 12 during use of the tamp 540 without disturbing the version-replicating instrument 460. In other words, once slipped over the version-replicating instrument 460, the surgeon may lightly tap the taper tamp 540 with a surgical mallet to initially engage the taper lock connection between the distal stem component 14 and the proximal body component 12 without the version-replicating instrument 460 bottoming out in the bore 542. As described above, each of the colored depth marks 482, 484, 486, 488 on the version-replicating instrument 460 corresponds to the location of the shoulder 52 of the proximal body component 12 once its implanted. As such, the colored depth marks 482, 484, 486, 488 may be used as a depth mark to ensure the tapered post 30 of the distal stem component 14 and the tapered bore 28 of the proximal body component 12 are not significantly dislocated prior to removal of the version-replicating instrument 460. The taper tamp 540 and version-replicating instrument 460 are then removed. The surgeon then uses a taper assembly tool, such as the taper assembly tool described in U.S. patent application Ser. No. 12/815,915 (filed Jun. 15, 2010), to fully engage the taper lock connection between the distal stem component 14 and the proximal body component 12.

The surgeon then obtains an appropriately sized locking bolt 504. The locking bolt 504 is shown in more detail in FIGS. 67-70. As can be seen, the locking bolt 504 has a shank 524 extending away from its head 502. The shank 524 has a number of external threads 526 formed therein. The locking bolt's threads 526 are smaller than the upper threads 40 of the distal stem component 14 such that they pass therethrough without thread engagement during installation of the locking bolt 504. Instead, the locking bolt's threads 526 are sized for thread engagement with the lower threads 42 of the distal stem component 14. As such, in the illustrative embodiment described herein, the locking bolt's threads 526 are embodied as M6 threads. Moreover, like the lower threads 42 of the distal stem component 14, the locking bolt's threads 526 are embodied as modified threads designed to relieve stress risers. In particular, as can be seen best in FIGS. 68-69, the locking bolt's threads 526 are embodied as modified MJ6×1.0 ground threads.

A stepped washer 528 is installed on the locking bolt 504. The stepped washer 528 functions as a biasing member to resist loosening of the locking bolt 504 once it is installed. As can be seen in FIGS. 67-70, the flange of the bolt head 502 functions as a compressor to the stepped washer 528. A clip 530 maintains the stepped washer 528 on the shank 524 of the locking bolt 504 prior to installation.

Both the locking bolt 504 and the stepped washer 528 may be constructed from a medical-grade metal such as stainless steel, cobalt chrome, or titanium, although other metals or alloys may be used. The clip 530 may be constructed from a rigid polymer such as polyetheretherketone (PEEK).

Returning back to FIG. 64, once the surgeon has obtained an appropriately sized locking bolt 504, the locking bolt 504 is then installed to act as a secondary lock between the proximal body component 12 to the distal stem component 14. To do so, the surgeon inserts the locking bolt 504 through the countersunk cavity 32 of the proximal body component 12 (see FIG. 64). Thereafter, the surgeon uses finger pressure to turn the locking bolt 504 thereby causing initial thread engagement between the threads 526 of the locking bolt 504 and the lower threads 42 of the distal stem component 14. The surgeon then applies a predetermined torque to the locking bolt 504. To do so, the surgeon uses the stem stabilizer 490 in conjunction with a torque wrench such as the T-handle torque wrench 520 shown in FIGS. 65 and 66. As shown in FIG. 65, the surgeon first couples the drive socket 522 of the torque wrench 52 to the square-type drive head 496 formed in the proximal end of the stem stabilizer's drive rod 514. Once coupled in such a manner, rotation of the torque wrench 520 causes rotation of the stem stabilizer's drive rod 514 and hence the drive socket 498 formed in its distal end.

The stem stabilizer 490, with the torque wrench 520 secured thereto, is then assembled on the implanted femoral prosthesis 10. In particular, the surgeon advances the stem stabilizer 490 into contact with the femoral prosthesis 10 such that the head 502 of the locking bolt 504 is received into the drive socket 498 of the stem stabilizer's drive rod 514 and the elongated neck 16 of the proximal body component 12 is captured between the tines 510 of the stem stabilizer's fork 508 (see FIG. 66).

Once the stem stabilizer 490 is secured to the implanted femoral prosthesis 10 in such a manner, the surgeon tightens the locking bolt 504. Specifically, the surgeon turns the T-handle torque wrench 520 until it clicks. Such an audible click indicates that the appropriate torque has been applied to the locking bolt 504 thereby providing confirmation to the surgeon that the locking bolt 504 has been fully seated. The stem stabilizer 490, with the torque wrench 520 secured thereto, is then removed from the implanted femoral prosthesis 10.

If for some reason the surgeon needs to disengage the taper lock connection between the distal stem component 14 and the proximal body component 12, the surgeon may then use a taper disassembly tool, such as the taper disassembly tool described in U.S. patent application Ser. No. 12/873,612 (filed Sep. 1, 2010). Prior to using such a disassembly tool, the surgeon first removes the locking bolt 504.

Figure 71:
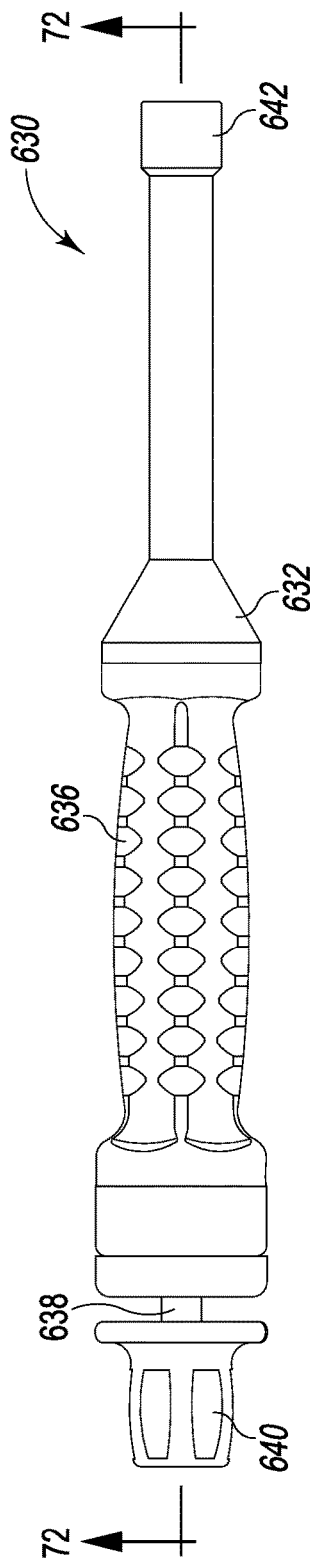
FIG. 71 is an elevation view of another embodiment of a trial insertion tool used during performance of a hip revision procedure.
Figure 72:
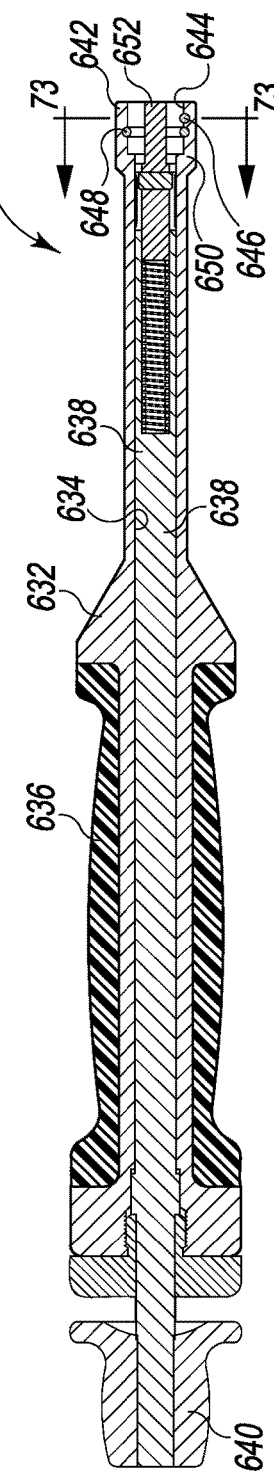
FIG. 72 is a cross sectional view of the trial insertion tool taken along the line 72-72 of FIG. 71, as viewed in the direction of the arrows.
Figure 73:
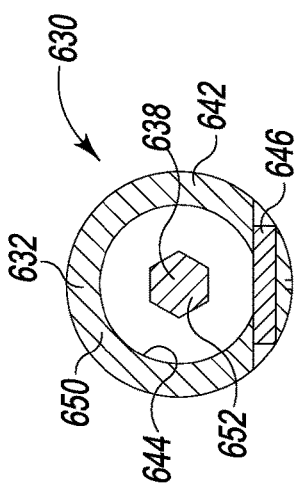
FIG. 73 is an enlarged cross sectional view of the retention socket of the trial insertion tool taken along the line 73-73 of FIG. 72, as viewed in the direction of the arrows.

Referring now to FIGS. 71-73, there is shown another embodiment of a trial insertion tool 630 that may be secured to the proximal trial instrument 180 to facilitate its attachment to the distal reamer 90 or the distal stem component 14 implanted in the intramedullary canal 22 of the patient's femur 20. The trial insertion tool 630 includes a body 632 having an elongated bore 634 extending therethrough. A sleeve 636 is positioned around the insertion tool's body 632. The sleeve 636 is immovably coupled to the outer surface of the insertion tool's body 632, such as by, for example, overmolding. The sleeve 636 functions as a grip for allowing the surgeon to hold the trail insertion tool 630 during assembly of the proximal trial instrument 180 to the distal reamer 90 or the distal stem component 14.

A drive rod 638 is captured in the bore 634. A knob 640 is secured to the proximal end of the drive rod 638. Rotation of the knob 640 causes rotation of the drive rod 638. The drive rod 638 includes a hex drive tip 652 located at its distal end (see FIGS. 72 and 73). When the hex drive tip 652 is positioned in the hex drive head 192 of the proximal trial shaft 182 and rotated, the locking threads 194 formed in the distal end of the trial shaft's drive shaft 122 are likewise rotated. As described above, such rotation of the trial shaft's drive shaft 122 drives the trial shaft's threads 194 into the lower threads 42 of the distal stem component 14 or the threads 112 of the distal reamer 90.

The distal end of the body 632 of the trial insertion tool 630 has a retention socket 642 formed therein. The retention socket 642 is sized and shaped to receive the stem 204 formed in the proximal end 202 of the trial shaft 182. In particular, as shown in the cross sectional view of FIG. 73, the retention socket 642 has a round recess 644 formed therein. The inner diameter of the recess 644 is sized to closely mimic the outer diameter of the stem 204 of the trial shaft 182 so as to receive it therein. As can also be seen in the cross sectional view of FIG. 73, the retention socket 642 has an alignment pin 646 extending therethrough. The alignment pin 646 is arranged substantially perpendicular to the longitudinal axis of the trial insertion tool 630. The alignment pin 646 essentially "flattens" one side of the round recess 644. The alignment pin 646 aligns the trial shaft 182 of the proximal trial instrument 180 in a desired orientation relative to the trial insertion tool 630.

As can be seen in the cross section of FIG. 72, a retainer ring 648 is positioned in the sidewall 650 that defines the recess 644 of the trial insertion tool's retention socket 642. The retainer ring 648 snaps around a groove on the outer surface the stem 204 of the trial shaft 182 to retain the trial shaft 182 of the proximal trial instrument 180 in the retention socket 642.

The metallic components of the trial insertion tool 630 (e.g., the insertion tool's body 632, drive rod 638, etcetera) may be constructed from a medical-grade metal such as stainless steel, cobalt chrome, or titanium, although other metals or alloys may be used. Moreover, in some embodiments, rigid polymers such as polyetheretherketone (PEEK) may also be used. The sleeve 636 may be constructed from a polymer such as delrin or silicone.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. A surgical instrument assembly operable to ream an intramedullary canal of a patient's femur during a surgical procedure to implant a distal stem component of a modular orthopaedic hip prosthesis, comprising:
   a distal reamer having (i) a cutting head that includes a plurality of helical cutting flutes arranged in a geometry that corresponds with the geometry of the distal stem component, and (ii) a female drive socket comprising a female hex drive socket, and
   an extension tool having (i) an elongated shaft (ii) a connector at a proximal end of the elongated shaft configured to couple the extension tool to a rotary drive source, and (iii) a drive spline positioned at a distal end of the elongated shaft in, and engaged with, the female drive socket of the distal reamer such that rotation of the extension tool causes rotation of the distal reamer,
   wherein the extension tool further has a number of visual markings that correspond to depths of the distal reamer within the intramedullary canal of the patient's femur.

2. The surgical instrument assembly of claim 1, wherein:
   the distal reamer further has a number of locking slots arranged around, and opening into, the female drive socket, and
   the extension tool further has a number of locking jaws positioned in the locking slots of the distal reamer.

3. The surgical instrument assembly of claim 2, wherein the locking slots are formed on opposite sides of the female drive socket, and
   the locking jaws are positioned on opposite sides of the drive spline.

4. The surgical instrument assembly of claim 2, wherein:
   the female drive socket extends inwardly from a superior surface, and
   each locking slot of the number of locking slots extends inferiorly from an opening defined in the superior surface.

5. The surgical instrument assembly of claim 2, wherein the distal reamer further has locking slots comprise L-shaped locking slots.

6. The surgical instrument assembly of claim 1, wherein the distal reamer comprises a threaded bore having a superior end that opens into the female drive socket and extending inferiorly away therefrom.

7. The surgical instrument assembly of claim 6, wherein:
   the distal reamer further has a number of locking slots arranged around, and opening into, the female drive socket, and
   the extension tool further has a number of locking jaws positioned in the locking slots of the distal reamer.

8. The surgical instrument assembly of claim 7, wherein the locking slots are formed on opposite sides of the female drive socket, and
   the locking jaws are positioned on opposite sides of the drive spline.

9. The surgical instrument assembly of claim 7, wherein:
   the female drive socket extends inwardly from a superior surface, and each locking slot of the number of locking slots extends inferiorly from an opening defined in the superior surface.

10. The surgical instrument assembly of claim 7, wherein the locking slots comprise L-shaped locking slots.

11. The surgical instrument assembly of claim 1, wherein the connector of the extension tool is configured to fit in a chuck of a rotary power tool.

12. A surgical instrument assembly operable to ream an intramedullary canal of a patient's femur during a surgical procedure to implant a distal stem component of a modular orthopaedic hip prosthesis, comprising:
 a distal reamer having (i) a cutting head that includes a plurality of helical cutting flutes arranged in a geometry that corresponds with the geometry of the distal stem component, (ii) a female drive socket, and (iii) a locking slot opening into the female drive socket, and
 an extension tool having (i) an elongated shaft (ii) a connector at a proximal end of the elongated shaft configured to couple the extension tool to a rotary drive source, (iii) a drive spline positioned at a distal end of the elongated shaft in, and engaged with, the female drive socket of the distal reamer such that rotation of the extension tool causes rotation of the distal reamer, and (iv) a moveable locking jaw positioned in the locking slot to secure the extension tool to the distal reamer.

13. The surgical instrument assembly of claim 12, wherein the extension tool further include a lever operable to move the locking jaw to selectively engage the distal reamer.

14. The surgical instrument assembly of claim 12, wherein the extension tool further has a number of visual markings that correspond to depths of the distal reamer within the intramedullary canal of the patient's femur.

15. The surgical instrument assembly of claim 12, wherein the distal reamer comprises a threaded bore having a superior end that opens into the female drive socket and extending inferiorly away therefrom.

16. The surgical instrument assembly of claim 15, wherein:
 the female drive socket extends inwardly from a superior surface, and
 the locking slot extends inferiorly from an opening defined in the superior surface.

17. The surgical instrument assembly of claim 12, wherein the locking slot is an L-shaped locking slot.

18. The surgical instrument assembly of claim 12, wherein the connector of the extension tool is configured to fit in a chuck of a rotary power tool.

19. The surgical instrument assembly of claim 12, wherein the female drive socket comprises a female hex drive socket.

* * * * *